(12) United States Patent
Rospierski et al.

(10) Patent No.: US 12,390,056 B2
(45) Date of Patent: *Aug. 19, 2025

(54) MONITORING MODULES FOR HAND HYGIENE DISPENSERS

(71) Applicant: Ecolab USA Inc., Saint Paul, MN (US)

(72) Inventors: Jeffrey Rospierski, Alden, NY (US); David L. Snodgrass, Saint Paul, MN (US); Andrew M. Schultz, Minneapolis, MN (US); Viktor Slobodyan, Duluth, MN (US); Cheryl A. Littau, Apple Valley, MN (US); Kenneth T. Dobizl, Mounds View, MN (US)

(73) Assignee: Ecolab USA Inc., Saint Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/404,202

(22) Filed: Jan. 4, 2024

(65) Prior Publication Data

US 2024/0292981 A1    Sep. 5, 2024

Related U.S. Application Data

(63) Continuation of application No. 17/648,389, filed on Jan. 19, 2022, now Pat. No. 11,903,537, which is a
(Continued)

(51) Int. Cl.
*A47K 5/12* (2006.01)
*G08B 21/24* (2006.01)
*G16H 40/20* (2018.01)

(52) U.S. Cl.
CPC .......... *A47K 5/1217* (2013.01); *G08B 21/245* (2013.01); *G16H 40/20* (2018.01)

(58) Field of Classification Search
None
See application file for complete search history.

(56) References Cited

U.S. PATENT DOCUMENTS 1,121,500 A    12/1914    Hines
1,643,828 A    9/1927    Young
(Continued)

FOREIGN PATENT DOCUMENTS

AU    200114943 B2    5/2001
AU    2012360763 A1    7/2014
(Continued)

OTHER PUBLICATIONS

"3M and Patient Care Technology Systems Collaborate on State of-the-Art Automated Hand •Hygiene Solution to Improve Compliance", [Online] Retrieved from the internet: <http://news.3m.com/pt/presspressrelease/company/3m-and-patient-care-technology>, (Apr. 13, 2017), 2 pgs.
(Continued)

*Primary Examiner* — Muhammad Adnan
(74) *Attorney, Agent, or Firm* — Schwegman Lundberg & Woessner, P.A.

(57) ABSTRACT

A wireless dispenser beacon module for a product dispenser comprises a bottle presence trigger configured to detect one of presence or absence of a product bottle in the product dispenser; an actuation sensor configured to detect actuation of the product dispenser; and a module controller configured to wirelessly transmit dispenser data indicative of the detected one of presence or absence of the product bottle in the product dispenser associated with each detected actuation of the product dispenser.

24 Claims, 17 Drawing Sheets

Related U.S. Application Data continuation of application No. 15/912,999, filed on Mar. 6, 2018, now Pat. No. 11,272,815.

(60) Provisional application No. 62/468,214, filed on Mar. 7, 2017.

(56) References Cited

U.S. PATENT DOCUMENTS

| | | |
|---|---|---|
| 1,985,615 A | 12/1934 | August |
| 2,219,597 A | 10/1940 | Lutz |
| 2,319,739 A | 5/1943 | Kessler |
| 2,333,791 A | 11/1943 | Hutchison, Jr. |
| 3,091,327 A | 5/1963 | Lalley |
| 3,136,157 A | 6/1964 | Seed et al. |
| 3,412,254 A | 11/1968 | Hans et al. |
| 3,526,334 A | 9/1970 | Ashton et al. |
| 3,578,094 A | 5/1971 | Henry et al. |
| 3,653,544 A | 4/1972 | Young et al. |
| 3,736,584 A | 5/1973 | Hackett et al. |
| 3,743,598 A | 7/1973 | Field |
| 3,754,871 A | 8/1973 | Hessel et al. |
| 3,760,166 A | 9/1973 | Adams et al. |
| 3,761,909 A | 9/1973 | Schweitzer et al. |
| 3,772,193 A | 11/1973 | Nelli et al. |
| 3,774,056 A | 11/1973 | Sample et al. |
| 3,786,467 A | 1/1974 | Cotter |
| 3,796,349 A | 3/1974 | Weber |
| 3,801,977 A | 4/1974 | Cotter |
| 3,826,113 A | 7/1974 | Boraas et al. |
| 3,826,408 A | 7/1974 | Berndt et al. |
| 3,866,198 A | 2/1975 | Cohen |
| 3,961,321 A | 6/1976 | Moss |
| 3,986,182 A | 10/1976 | Hackett |
| 4,040,515 A | 8/1977 | Hessel et al. |
| 4,046,996 A | 9/1977 | Williams et al. |
| 4,076,146 A | 2/1978 | Lausberg et al. |
| 4,083,298 A | 4/1978 | Schotten |
| 4,117,462 A | 9/1978 | Miller |
| 4,198,618 A | 4/1980 | Kleinschmidt |
| 4,199,001 A | 4/1980 | Kratz |
| 4,209,776 A | 6/1980 | Frederick |
| 4,211,517 A | 7/1980 | Schmid |
| 4,241,400 A | 12/1980 | Kiefer |
| 4,247,396 A | 1/1981 | Buesing |
| 4,265,266 A | 5/1981 | Kierbow et al. |
| 4,275,390 A | 6/1981 | Heywang et al. |
| 4,319,349 A | 3/1982 | Hackett |
| 4,353,482 A | 10/1982 | Tomlinson et al. |
| 4,360,905 A | 11/1982 | Hackett |
| 4,373,418 A | 2/1983 | Rhodes et al. |
| 4,380,726 A | 4/1983 | Sado et al. |
| 4,396,828 A | 8/1983 | Dino et al. |
| 4,402,426 A | 9/1983 | Faulkner et al. |
| 4,404,639 A | 9/1983 | Mcguire et al. |
| 4,463,844 A | 8/1984 | Huffman et al. |
| 4,482,785 A | 11/1984 | Finnegan et al. |
| 4,486,910 A | 12/1984 | Saalmann et al. |
| 4,509,543 A | 4/1985 | Livingston et al. |
| 4,523,219 A | 6/1985 | Heidegger et al. |
| 4,539,846 A | 9/1985 | Grossman |
| 4,573,606 A | 3/1986 | Lewis et al. |
| 4,590,460 A | 5/1986 | Abbott et al. |
| 4,597,091 A | 6/1986 | Blake |
| 4,606,085 A | 8/1986 | Davies |
| 4,630,654 A | 12/1986 | Kennedy, Jr. |
| 4,644,509 A | 2/1987 | Kiewit et al. |
| 4,676,399 A | 6/1987 | Burckhardt |
| 4,688,585 A | 8/1987 | Vetter |
| 4,690,305 A | 9/1987 | Copeland |
| 4,697,243 A | 9/1987 | Moore et al. |
| 4,707,848 A | 11/1987 | Durston et al. |
| 4,711,370 A | 12/1987 | Goudy, Jr. et al. |
| 4,727,522 A | 2/1988 | Steiner et al. |
| 4,729,120 A | 3/1988 | Steiner et al. |
| 4,733,971 A | 3/1988 | Pratt |
| 4,756,321 A | 7/1988 | Livingston et al. |
| 4,766,548 A | 8/1988 | Cedrone et al. |
| 4,770,859 A | 9/1988 | Heiser, Jr. |
| 4,800,372 A * | 1/1989 | Poteet ............... G08B 21/182 340/625 |
| 4,826,661 A | 5/1989 | Copeland et al. |
| 4,834,546 A | 5/1989 | Puetz |
| 4,837,811 A | 6/1989 | Butler et al. |
| 4,839,597 A | 6/1989 | Rowland et al. |
| 4,843,579 A | 6/1989 | Andrews et al. |
| 4,845,965 A | 7/1989 | Copeland et al. |
| 4,848,381 A | 7/1989 | Livingston et al. |
| 4,858,449 A | 8/1989 | Lehn |
| 4,867,196 A | 9/1989 | Zetena et al. |
| 4,867,343 A | 9/1989 | Ricciardi et al. |
| 4,896,144 A | 1/1990 | Bogstad |
| 4,908,190 A | 3/1990 | Maglio et al. |
| 4,938,240 A | 7/1990 | Lakhan et al. |
| 4,944,428 A | 7/1990 | Gmuer et al. |
| 4,964,185 A | 10/1990 | Lehn |
| 4,969,011 A | 11/1990 | Faull et al. |
| 4,974,646 A | 12/1990 | Martin et al. |
| 4,976,137 A | 12/1990 | Decker et al. |
| 4,980,292 A | 12/1990 | Elbert et al. |
| 4,987,402 A | 1/1991 | Nykerk |
| 4,991,146 A | 2/1991 | Ransdell et al. |
| 4,999,124 A | 3/1991 | Copeland |
| 5,006,995 A | 4/1991 | Toschi et al. |
| 5,014,211 A | 5/1991 | Turner et al. |
| 5,014,877 A | 5/1991 | Roos |
| 5,024,352 A | 6/1991 | Gmuer et al. |
| 5,036,479 A | 7/1991 | Prednis et al. |
| 5,038,807 A | 8/1991 | Bailey et al. |
| 5,038,973 A | 8/1991 | Gmuer |
| 5,040,699 A | 8/1991 | Gangemi |
| 5,043,860 A | 8/1991 | Koether et al. |
| 5,053,206 A | 10/1991 | Maglio et al. |
| 5,059,954 A * | 10/1991 | Beldham ............ G08B 21/182 73/302 |
| 5,064,094 A | 11/1991 | Roos et al. |
| 5,083,298 A | 1/1992 | Citterio et al. |
| 5,110,364 A | 5/1992 | Mazur et al. |
| 5,115,842 A | 5/1992 | Crafts et al. |
| 5,136,281 A | 8/1992 | Bonaquist |
| 5,147,615 A | 9/1992 | Bird et al. |
| 5,150,099 A | 9/1992 | Lienau |
| 5,153,520 A | 10/1992 | Dumbeck |
| 5,158,895 A | 10/1992 | Ashihara et al. |
| 5,199,118 A | 4/1993 | Cole et al. |
| 5,202,666 A | 4/1993 | Knippscheer |
| 5,203,366 A | 4/1993 | Czeck et al. |
| 5,219,224 A | 6/1993 | Pratt |
| 5,222,027 A | 6/1993 | Williams et al. |
| 5,240,326 A | 8/1993 | Evanson |
| 5,245,317 A | 9/1993 | Chidley et al. |
| 5,263,006 A | 11/1993 | Hermesmeyer |
| 5,268,153 A | 12/1993 | Muller |
| 5,279,448 A | 1/1994 | Hanlin et al. |
| 5,283,639 A | 2/1994 | Esch et al. |
| 5,294,022 A | 3/1994 | Earle |
| 5,309,409 A | 5/1994 | Jones et al. |
| 5,316,195 A | 5/1994 | Moksnes et al. |
| 5,322,571 A | 6/1994 | Plummer et al. |
| 5,332,312 A | 7/1994 | Evanson |
| 5,345,379 A | 9/1994 | Brous et al. |
| 5,369,032 A | 11/1994 | Pratt |
| 5,370,267 A | 12/1994 | Schroeder |
| 5,389,344 A | 2/1995 | Copeland et al. |
| 5,390,385 A | 2/1995 | Beldham |
| 5,397,028 A | 3/1995 | Jesadanont |
| 5,400,018 A | 3/1995 | Scholl et al. |
| 5,404,893 A | 4/1995 | Brady et al. |
| 5,407,598 A | 4/1995 | Olson et al. |
| 5,411,716 A | 5/1995 | Thomas et al. |
| 5,427,748 A | 6/1995 | Wiedrich et al. |
| 5,430,293 A | 7/1995 | Sato et al. |
| 5,463,595 A | 10/1995 | Rodhall et al. |
| 5,467,481 A | 11/1995 | Srivastava |
| 5,476,385 A | 12/1995 | Parikh et al. |

(56) References Cited

U.S. PATENT DOCUMENTS

| | | |
|---|---|---|
| 5,480,068 A | 1/1996 | Frazier et al. |
| 5,497,914 A | 3/1996 | Maltsis |
| 5,500,050 A | 3/1996 | Chan et al. |
| 5,505,915 A | 4/1996 | Copeland et al. |
| 5,556,478 A | 9/1996 | Brady et al. |
| 5,570,079 A | 10/1996 | Dockery |
| 5,580,448 A | 12/1996 | Brandreth, III |
| 5,581,982 A | 12/1996 | Chadwell et al. |
| 5,584,025 A | 12/1996 | Keithley et al. |
| 5,584,079 A | 12/1996 | Wong et al. |
| 5,609,417 A | 3/1997 | Otte |
| 5,610,589 A | 3/1997 | Evans et al. |
| 5,619,183 A | 4/1997 | Ziegra et al. |
| 5,624,810 A | 4/1997 | Miller et al. |
| 5,625,659 A | 4/1997 | Sears |
| 5,625,908 A | 5/1997 | Shaw |
| 5,632,411 A | 5/1997 | Harty et al. |
| 5,636,008 A | 6/1997 | Lobiondo et al. |
| 5,638,417 A | 6/1997 | Boyer et al. |
| 5,653,269 A | 8/1997 | Miller et al. |
| 5,661,471 A | 8/1997 | Kotlicki |
| 5,671,262 A | 9/1997 | Boyer et al. |
| 5,679,173 A | 10/1997 | Hartman |
| 5,681,400 A | 10/1997 | Brady et al. |
| 5,684,458 A | 11/1997 | Calvarese |
| 5,687,717 A | 11/1997 | Halpern et al. |
| 5,694,323 A | 12/1997 | Koropitzer et al. |
| 5,695,091 A | 12/1997 | Winings et al. |
| 5,724,261 A | 3/1998 | Denny et al. |
| 5,731,526 A | 3/1998 | Kindrick |
| 5,735,925 A | 4/1998 | Scott |
| 5,745,381 A | 4/1998 | Tanaka et al. |
| 5,757,664 A | 5/1998 | Rogers et al. |
| 5,758,300 A | 5/1998 | Abe |
| 5,759,501 A | 6/1998 | Livingston et al. |
| 5,761,278 A | 6/1998 | Pickett et al. |
| 5,762,096 A | 6/1998 | Mirabile |
| 5,764,136 A | 6/1998 | Harron |
| 5,765,605 A | 6/1998 | Waymire et al. |
| 5,769,536 A | 6/1998 | Kotylak |
| 5,771,925 A | 6/1998 | Lewandowski |
| D396,009 S | 7/1998 | Reubens |
| 5,777,895 A | 7/1998 | Kuroda et al. |
| 5,781,942 A | 7/1998 | Shaw et al. |
| 5,793,653 A * | 8/1998 | Segal .................. G07C 1/10 700/285 |
| 5,808,553 A | 9/1998 | Cunningham |
| 5,812,059 A | 9/1998 | Shaw et al. |
| 5,821,523 A | 10/1998 | Bennett et al. |
| 5,826,749 A | 10/1998 | Howland et al. |
| 5,827,486 A | 10/1998 | Crossdale |
| 5,839,097 A | 11/1998 | Klausner |
| 5,851,291 A | 12/1998 | Poterala et al. |
| 5,861,881 A | 1/1999 | Freeman et al. |
| 5,864,783 A | 1/1999 | Struck et al. |
| 5,875,430 A | 2/1999 | Koether |
| 5,885,446 A | 3/1999 | Mcgrew, Jr. |
| 5,887,145 A | 3/1999 | Harari et al. |
| 5,887,975 A | 3/1999 | Mordaunt et al. |
| 5,897,671 A | 4/1999 | Newman et al. |
| 5,900,067 A | 5/1999 | Jones |
| 5,902,749 A | 5/1999 | Lichtwardt et al. |
| 5,913,915 A | 6/1999 | McQuinn |
| 5,917,425 A | 6/1999 | Crimmins et al. |
| 5,919,567 A | 7/1999 | Okada et al. |
| 5,931,877 A | 8/1999 | Smith et al. |
| 5,933,479 A | 8/1999 | Michael et al. |
| 5,938,074 A | 8/1999 | Dartus |
| 5,939,974 A | 8/1999 | Heagle et al. |
| 5,945,910 A | 8/1999 | Gorra |
| 5,952,924 A | 9/1999 | Evans et al. |
| 5,954,069 A | 9/1999 | Foster |
| 5,956,487 A | 9/1999 | Venkatraman et al. |
| 5,961,561 A | 10/1999 | Wakefield, II |
| 5,966,753 A | 10/1999 | Gauthier et al. |
| 5,967,202 A | 10/1999 | Mullen et al. |
| 5,973,696 A | 10/1999 | Agranat et al. |
| 5,974,345 A | 10/1999 | Buck et al. |
| 5,975,352 A | 11/1999 | Spriggs et al. |
| 5,977,913 A | 11/1999 | Christ |
| 5,979,703 A | 11/1999 | Nystrom |
| 5,980,090 A | 11/1999 | Royal, Jr. et al. |
| 5,987,105 A | 11/1999 | Jenkins et al. |
| 5,992,686 A | 11/1999 | Cline et al. |
| 6,003,070 A | 12/1999 | Frantz |
| 6,007,788 A | 12/1999 | Bellon et al. |
| 6,012,041 A | 1/2000 | Brewer et al. |
| 6,029,286 A | 2/2000 | Funk |
| 6,031,461 A | 2/2000 | Lynn |
| 6,038,331 A | 3/2000 | Johnson |
| 6,049,792 A | 4/2000 | Hart et al. |
| 6,061,668 A | 5/2000 | Sharrow |
| 6,065,639 A | 5/2000 | Maddox et al. |
| 6,073,124 A | 6/2000 | Krishnan et al. |
| 6,082,149 A | 7/2000 | Woods |
| 6,098,843 A | 8/2000 | Soberanis et al. |
| 6,120,175 A | 9/2000 | Tewell |
| D431,404 S * | 10/2000 | Brazis .................. D6/545 |
| 6,125,482 A | 10/2000 | Foster |
| 6,129,449 A | 10/2000 | Mccain et al. |
| 6,130,607 A | 10/2000 | Mcclanahan et al. |
| 6,133,555 A | 10/2000 | Brenn |
| 6,136,184 A | 10/2000 | King |
| 6,147,607 A | 11/2000 | Lynn |
| 6,164,189 A | 12/2000 | Anson |
| 6,164,439 A | 12/2000 | Stebnicki et al. |
| 6,167,358 A | 12/2000 | Othmer et al. |
| 6,175,308 B1 | 1/2001 | Tallman et al. |
| 6,191,693 B1 | 2/2001 | Sangsingkeow |
| 6,211,788 B1 | 4/2001 | Lynn et al. |
| 6,213,424 B1 | 4/2001 | Helfer-grand |
| 6,220,312 B1 | 4/2001 | Hirsch et al. |
| 6,221,788 B1 | 4/2001 | Kobayashi et al. |
| 6,236,317 B1 | 5/2001 | Cohen et al. |
| 6,236,953 B1 | 5/2001 | Segal |
| 6,247,621 B1 * | 6/2001 | Lewis .................. A47K 5/12 222/153.13 |
| 6,249,778 B1 | 6/2001 | Vaghi |
| 6,259,956 B1 | 7/2001 | Myers et al. |
| 6,269,975 B2 | 8/2001 | Soberanis et al. |
| 6,278,372 B1 | 8/2001 | Velasco, Jr. et al. |
| 6,279,777 B1 | 8/2001 | Goodin et al. |
| 6,288,641 B1 | 9/2001 | Casais |
| 6,291,000 B1 | 9/2001 | Hayakawa |
| 6,314,282 B1 | 11/2001 | Weber et al. |
| 6,321,204 B1 | 11/2001 | Kazami et al. |
| 6,330,499 B1 | 12/2001 | Chou et al. |
| 6,331,964 B1 | 12/2001 | Barone |
| 6,347,724 B1 | 2/2002 | Chen et al. |
| 6,351,223 B1 | 2/2002 | Deweerd et al. |
| 6,356,205 B1 | 3/2002 | Salvo et al. |
| 6,357,292 B1 | 3/2002 | Schultz et al. |
| 6,360,181 B1 | 3/2002 | Gemmell et al. |
| 6,368,420 B1 | 4/2002 | Angevaare et al. |
| 6,370,454 B1 | 4/2002 | Moore |
| 6,375,038 B1 | 4/2002 | Daansen et al. |
| 6,377,868 B1 | 4/2002 | Gardner, Jr. |
| 6,392,546 B1 | 5/2002 | Smith |
| 6,404,837 B1 | 6/2002 | Thompson et al. |
| 6,417,773 B1 | 7/2002 | Vlahos et al. |
| 6,418,371 B1 | 7/2002 | Arnold |
| 6,426,701 B1 * | 7/2002 | Levy .................. G08B 21/24 222/39 |
| 6,438,471 B1 | 8/2002 | Katagishi et al. |
| 6,463,940 B1 | 10/2002 | Thomas et al. |
| 6,472,615 B1 | 10/2002 | Carlson |
| 6,476,385 B1 | 11/2002 | Albert |
| 6,485,979 B1 | 11/2002 | Kippenhan et al. |
| 6,490,513 B1 | 12/2002 | Fish et al. |
| 6,523,193 B2 | 2/2003 | Saraya |
| 6,524,390 B1 | 2/2003 | Jones |
| 6,547,097 B1 | 4/2003 | Cavallaro et al. |
| 6,561,381 B1 | 5/2003 | Osterheld et al. |
| 6,577,240 B2 | 6/2003 | Armstrong |

(56) References Cited

U.S. PATENT DOCUMENTS

| | | |
|---|---|---|
| 6,611,207 B1 | 8/2003 | Yuan et al. |
| 6,681,003 B2 | 1/2004 | Linder et al. |
| 6,697,706 B2 | 2/2004 | Gardner, Jr. |
| 6,707,873 B2 | 3/2004 | Thompson et al. |
| 6,718,394 B2 | 4/2004 | Cain |
| 6,727,818 B1 | 4/2004 | Wildman et al. |
| 6,730,024 B2 | 5/2004 | Freyre et al. |
| 6,749,148 B2 | 6/2004 | Helfer-grand |
| 6,759,959 B2 | 7/2004 | Wildman |
| 6,762,161 B2 | 7/2004 | Sava et al. |
| 6,778,092 B2 | 8/2004 | Braune |
| 6,781,523 B2 | 8/2004 | Matsui et al. |
| 6,792,395 B2 | 9/2004 | Roberts |
| 6,799,085 B1 | 9/2004 | Crisp, III |
| 6,807,460 B2 | 10/2004 | Black et al. |
| 6,870,846 B2 | 3/2005 | Cain |
| 6,882,278 B2 | 4/2005 | Winings et al. |
| 6,882,315 B2 | 4/2005 | Richley et al. |
| 6,883,563 B2 | 4/2005 | Smith |
| 6,893,321 B1 | 5/2005 | Buchanan et al. |
| 6,896,140 B1 | 5/2005 | Perry |
| 6,897,780 B2 | 5/2005 | Ulrich et al. |
| 6,917,290 B2 | 7/2005 | Land |
| 6,919,567 B2 | 7/2005 | Iwasawa |
| 6,950,683 B2 | 9/2005 | Hunt |
| 6,956,498 B1 | 10/2005 | Gauthier et al. |
| 6,970,860 B1 | 11/2005 | Liu et al. |
| 6,975,231 B2 | 12/2005 | Lane et al. |
| 6,977,588 B2 | 12/2005 | Schotz et al. |
| 6,987,228 B1 | 1/2006 | Macmichael et al. |
| 6,991,779 B2 | 1/2006 | Steiner et al. |
| 7,015,816 B2 | 3/2006 | Wildman et al. |
| 7,023,341 B2 | 4/2006 | Stilp |
| 7,023,356 B2 | 4/2006 | Burkhardt et al. |
| 7,042,361 B2 | 5/2006 | Kazdin et al. |
| 7,056,050 B2 | 6/2006 | Sacks |
| 7,067,054 B2 | 6/2006 | Fritze |
| 7,069,188 B2 | 6/2006 | Roberts |
| 7,075,412 B1 | 7/2006 | Reynolds et al. |
| 7,099,781 B1 | 8/2006 | Heidl et al. |
| 7,099,856 B2 | 8/2006 | Barangan et al. |
| 7,117,374 B2 | 10/2006 | Hill et al. |
| 7,119,688 B2 | 10/2006 | Wildman |
| 7,119,692 B2 | 10/2006 | Lieffort et al. |
| 7,128,215 B2 | 10/2006 | Danechi |
| 7,142,108 B2 | 11/2006 | Diener et al. |
| 7,154,397 B2 | 12/2006 | Zerhusen et al. |
| 7,157,045 B2 | 1/2007 | Mcvey |
| 7,160,846 B2 | 1/2007 | Biering et al. |
| 7,175,048 B2 | 2/2007 | Wolfschaffner |
| 7,187,287 B2 | 3/2007 | Ryal |
| 7,191,090 B1 | 3/2007 | Cunningham et al. |
| 7,201,005 B2 | 4/2007 | Voglewede et al. |
| 7,202,780 B2 | 4/2007 | Teller |
| 7,228,990 B2 | 6/2007 | Schmidt |
| 7,236,097 B1 | 6/2007 | Cunningham |
| 7,242,306 B2 | 7/2007 | Wildman et al. |
| 7,242,307 B1 | 7/2007 | Leblond et al. |
| 7,248,933 B2 | 7/2007 | Wildman |
| 7,265,673 B2 | 9/2007 | Teller |
| 7,266,347 B2 | 9/2007 | Gross |
| 7,267,531 B2 | 9/2007 | Anderson et al. |
| 7,271,728 B2 | 9/2007 | Taylor et al. |
| 7,272,537 B2 | 9/2007 | Mogadam |
| 7,286,057 B2 | 10/2007 | Bolling |
| 7,292,914 B2 | 11/2007 | Jungmann et al. |
| 7,293,645 B2 | 11/2007 | Harper et al. |
| 7,315,245 B2 | 1/2008 | Lynn et al. |
| 7,320,418 B2 | 1/2008 | Sassoon |
| 7,330,108 B2 | 2/2008 | Thomas |
| 7,372,367 B2 | 5/2008 | Lane et al. |
| 7,375,640 B1 | 5/2008 | Plost |
| 7,400,264 B2 | 7/2008 | Boaz |
| 7,408,470 B2 | 8/2008 | Wildman et al. |
| 7,411,511 B2 | 8/2008 | Kennish et al. |
| 7,423,533 B1 | 9/2008 | Leblond et al. |
| 7,425,900 B2 | 9/2008 | Lynn et al. |
| 7,440,620 B1 | 10/2008 | Aartsen |
| 7,443,302 B2 | 10/2008 | Reeder et al. |
| 7,443,305 B2 | 10/2008 | Verdiramo |
| RE40,588 E | 11/2008 | Ostendorf et al. |
| 7,450,472 B2 | 11/2008 | Guyvarch |
| 7,450,477 B2 | 11/2008 | Kim et al. |
| 7,457,869 B2 | 11/2008 | Kernan |
| 7,474,215 B2 | 1/2009 | Scott et al. |
| 7,477,148 B2 | 1/2009 | Lynn et al. |
| 7,482,936 B2 | 1/2009 | Bolling |
| 7,486,193 B2 | 2/2009 | Elwell |
| 7,487,538 B2 | 2/2009 | Mok |
| 7,490,045 B1 | 2/2009 | Flores et al. |
| 7,496,479 B2 | 2/2009 | Garcia et al. |
| 7,530,729 B2 | 5/2009 | Ocallaghan |
| 7,538,680 B2 | 5/2009 | Scott et al. |
| 7,551,092 B1 | 6/2009 | Henry |
| 7,597,122 B1 | 10/2009 | Smith |
| 7,600,137 B2 | 10/2009 | Trappeniers et al. |
| 7,605,704 B2 | 10/2009 | Munro et al. |
| 7,611,030 B2 | 11/2009 | Reynolds et al. |
| 7,616,122 B2 | 11/2009 | Bolling |
| 7,649,884 B1 | 1/2010 | Ahmed et al. |
| 7,682,464 B2 | 3/2010 | Glenn et al. |
| 7,718,395 B2 | 5/2010 | Carling |
| 7,755,494 B2 | 7/2010 | Melker et al. |
| 7,770,782 B2 | 8/2010 | Sahud |
| 7,780,453 B2 | 8/2010 | Carling |
| 7,783,380 B2 | 8/2010 | York et al. |
| 7,785,109 B2 | 8/2010 | Carling |
| 7,812,730 B2 | 10/2010 | Wildman et al. |
| 7,855,651 B2 | 12/2010 | LeBlond et al. |
| 7,891,523 B2 | 2/2011 | Mehus et al. |
| 7,893,842 B2 | 2/2011 | Deutsch |
| 7,898,407 B2 | 3/2011 | Hufton et al. |
| 7,952,484 B2 | 5/2011 | Lynn |
| 7,978,564 B2 | 7/2011 | De La Huerga |
| 7,982,619 B2 | 7/2011 | Bolling |
| 8,020,733 B2 | 9/2011 | Snodgrass |
| 8,026,821 B2 | 9/2011 | Reeder et al. |
| 8,040,245 B2 | 10/2011 | Koblasz |
| 8,045,498 B2 | 10/2011 | Hyland |
| 8,056,768 B2 | 11/2011 | Snodgrass |
| 8,085,155 B2 | 12/2011 | Prodanovich et al. |
| 8,087,543 B2 * | 1/2012 | Yang .......... A47K 5/1217 222/642 |
| D654,743 S | 2/2012 | Rospierski |
| 8,146,613 B2 | 4/2012 | Barnhill et al. |
| 8,152,027 B1 | 4/2012 | Baker |
| 8,154,412 B2 | 4/2012 | Verdiramo |
| 8,164,439 B2 * | 4/2012 | Dempsey .......... G08B 13/1427 367/137 |
| 8,196,810 B2 | 6/2012 | Sahud |
| 8,212,653 B1 | 7/2012 | Goldstein et al. |
| 8,237,558 B2 | 8/2012 | Seyed et al. |
| 8,240,517 B1 | 8/2012 | Stob et al. |
| 8,249,295 B2 | 8/2012 | Johnson |
| 8,258,965 B2 | 9/2012 | Reeder et al. |
| 8,261,950 B2 * | 9/2012 | Cittadino .......... A47K 5/1202 222/325 |
| 8,264,343 B2 | 9/2012 | Snodgrass |
| 8,279,063 B2 | 10/2012 | Wohltjen |
| 8,294,585 B2 | 10/2012 | Barnhill |
| 8,308,027 B2 * | 11/2012 | Law .......... A47K 5/12 222/154 |
| 8,342,365 B2 | 1/2013 | Snodgrass |
| 8,344,893 B1 | 1/2013 | Drammeh |
| 8,350,706 B2 | 1/2013 | Wegelin et al. |
| 8,368,544 B2 | 2/2013 | Wildman et al. |
| 8,372,207 B1 | 2/2013 | Shields |
| 8,395,515 B2 | 3/2013 | Tokhtuev et al. |
| 8,400,309 B2 | 3/2013 | Glenn et al. |
| 8,427,323 B2 | 4/2013 | Alper et al. |
| 8,482,406 B2 | 7/2013 | Snodgrass |
| 8,502,680 B2 | 8/2013 | Tokhtuev et al. |
| 8,502,681 B2 | 8/2013 | Bolling et al. |
| 8,511,512 B2 | 8/2013 | Carlson et al. |

(56) References Cited

U.S. PATENT DOCUMENTS

| | | | |
|---|---|---|---|
| 8,525,666 B2 | 9/2013 | Melker et al. | |
| 8,547,220 B1 | 10/2013 | Dempsey et al. | |
| 8,558,660 B2 | 10/2013 | Nix et al. | |
| 8,558,701 B2 | 10/2013 | Archer et al. | |
| 8,564,431 B2 | 10/2013 | Snodgrass | |
| D693,140 S | 11/2013 | Rospierski | |
| 8,587,437 B2 | 11/2013 | Kyle et al. | |
| 8,598,996 B2 | 12/2013 | Wildman et al. | |
| 8,633,806 B2 | 1/2014 | Amir | |
| 8,633,816 B2 | 1/2014 | Snodgrass et al. | |
| 8,639,527 B2 | 1/2014 | Rensvold et al. | |
| 8,646,656 B2 | 2/2014 | Johnson | |
| 8,648,724 B2 | 2/2014 | Forsberg et al. | |
| 8,651,328 B2 * | 2/2014 | Cittadino | A47K 5/1202 250/482.1 |
| 8,668,145 B2 | 3/2014 | Tessier | |
| 8,674,840 B2 | 3/2014 | Snodgrass | |
| 8,698,637 B2 | 4/2014 | Raichman | |
| 8,712,587 B2 * | 4/2014 | Handfield | G16H 40/67 221/241 |
| 8,720,107 B1 * | 5/2014 | Vickery | A01M 1/106 43/107 |
| 8,776,817 B2 | 7/2014 | Sawaski et al. | |
| 8,783,511 B2 | 7/2014 | Snodgrass | |
| 8,786,429 B2 | 7/2014 | Li et al. | |
| 8,816,860 B2 | 8/2014 | Ophardt et al. | |
| 8,823,525 B2 | 9/2014 | Cartner et al. | |
| 8,842,406 B2 | 9/2014 | Tseng et al. | |
| 8,847,752 B2 | 9/2014 | Wegelin et al. | |
| 8,872,665 B2 | 10/2014 | Snodgrass | |
| 8,903,416 B1 | 12/2014 | Perkins et al. | |
| 8,963,721 B2 | 2/2015 | Harris et al. | |
| 8,963,723 B2 | 2/2015 | Snodgrass | |
| 8,976,031 B2 | 3/2015 | Ophardt | |
| 8,988,228 B2 | 3/2015 | Iseri et al. | |
| 8,990,098 B2 | 3/2015 | Swart et al. | |
| 8,994,537 B2 | 3/2015 | Pokrajac | |
| 8,999,261 B2 | 4/2015 | Benedetto | |
| 9,000,930 B2 | 4/2015 | Pelland et al. | |
| 9,007,209 B1 * | 4/2015 | Ehrman | G06Q 10/08 340/568.1 |
| 9,007,936 B2 | 4/2015 | Gaylard et al. | |
| 9,013,312 B2 | 4/2015 | Bolling | |
| 9,047,755 B2 | 6/2015 | Bonner | |
| 9,060,655 B2 | 6/2015 | Iseri et al. | |
| 9,076,044 B2 | 7/2015 | Dryer et al. | |
| 9,111,435 B2 | 8/2015 | Gips et al. | |
| 9,117,361 B1 | 8/2015 | Hennigan et al. | |
| 9,123,233 B2 | 9/2015 | Hermann | |
| 9,159,216 B2 | 10/2015 | Limbert et al. | |
| 9,218,734 B2 | 12/2015 | Wallace et al. | |
| 9,235,977 B2 | 1/2016 | Deutsch | |
| 9,239,361 B2 | 1/2016 | Long | |
| 9,262,905 B2 | 2/2016 | Wegelin et al. | |
| 9,271,611 B2 | 3/2016 | Stratmann | |
| 9,271,612 B2 | 3/2016 | Miller | |
| 9,299,238 B1 * | 3/2016 | Ahmad | G06F 3/0482 |
| 9,311,809 B2 | 4/2016 | Diaz | |
| 9,317,817 B2 | 4/2016 | Barsky | |
| 9,328,490 B2 | 5/2016 | Bayley et al. | |
| 9,349,274 B2 | 5/2016 | Wegelin et al. | |
| 9,373,242 B1 | 6/2016 | Conrad et al. | |
| 9,395,515 B2 | 7/2016 | Miyano | |
| 9,437,103 B2 | 9/2016 | Ophardt | |
| 9,472,089 B2 | 10/2016 | Alhazme | |
| 9,478,118 B2 | 10/2016 | Keown et al. | |
| 9,497,428 B2 | 11/2016 | Gaisser et al. | |
| 9,524,480 B2 | 12/2016 | Christensen | |
| 9,524,632 B2 | 12/2016 | Moore | |
| 9,526,380 B2 | 12/2016 | Hamilton et al. | |
| 9,536,415 B2 | 1/2017 | De Luca et al. | |
| 9,561,517 B2 * | 2/2017 | Wertheim | A47K 5/1202 |
| 9,613,519 B2 | 4/2017 | Iseri et al. | |
| 9,626,650 B2 * | 4/2017 | Hwang | G06Q 30/00 |
| 9,628,434 B2 * | 4/2017 | Laidlaw | G10L 15/22 |
| 9,633,543 B2 * | 4/2017 | Wegelin | G08B 21/245 |
| 9,633,544 B2 | 4/2017 | Wegelin et al. | |
| 9,633,545 B2 | 4/2017 | Wegelin et al. | |
| 9,640,059 B2 | 5/2017 | Hyland | |
| 9,702,961 B2 | 7/2017 | Shields | |
| 9,809,439 B2 * | 11/2017 | Falco, III | B67D 1/0888 |
| 9,824,569 B2 | 11/2017 | Snodgrass | |
| 9,830,764 B1 * | 11/2017 | Murphy | G07F 9/023 |
| 9,881,485 B2 | 1/2018 | Hajdenberg | |
| 9,920,553 B2 * | 3/2018 | Limbert | E05B 65/06 |
| 9,953,140 B2 * | 4/2018 | McLean | G16H 20/13 |
| 10,008,098 B2 | 6/2018 | Ophardt | |
| 10,022,023 B2 * | 7/2018 | Santoro | B05B 11/0044 |
| 10,123,661 B2 * | 11/2018 | Wertheim | A47K 5/1202 |
| 10,226,037 B2 * | 3/2019 | States, III | A01M 1/2038 |
| 10,235,865 B2 * | 3/2019 | Thyroff | G06F 3/167 |
| 10,373,477 B1 * | 8/2019 | Bonner | A47K 5/12 |
| 10,395,192 B2 * | 8/2019 | Becker | G07F 9/026 |
| 10,490,057 B1 | 11/2019 | Malina et al. | |
| 10,529,219 B2 | 1/2020 | Herdt et al. | |
| 10,665,084 B1 * | 5/2020 | Peck | G08B 21/245 |
| 10,679,236 B2 * | 6/2020 | Becker | G06Q 30/0233 |
| 10,714,216 B1 | 7/2020 | Hardman et al. | |
| 10,732,021 B2 * | 8/2020 | Moore | G01G 13/248 |
| 10,743,720 B2 * | 8/2020 | Wertheim | A47K 5/12 |
| 10,743,721 B2 * | 8/2020 | Wertheim | A47K 5/1202 |
| 10,762,764 B1 * | 9/2020 | King | A61B 5/0077 |
| 10,978,200 B1 | 4/2021 | Hardman et al. | |
| 11,025,720 B2 * | 6/2021 | Skaaksrud | B64D 9/003 |
| 11,127,278 B2 * | 9/2021 | Freedman | G16H 40/20 |
| 11,272,815 B2 * | 3/2022 | Rospierski | G08B 21/245 |
| 11,504,011 B1 * | 11/2022 | Jain | G06N 5/04 |
| 11,531,937 B2 * | 12/2022 | Becker | G06Q 10/06 |
| 11,903,537 B2 | 2/2024 | Rospierski et al. | |
| 2001/0023841 A1 | 9/2001 | Zimmerman et al. | |
| 2001/0023878 A1 * | 9/2001 | Irwin | B65D 83/0841 221/92 |
| 2001/0028308 A1 | 10/2001 | De La Huerga | |
| 2001/0039501 A1 | 11/2001 | Crevel et al. | |
| 2001/0047214 A1 | 11/2001 | Cocking et al. | |
| 2001/0053939 A1 | 12/2001 | Crevel et al. | |
| 2001/0054038 A1 | 12/2001 | Crevel et al. | |
| 2001/0054626 A1 | 12/2001 | Bethune et al. | |
| 2002/0000449 A1 * | 1/2002 | Armstrong | A47K 5/1217 222/52 |
| 2002/0005414 A1 * | 1/2002 | DeKoning | A47K 5/12 222/181.3 |
| 2002/0014496 A1 | 2/2002 | Cline et al. | |
| 2002/0019709 A1 * | 2/2002 | Segal | G07C 3/10 702/45 |
| 2002/0050006 A1 | 5/2002 | Saraya | |
| 2002/0096537 A1 | 7/2002 | Gardner | |
| 2002/0100676 A1 | 8/2002 | Janniere | |
| 2002/0103671 A1 | 8/2002 | Pederson et al. | |
| 2002/0107744 A1 | 8/2002 | Rosenberg et al. | |
| 2002/0109761 A1 * | 8/2002 | Shimizu | B41J 2/1755 347/50 |
| 2002/0117187 A1 | 8/2002 | Helminger | |
| 2002/0132343 A1 | 9/2002 | Lum | |
| 2002/0135486 A1 | 9/2002 | Brohagen et al. | |
| 2002/0145523 A1 | 10/2002 | Robaey | |
| 2002/0168216 A1 | 11/2002 | Policicchio et al. | |
| 2002/0175182 A1 | 11/2002 | Matthews | |
| 2002/0183979 A1 | 12/2002 | Wildman | |
| 2003/0030562 A1 | 2/2003 | Lane et al. | |
| 2003/0033396 A1 | 2/2003 | Mccall | |
| 2003/0043688 A1 | 3/2003 | Peterson et al. | |
| 2003/0065536 A1 | 4/2003 | Hansen et al. | |
| 2003/0074222 A1 | 4/2003 | Rosow et al. | |
| 2003/0109057 A1 | 6/2003 | Dicesare et al. | |
| 2003/0121561 A1 | 7/2003 | Wagner et al. | |
| 2003/0155035 A1 | 8/2003 | Ichikawa et al. | |
| 2003/0182180 A1 | 9/2003 | Zarrow | |
| 2004/0001009 A1 | 1/2004 | Winings et al. | |
| 2004/0015269 A1 | 1/2004 | Jungmann et al. | |
| 2004/0018839 A1 | 1/2004 | Andric et al. | |
| 2004/0028608 A1 | 2/2004 | Saul et al. | |
| 2004/0049369 A1 | 3/2004 | Konicek et al. | |
| 2004/0075347 A1 | 4/2004 | Biskup et al. | |

(56) References Cited

U.S. PATENT DOCUMENTS

| | | |
|---|---|---|
| 2004/0088076 A1 | 5/2004 | Gardner |
| 2004/0090333 A1 | 5/2004 | Wildman et al. |
| 2004/0148196 A1 | 7/2004 | Kalies |
| 2004/0150527 A1 | 8/2004 | Harper et al. |
| 2004/0162850 A1 | 8/2004 | Sanville et al. |
| 2004/0217197 A1* | 11/2004 | Mazooji ............... A47K 3/281 239/302 |
| 2004/0220844 A1 | 11/2004 | Sanville et al. |
| 2004/0226956 A1 | 11/2004 | Brooks |
| 2004/0226959 A1 | 11/2004 | Mehus et al. |
| 2004/0226962 A1* | 11/2004 | Mazursky ............ A47K 5/1217 222/64 |
| 2004/0229959 A1 | 11/2004 | Reddy et al. |
| 2004/0230339 A1 | 11/2004 | Maser et al. |
| 2005/0065644 A1 | 3/2005 | Gardner |
| 2005/0072793 A1 | 4/2005 | Mehus et al. |
| 2005/0086341 A1 | 4/2005 | Enga et al. |
| 2005/0102167 A1 | 5/2005 | Kapoor |
| 2005/0134465 A1 | 6/2005 | Rice et al. |
| 2005/0134466 A1 | 6/2005 | Tirkel |
| 2005/0149341 A1 | 7/2005 | Eguchi et al. |
| 2005/0171634 A1 | 8/2005 | York et al. |
| 2005/0222889 A1 | 10/2005 | Lai et al. |
| 2005/0248461 A1 | 11/2005 | Lane et al. |
| 2006/0067545 A1 | 3/2006 | Lewis et al. |
| 2006/0067546 A1 | 3/2006 | Lewis et al. |
| 2006/0071799 A1 | 4/2006 | Verdiramo |
| 2006/0104245 A1 | 5/2006 | Narayanaswami et al. |
| 2006/0132316 A1 | 6/2006 | Wildman et al. |
| 2006/0139449 A1 | 6/2006 | Cheng et al. |
| 2006/0140703 A1 | 6/2006 | Sacks |
| 2006/0154642 A1 | 7/2006 | Scannell, Jr. |
| 2006/0156415 A1 | 7/2006 | Rubinstein et al. |
| 2006/0191068 A1 | 8/2006 | Vlahos et al. |
| 2006/0223731 A1 | 10/2006 | Carling |
| 2006/0229821 A1 | 10/2006 | Brossette et al. |
| 2006/0240397 A1 | 10/2006 | Lynn et al. |
| 2006/0272361 A1* | 12/2006 | Snodgrass ............ G08B 21/245 68/19 |
| 2006/0273915 A1* | 12/2006 | Snodgrass ............ G08B 21/245 222/52 |
| 2006/0277065 A1 | 12/2006 | Guten et al. |
| 2007/0008146 A1 | 1/2007 | Taylor et al. |
| 2007/0008147 A1 | 1/2007 | Bolling |
| 2007/0008149 A1 | 1/2007 | Bolling |
| 2007/0016466 A1 | 1/2007 | Taylor |
| 2007/0020212 A1 | 1/2007 | Bernal et al. |
| 2007/0029962 A1 | 2/2007 | Saeki |
| 2007/0044819 A1 | 3/2007 | Chan et al. |
| 2007/0055483 A1 | 3/2007 | Lee et al. |
| 2007/0056091 A1 | 3/2007 | Bolton et al. |
| 2007/0069884 A1 | 3/2007 | Waxman |
| 2007/0096930 A1 | 5/2007 | Cardoso |
| 2007/0135866 A1 | 6/2007 | Baker et al. |
| 2007/0182581 A1 | 8/2007 | Elwell |
| 2007/0198067 A1 | 8/2007 | Van Den Heuvel et al. |
| 2007/0205861 A1 | 9/2007 | Nair et al. |
| 2007/0213877 A1 | 9/2007 | Hart et al. |
| 2007/0222599 A1 | 9/2007 | Coveley et al. |
| 2007/0228065 A1* | 10/2007 | Anderson .......... B65D 83/0409 221/152 |
| 2007/0229288 A1 | 10/2007 | Ogrin et al. |
| 2007/0247316 A1 | 10/2007 | Wildman et al. |
| 2007/0257803 A1 | 11/2007 | Munro et al. |
| 2007/0285277 A1 | 12/2007 | Scott et al. |
| 2007/0290865 A1 | 12/2007 | Lynn et al. |
| 2008/0001763 A1 | 1/2008 | Raja et al. |
| 2008/0019489 A1 | 1/2008 | Lynn |
| 2008/0019490 A1 | 1/2008 | Lynn |
| 2008/0046278 A1 | 2/2008 | Sanville et al. |
| 2008/0084315 A1 | 4/2008 | Pittz |
| 2008/0087719 A1 | 4/2008 | Sahud |
| 2008/0095677 A1 | 4/2008 | Mcsherry et al. |
| 2008/0100441 A1 | 5/2008 | Prodanovich et al. |
| 2008/0103636 A1 | 5/2008 | Glenn et al. |
| 2008/0131332 A1 | 6/2008 | Nguyen et al. |
| 2008/0136649 A1 | 6/2008 | Van De Hey |
| 2008/0177155 A1 | 7/2008 | Hansen et al. |
| 2008/0181142 A1 | 7/2008 | Garrett et al. |
| 2008/0185540 A1 | 8/2008 | Turner et al. |
| 2008/0189142 A1 | 8/2008 | Vines et al. |
| 2008/0193631 A1 | 8/2008 | Kanamori et al. |
| 2008/0246599 A1 | 10/2008 | Hufton et al. |
| 2008/0262097 A1 | 10/2008 | Eady et al. |
| 2008/0266113 A1 | 10/2008 | Kennish et al. |
| 2008/0267408 A1 | 10/2008 | Hsieh |
| 2008/0271928 A1 | 11/2008 | Mehus et al. |
| 2008/0280380 A1 | 11/2008 | Dietz et al. |
| 2008/0283145 A1 | 11/2008 | Maxwell |
| 2008/0290112 A1 | 11/2008 | Lynn |
| 2008/0303658 A1 | 12/2008 | Melker et al. |
| 2009/0002644 A1 | 1/2009 | Christensen et al. |
| 2009/0019552 A1 | 1/2009 | Mclaughlin et al. |
| 2009/0030721 A1 | 1/2009 | Garcia et al. |
| 2009/0037026 A1 | 2/2009 | Sostaric et al. |
| 2009/0049610 A1 | 2/2009 | Heimbrock et al. |
| 2009/0051545 A1 | 2/2009 | Koblasz |
| 2009/0068116 A1 | 3/2009 | Arndt |
| 2009/0084407 A1 | 4/2009 | Glenn et al. |
| 2009/0090564 A1 | 4/2009 | Kresina |
| 2009/0091458 A1 | 4/2009 | Deutsch |
| 2009/0102681 A1 | 4/2009 | Brennan, Jr. et al. |
| 2009/0112360 A1 | 4/2009 | Berg |
| 2009/0112541 A1 | 4/2009 | Anderson et al. |
| 2009/0112630 A1 | 4/2009 | Collins, Jr. et al. |
| 2009/0119142 A1 | 5/2009 | Yenni et al. |
| 2009/0125424 A1 | 5/2009 | Wegelin |
| 2009/0127282 A1 | 5/2009 | Reynolds et al. |
| 2009/0138303 A1 | 5/2009 | Seshadri |
| 2009/0145925 A1 | 6/2009 | Wegelin |
| 2009/0148342 A1 | 6/2009 | Bromberg et al. |
| 2009/0166378 A1 | 7/2009 | Stilley |
| 2009/0171502 A1 | 7/2009 | Freidin |
| 2009/0195385 A1* | 8/2009 | Huang ................... G16H 40/20 340/572.1 |
| 2009/0204256 A1 | 8/2009 | Wegelin |
| 2009/0219131 A1 | 9/2009 | Barnett et al. |
| 2009/0219172 A1 | 9/2009 | Wilbrod |
| 2009/0224907 A1 | 9/2009 | Sinha et al. |
| 2009/0224924 A1* | 9/2009 | Thorp ................... G16H 40/20 340/573.1 |
| 2009/0266842 A1 | 10/2009 | Snodgrass |
| 2009/0267776 A1 | 10/2009 | Glenn et al. |
| 2009/0272405 A1 | 11/2009 | Barnhill et al. |
| 2009/0273477 A1 | 11/2009 | Barnhill |
| 2009/0276239 A1 | 11/2009 | Swart et al. |
| 2009/0294469 A1 | 12/2009 | Poulain et al. |
| 2009/0299787 A1* | 12/2009 | Barnhill ............... G08B 21/245 434/365 |
| 2009/0301523 A1 | 12/2009 | Barnhill et al. |
| 2009/0324792 A1* | 12/2009 | Verhoeven .......... B01F 27/2712 366/195 |
| 2010/0084486 A1 | 4/2010 | Kim |
| 2010/0094581 A1 | 4/2010 | Cagle |
| 2010/0097224 A1 | 4/2010 | Prodanovich et al. |
| 2010/0117823 A1 | 5/2010 | Wholtjen |
| 2010/0117836 A1 | 5/2010 | Seyed Momen et al. |
| 2010/0134296 A1 | 6/2010 | Hwang |
| 2010/0153374 A1 | 6/2010 | Leblond et al. |
| 2010/0173581 A1 | 7/2010 | Dolan |
| 2010/0188228 A1 | 7/2010 | Hyland |
| 2010/0233020 A1 | 9/2010 | Klaassen et al. |
| 2010/0238021 A1 | 9/2010 | Harris |
| 2010/0274640 A1 | 10/2010 | Morey et al. |
| 2010/0315243 A1 | 12/2010 | Tokhtuev et al. |
| 2010/0315244 A1* | 12/2010 | Tokhtuev ............ G08B 21/245 340/603 |
| 2010/0328076 A1* | 12/2010 | Kyle ..................... G16H 40/20 340/573.1 |
| 2010/0332022 A1 | 12/2010 | Wegelin et al. |
| 2011/0008880 A1 | 1/2011 | Uehata et al. |
| 2011/0016964 A1 | 1/2011 | Strom |
| 2011/0023459 A1 | 2/2011 | Nieuwstadt et al. |

(56) References Cited

U.S. PATENT DOCUMENTS

| | | |
|---|---|---|
| 2011/0063106 A1 | 3/2011 | Snodgrass |
| 2011/0088809 A1 | 4/2011 | Lin |
| 2011/0093313 A1 | 4/2011 | Leblond et al. |
| 2011/0108578 A1* | 5/2011 | Wegelin ............... A47K 5/1217 222/372 |
| 2011/0121974 A1 | 5/2011 | Tenarvitz et al. |
| 2011/0169645 A1 | 7/2011 | Cartner et al. |
| 2011/0169646 A1 | 7/2011 | Raichman |
| 2011/0180564 A1 | 7/2011 | Jones et al. |
| 2011/0193703 A1 | 8/2011 | Payton et al. |
| 2011/0196720 A1 | 8/2011 | Guten et al. |
| 2011/0234598 A1 | 9/2011 | Scarola et al. |
| 2011/0260872 A1 | 10/2011 | Kennish et al. |
| 2011/0273298 A1 | 11/2011 | Snodgrass et al. |
| 2011/0286326 A1 | 11/2011 | Awano |
| 2011/0291841 A1 | 12/2011 | Hollock et al. |
| 2011/0296664 A1 | 12/2011 | Minard et al. |
| 2011/0316695 A1 | 12/2011 | Li et al. |
| 2011/0316701 A1 | 12/2011 | Alper et al. |
| 2011/0316703 A1 | 12/2011 | Butler et al. |
| 2012/0024890 A1 | 2/2012 | Ota et al. |
| 2012/0047988 A1 | 3/2012 | Mehus et al. |
| 2012/0062382 A1 | 3/2012 | Taneff |
| 2012/0112906 A1* | 5/2012 | Borke ................... G16H 40/20 340/539.13 |
| 2012/0112914 A1 | 5/2012 | Wegelin et al. |
| 2012/0168459 A1 | 7/2012 | D'Onofrio |
| 2012/0194338 A1* | 8/2012 | Snodgrass ............ G08B 21/245 340/539.12 |
| 2012/0212344 A1 | 8/2012 | Forsberg et al. |
| 2012/0218106 A1* | 8/2012 | Zaima .................... B05B 12/02 340/540 |
| 2012/0245729 A1 | 9/2012 | Wegelin et al. |
| 2012/0256742 A1 | 10/2012 | Snodgrass et al. |
| 2012/0274468 A1 | 11/2012 | Wegelin et al. |
| 2012/0299731 A1* | 11/2012 | Triener ................ A01K 29/005 702/19 |
| 2012/0310664 A1 | 12/2012 | Long et al. |
| 2012/0329438 A1 | 12/2012 | Snodgrass |
| 2013/0037569 A1* | 2/2013 | Kelly ................... B05B 11/1057 141/2 |
| 2013/0045685 A1 | 2/2013 | Kiani |
| 2013/0075346 A1 | 3/2013 | Rumberger et al. |
| 2013/0076514 A1 | 3/2013 | Wegelin et al. |
| 2013/0091631 A1 | 4/2013 | Hayes et al. |
| 2013/0098941 A1* | 4/2013 | Wegelin ............... A47K 5/1205 222/23 |
| 2013/0099900 A1 | 4/2013 | Pulvermacher |
| 2013/0113931 A1 | 5/2013 | Alper |
| 2013/0120120 A1 | 5/2013 | Long et al. |
| 2013/0133762 A1 | 5/2013 | Snodgrass |
| 2013/0221076 A1 | 8/2013 | Tran et al. |
| 2013/0224076 A1 | 8/2013 | Hansmann et al. |
| 2013/0229276 A1 | 9/2013 | Hunter |
| 2013/0234855 A1 | 9/2013 | Knighton |
| 2013/0257615 A1 | 10/2013 | Iseri et al. |
| 2013/0261795 A1 | 10/2013 | Long et al. |
| 2013/0264355 A1 | 10/2013 | Jodoin |
| 2013/0285814 A1 | 10/2013 | Snodgrass |
| 2013/0290016 A1 | 10/2013 | Alper et al. |
| 2013/0292407 A1 | 11/2013 | Beavis et al. |
| 2013/0306105 A1 | 11/2013 | Battah |
| 2013/0332184 A1 | 12/2013 | Burnham et al. |
| 2013/0333184 A1 | 12/2013 | Couture et al. |
| 2013/0342349 A1 | 12/2013 | Cruz |
| 2014/0009292 A1 | 1/2014 | Long et al. |
| 2014/0015670 A1 | 1/2014 | Wegelin et al. |
| 2014/0027470 A1* | 1/2014 | Pelfrey ................. B65D 21/086 222/105 |
| 2014/0070950 A1 | 3/2014 | Snodgrass |
| 2014/0081653 A1 | 3/2014 | Davis et al. |
| 2014/0108039 A1 | 4/2014 | Rensvold et al. |
| 2014/0158714 A1* | 6/2014 | Snodgrass ............ A47K 5/1217 222/183 |
| 2014/0180713 A1 | 6/2014 | Tenarvitz et al. |
| 2014/0210620 A1 | 7/2014 | Snodgrass |
| 2014/0214449 A1 | 7/2014 | Long et al. |
| 2014/0231455 A1 | 8/2014 | Jersey et al. |
| 2014/0242562 A1 | 8/2014 | Mcsterling et al. |
| 2014/0253334 A1 | 9/2014 | Hanlin et al. |
| 2014/0253336 A1* | 9/2014 | Ophardt ............... A47K 5/1217 340/573.1 |
| 2014/0279603 A1 | 9/2014 | Ortiz et al. |
| 2014/0311239 A1 | 10/2014 | Marjanovic et al. |
| 2014/0320289 A1 | 10/2014 | Raichman |
| 2014/0327545 A1 | 11/2014 | Bolling et al. |
| 2014/0333433 A1 | 11/2014 | Li et al. |
| 2014/0333744 A1* | 11/2014 | Baym .................. G08B 21/245 348/77 |
| 2014/0347185 A1 | 11/2014 | Smith et al. |
| 2014/0361898 A1 | 12/2014 | Wegelin et al. |
| 2014/0366264 A1 | 12/2014 | Ciavarella et al. |
| 2014/0368320 A1 | 12/2014 | Hyland |
| 2015/0022361 A1* | 1/2015 | Gaisser ............. H01L 27/14627 340/573.1 |
| 2015/0035678 A1 | 2/2015 | Long |
| 2015/0048940 A1 | 2/2015 | Keown et al. |
| 2015/0061867 A1 | 3/2015 | Engelhard et al. |
| 2015/0070174 A1 | 3/2015 | Douglas |
| 2015/0101121 A1 | 4/2015 | Burgo, Sr. et al. |
| 2015/0127365 A1 | 5/2015 | Rizvi et al. |
| 2015/0134354 A1 | 5/2015 | Alper et al. |
| 2015/0134357 A1* | 5/2015 | Davis .................. G06Q 30/018 705/2 |
| 2015/0170502 A1* | 6/2015 | Harris ................. G08B 21/245 340/573.1 |
| 2015/0179047 A1 | 6/2015 | Wallace et al. |
| 2015/0194043 A1 | 7/2015 | Dunn et al. |
| 2015/0199883 A1 | 7/2015 | Hartley et al. |
| 2015/0221208 A1 | 8/2015 | Knighton et al. |
| 2015/0278456 A1 | 10/2015 | Bermudez Rodriguez et al. |
| 2015/0308149 A1 | 10/2015 | Oshmyansky et al. |
| 2015/0313422 A1 | 11/2015 | Ophardt et al. |
| 2015/0363566 A1* | 12/2015 | Johnson ................ G16H 50/30 705/3 |
| 2015/0366411 A1 | 12/2015 | Yang et al. |
| 2016/0026837 A1* | 1/2016 | Good ..................... G16H 40/20 340/539.13 |
| 2016/0042635 A1 | 2/2016 | Rosebraugh et al. |
| 2016/0068383 A1* | 3/2016 | Falco, III ............. B67D 1/0888 222/25 |
| 2016/0093195 A1 | 3/2016 | Ophardt |
| 2016/0128520 A1 | 5/2016 | Wegelin et al. |
| 2016/0140830 A1 | 5/2016 | Hathorn |
| 2016/0152430 A1* | 6/2016 | Ray ........................ A61B 90/98 242/563 |
| 2016/0174022 A1* | 6/2016 | Nhu ........................ H04W 4/70 455/41.2 |
| 2016/0179089 A1 | 6/2016 | Stratmann |
| 2016/0240070 A1 | 8/2016 | Wegelin et al. |
| 2016/0247381 A1 | 8/2016 | Rensvold et al. |
| 2016/0249774 A1 | 9/2016 | Ophardt et al. |
| 2016/0267772 A1 | 9/2016 | Iseri et al. |
| 2016/0278558 A1* | 9/2016 | Ansari .................. A47G 29/121 |
| 2016/0292992 A1 | 10/2016 | Ortiz et al. |
| 2016/0309967 A1* | 10/2016 | Pelfrey ................. A47K 5/1217 |
| 2016/0331894 A1* | 11/2016 | Harmon ............... G08B 21/182 |
| 2017/0004287 A1 | 1/2017 | O'toole |
| 2017/0098376 A1 | 4/2017 | Hood et al. |
| 2017/0112331 A1* | 4/2017 | Toh ....................... A47K 5/1211 |
| 2017/0120274 A1 | 5/2017 | Schultz ................ F16K 27/0209 |
| 2017/0134887 A1* | 5/2017 | Wegelin ................ G06Q 10/06 |
| 2017/0256155 A1* | 9/2017 | Sengstaken, Jr. .. G06K 19/0723 |
| 2017/0287313 A1* | 10/2017 | Park ......................... A61B 5/002 |
| 2018/0024202 A1* | 1/2018 | Erickson .............. G01R 31/3835 340/636.15 |
| 2018/0111145 A1* | 4/2018 | Ophardt ................ B05B 11/0054 |
| 2018/0151054 A1* | 5/2018 | Pi ......................... G08B 21/245 |
| 2018/0255981 A1 | 9/2018 | Rospierski et al. |
| 2018/0310780 A1* | 11/2018 | Mahaffey .............. G01H 17/00 |
| 2018/0368627 A1* | 12/2018 | Ghazi ................... A47K 5/1217 |
| 2019/0063980 A1* | 2/2019 | Kobs ....................... A47K 5/16 |

(56) References Cited

U.S. PATENT DOCUMENTS

| | | | |
|---|---|---|---|
| 2019/0171244 A1* | 6/2019 | Wegelin | H03K 17/941 |
| 2019/0172336 A1* | 6/2019 | Haidegger | A61L 2/28 |
| 2019/0228640 A1 | 7/2019 | Freedman et al. | |
| 2019/0250653 A1* | 8/2019 | Conlon | G06Q 10/0832 |
| 2020/0094091 A1* | 3/2020 | Skaaksrud | G01T 1/17 |
| 2020/0100627 A1* | 4/2020 | Ophardt | A47K 5/12 |
| 2020/0138246 A1* | 5/2020 | Wegelin | G01J 5/027 |
| 2020/0167534 A1* | 5/2020 | Elizondo, II | G06K 7/0008 |
| 2020/0173719 A1* | 6/2020 | Jaakkola | G01N 33/0063 |
| 2020/0193797 A1* | 6/2020 | Lindstrom | G16H 40/20 |
| 2020/0193798 A1* | 6/2020 | Lindstrom | G09B 19/003 |
| 2020/0205055 A1 | 6/2020 | Snodgrass | |
| 2021/0012640 A1 | 1/2021 | Tokhtuev et al. | |
| 2022/0142415 A1 | 5/2022 | Rospierski et al. | |
| 2022/0310269 A1* | 9/2022 | Bekanich | A61B 5/746 |

FOREIGN PATENT DOCUMENTS

| | | |
|---|---|---|
| AU | 2015202637 A1 | 6/2015 |
| AU | 2015258158 A1 | 12/2015 |
| AU | 2015275337 A1 | 1/2016 |
| AU | 2013378514 B2 | 11/2017 |
| BR | 102012030486 A2 | 9/2014 |
| BR | 112019018376 B1 | 2/2024 |
| CA | 2605412 A1 | 12/2006 |
| CA | 2592814 A1 | 12/2007 |
| CA | 2674654 A1 | 10/2009 |
| CA | 2776280 A1 | 11/2013 |
| CA | 2780411 A1 | 12/2013 |
| CA | 2807337 A1 | 8/2014 |
| CA | 2914864 A1 | 6/2016 |
| CN | 2354482 Y | 12/1999 |
| CN | 1181415 C | 12/2004 |
| CN | 1938724 A | 3/2007 |
| CN | 100340935 C | 10/2007 |
| CN | 101592510 A | 12/2009 |
| CN | 201974318 U | 9/2011 |
| CN | 202677403 U | 1/2013 |
| CN | 103169409 A | 6/2013 |
| CN | 103198628 A | 7/2013 |
| CN | 203153706 U | 8/2013 |
| CN | 203325033 U | 12/2013 |
| CN | 103617349 A | 3/2014 |
| CN | 204218783 U | 3/2015 |
| CN | 104615091 A | 5/2015 |
| CN | 104622348 A | 5/2015 |
| CN | 204520455 U | 8/2015 |
| CN | 105139320 A | 12/2015 |
| CN | 105164737 A | 12/2015 |
| CN | 204990347 U | 1/2016 |
| CN | 101911108 B | 2/2016 |
| CN | 205197874 U | 5/2016 |
| CN | 106154902 A | 11/2016 |
| DE | 69708606 T2 | 8/2002 |
| DE | 10157975 A1 | 6/2003 |
| DE | 36617795 T2 | 7/2005 |
| DE | 19882120 B4 | 10/2010 |
| DE | 102012105365 A1 | 12/2013 |
| DK | 2015665 T3 | 11/2009 |
| EP | 0921506 A1 | 6/1999 |
| EP | 0940110 A1 | 9/1999 |
| EP | 0927535 A3 | 7/2000 |
| EP | 1049998 A2 | 11/2000 |
| EP | 1099400 A2 | 5/2001 |
| EP | 1121500 A1 | 8/2001 |
| EP | 1201172 A2 | 5/2002 |
| EP | 1245016 A1 | 10/2002 |
| EP | 1390204 B1 | 12/2004 |
| EP | EP1034132 B1 | 8/2005 |
| EP | 1483728 B1 | 10/2006 |
| EP | 1791077 A2 | 5/2007 |
| EP | 1794727 A1 | 6/2007 |
| EP | 1872802 A1 | 1/2008 |
| EP | 1872892 A1 | 1/2008 |
| EP | 1913892 A2 | 4/2008 |
| EP | 1978703 A1 | 10/2008 |
| EP | 2012277 A1 | 1/2009 |
| EP | 2223642 A2 | 9/2010 |
| EP | 2509017 A2 | 10/2012 |
| EP | 2511889 A2 | 10/2012 |
| EP | 2637540 A2 | 9/2013 |
| EP | 2860716 A1 | 4/2015 |
| EP | 2956918 A1 | 12/2015 |
| EP | 3581897 B1 | 9/2020 |
| FR | 2872315 A1 | 12/2005 |
| FR | 2997779 A1 | 5/2014 |
| GB | 2052251 A | 1/1981 |
| GB | 2137749 A | 10/1984 |
| GB | 2217013 A | 10/1989 |
| GB | 2298851 A | 9/1996 |
| GB | 2299405 A | 10/1996 |
| GB | 2324397 A | 10/1998 |
| GB | 2337327 A | 11/1999 |
| GB | 2340647 A | 2/2000 |
| GB | 2394654 A | 5/2004 |
| GB | 2417810 A | 3/2006 |
| GB | 2417811 A | 3/2006 |
| GB | 2425388 A | 10/2006 |
| GB | 2436793 A | 10/2007 |
| GB | 2437555 A | 10/2007 |
| GB | 2439306 A | 12/2007 |
| GB | 2439457 A | 12/2007 |
| GB | 2446871 A | 8/2008 |
| GB | 2452189 A | 2/2009 |
| GB | 2457930 A | 9/2009 |
| GB | 2458118 A | 9/2009 |
| GB | 2469482 A | 10/2010 |
| GB | 2474317 A | 4/2011 |
| GB | 2486767 A | 6/2012 |
| GB | 2537179 A | 10/2016 |
| JP | H01219439 A | 9/1989 |
| JP | H06226068 A | 8/1994 |
| JP | H0966995 A | 3/1997 |
| JP | H0966999 A | 3/1997 |
| JP | H10309540 A | 11/1998 |
| JP | H11332961 A | 12/1999 |
| JP | 2001292918 A | 10/2001 |
| JP | 3281375 B2 | 5/2002 |
| JP | 2002197559 A | 7/2002 |
| JP | 2003105819 A | 4/2003 |
| JP | 2003122823 A | 4/2003 |
| JP | 2005218999 A | 8/2005 |
| JP | 2006132277 A | 5/2006 |
| JP | 2006198318 A | 8/2006 |
| JP | 2008027436 A | 2/2008 |
| JP | 2009282442 A | 12/2009 |
| JP | 4523219 B2 | 8/2010 |
| JP | 2013017631 A | 1/2013 |
| JP | 2013180046 A | 9/2013 |
| JP | 2013187557 A | 9/2013 |
| JP | 2015153084 A | 8/2015 |
| JP | 2015230207 A | 12/2015 |
| JP | 2016520883 A | 7/2016 |
| KR | 101632716 B1 | 6/2016 |
| KR | 101647831 B1 | 8/2016 |
| MX | 2012015244 A | 4/2013 |
| NZ | 797807 A1 | 3/2023 |
| PT | 882280 E | 5/2002 |
| SG | 186323 A1 | 1/2013 |
| TW | M503189 U | 6/2015 |
| WO | WO-9213327 A1 | 8/1992 |
| WO | WO-9809261 A1 | 3/1998 |
| WO | WO-9826704 A1 | 6/1998 |
| WO | WO-9836258 A2 | 8/1998 |
| WO | WO-9930299 A1 | 6/1999 |
| WO | WO-9933008 A2 | 7/1999 |
| WO | WO-9731350 A1 | 8/1999 |
| WO | WO-0022260 A1 | 4/2000 |
| WO | WO-0125730 A1 | 4/2001 |
| WO | WO-0131532 A2 | 5/2001 |
| WO | WO-0133529 A1 | 5/2001 |
| WO | WO-0141612 A1 | 6/2001 |
| WO | WO-0221475 A1 | 3/2002 |
| WO | WO-02059701 A1 | 8/2002 |

(56) References Cited

FOREIGN PATENT DOCUMENTS

| | | |
|---|---|---|
| WO | WO-02077927 A1 | 10/2002 |
| WO | WO-02094073 A1 | 11/2002 |
| WO | WO-03059143 A1 | 7/2003 |
| WO | WO-03079278 A1 | 9/2003 |
| WO | WO-03082351 A2 | 10/2003 |
| WO | WO-2004052162 A1 | 6/2004 |
| WO | WO-2004101122 A2 | 11/2004 |
| WO | WO-2005040984 A2 | 5/2005 |
| WO | WO-2005055793 A2 | 6/2005 |
| WO | WO-2005094711 A2 | 10/2005 |
| WO | WO-2005055793 A3 | 12/2005 |
| WO | WO-2005117672 A1 | 12/2005 |
| WO | WO-2006036687 A1 | 4/2006 |
| WO | WO-2006086632 A2 | 8/2006 |
| WO | WO-2006133026 A2 | 12/2006 |
| WO | WO-2007001866 A2 | 1/2007 |
| WO | WO-2006135922 A3 | 8/2007 |
| WO | WO-2007090470 A1 | 8/2007 |
| WO | WO-2007127495 A2 | 11/2007 |
| WO | WO-2007129289 A1 | 11/2007 |
| WO | WO-2007133960 A2 | 11/2007 |
| WO | WO-2008088424 A1 | 7/2008 |
| WO | WO-2008118143 A2 | 10/2008 |
| WO | WO-2008119158 A1 | 10/2008 |
| WO | WO-2008133495 A1 | 11/2008 |
| WO | WO-2009087046 A1 | 7/2009 |
| WO | WO-2009097046 A1 | 8/2009 |
| WO | WO-2009097096 A1 | 8/2009 |
| WO | WO-2009134242 A1 | 11/2009 |
| WO | WO-2010026581 A2 | 3/2010 |
| WO | WO-2010101929 A2 | 9/2010 |
| WO | WO-2011038173 A1 | 3/2011 |
| WO | WO-2011085292 A2 | 7/2011 |
| WO | WO-2011131800 A1 | 10/2011 |
| WO | WO-2011161475 A1 | 12/2011 |
| WO | WO-2012064515 A2 | 5/2012 |
| WO | WO-2012150563 A1 | 11/2012 |
| WO | WO-2012152495 A1 | 11/2012 |
| WO | WO-2012161766 A1 | 11/2012 |
| WO | WO-2013003661 A1 | 1/2013 |
| WO | WO-2013025889 A1 | 2/2013 |
| WO | WO-2013025956 A1 | 2/2013 |
| WO | WO-2013033243 A2 | 3/2013 |
| WO | WO-2013049357 A2 | 4/2013 |
| WO | WO-2013049462 A1 | 4/2013 |
| WO | WO-2013055616 A2 | 4/2013 |
| WO | WO-2013058821 A1 | 4/2013 |
| WO | WO-2013063690 A1 | 5/2013 |
| WO | WO-2013070888 A1 | 5/2013 |
| WO | WO-2013074660 A1 | 5/2013 |
| WO | WO-2013140253 A1 | 9/2013 |
| WO | WO-2013165585 A1 | 11/2013 |
| WO | WO-2013190016 A1 | 12/2013 |
| WO | WO-2014027030 A2 | 2/2014 |
| WO | WO-2014035610 A1 | 3/2014 |
| WO | WO-2014037938 A2 | 3/2014 |
| WO | WO-2014046645 A1 | 3/2014 |
| WO | WO-2014060726 A1 | 4/2014 |
| WO | WO-2014125320 A1 | 8/2014 |
| WO | WO-2014205283 A1 | 12/2014 |
| WO | WO-2015017702 A2 | 2/2015 |
| WO | WO-2015054193 A1 | 4/2015 |
| WO | WO-2015061718 A1 | 4/2015 |
| WO | WO-2015070016 A2 | 5/2015 |
| WO | WO-2016168082 A1 | 10/2016 |
| WO | WO-2017200965 A1 | 11/2017 |
| WO | WO-2018165107 A1 | 9/2018 |

OTHER PUBLICATIONS

"America's Dirty Little Secret: Second Handwashing Survey Reveals Americans Still Don't Get it", American Society for Microbiology, (Sep. 19, 2000), 3 pgs.

"U.S. Appl. No. 12/000,625, Final Office Action mailed Apr. 12, 2021", 8 pgs.

"U.S. Appl. No. 14/819,349, Final Office Action mailed Jun. 8, 2021", 7 pgs.

"U.S. Appl. No. 14/819,349, Final Office Action mailed Jun. 16, 2020", 31 pgs.

"U.S. Appl. No. 14/819,349, Final Office Action mailed Oct. 9, 2019", 32 pgs.

"U.S. Appl. No. 14/819,349, Non Final Office Action mailed Feb. 10, 2020".

"U.S. Appl. No. 14/819,349, Response filed Jan. 9, 2020 to Final Office Action mailed Oct. 9, 2019", 18 pgs.

"U.S. Appl. No. 14/819,349, Response filed Apr. 26, 2021 to Non Final Office Action mailed Nov. 3, 2020", 11 pgs.

"U.S. Appl. No. 14/819,349, Response filed May 11, 2020 to Non Final Office Action mailed Feb. 10, 2020", 20 pgs.

"U.S. Appl. No. 14/819,349, Response filed Aug. 27, 2019 to Non Final Office Action mailed Apr. 5, 2019", 20 pgs.

"U.S. Appl. No. 14/819,349, Response filed Sep. 16, 2020 to Final Office Action mailed Jun. 16, 2020", 12 pgs.

"U.S. Appl. No. 14/819,349, Response filed Oct. 7, 2021 to Final Office Action mailed Jun. 8, 2021", 11 pgs.

"U.S. Appl. No. 15/912,999, Advisory Action mailed Oct. 20, 2020", 4 pgs.

"U.S. Appl. No. 15/912,999, Corrected Notice of Allowability mailed Feb. 10, 2022", 16 pgs.

"U.S. Appl. No. 15/912,999, Corrected Notice of Allowability mailed Jul. 6, 2021", 3 pgs.

"U.S. Appl. No. 15/912,999, Final Office Action mailed Jul. 9, 2020", 34 pgs.

"U.S. Appl. No. 15/912,999, Non Final Office Action mailed Mar. 18, 2021", 28 pgs.

"U.S. Appl. No. 15/912,999, Non Final Office Action mailed Nov. 27, 2019", 25 pgs.

"U.S. Appl. No. 15/912,999, Notice of Allowance mailed Jan. 4, 2021", 20 pgs.

"U.S. Appl. No. 15/912,999, Notice of Allowance mailed Jun. 10, 2021", 21 pgs.

"U.S. Appl. No. 15/912,999, Notice of Allowance mailed Aug. 31, 2021", 22 pgs.

"U.S. Appl. No. 15/912,999, Notice of Allowance mailed Oct. 29, 2021", 18 pgs.

"U.S. Appl. No. 15/912,999, Response filed Feb. 27, 2020 to Non Final Office Action mailed Nov. 27, 2019", 18 pgs.

"U.S. Appl. No. 15/912,999, Response filed Apr. 28, 2021 to Non Final Office Action mailed Mar. 18, 2021", 10 pgs.

"U.S. Appl. No. 15/912,999, Response filed Sep. 16, 2020 to Final Office Action mailed Jul. 9, 2020", 21 pgs.

"U.S. Appl. No. 15/912,999, Response filed Nov. 9, 2020 to Advisory Action mailed Oct. 20, 2020", 14 pgs.

"U.S. Appl. No. 17/383,689, Final Office Action mailed Mar. 7, 2023", 40 pgs.

"U.S. Appl. No. 17/383,689, Non Final Office Action mailed Oct. 5, 2022", 29 pgs.

"U.S. Appl. No. 17/383,689, Response filed Feb. 6, 2023 to Non Final Office Action mailed Oct. 5, 2022", 24 pgs.

"U.S. Appl. No. 17/383,689, Response filed Jun. 7, 2023 to Final Office Action mailed Mar. 7, 2023", 15 pgs.

"U.S. Appl. No. 17/648,389, Corrected Notice of Allowability mailed Jan. 18, 2024", 2 pgs.

"U.S. Appl. No. 17/648,389, Corrected Notice of Allowability mailed Oct. 24, 2023", 3 pgs.

"U.S. Appl. No. 17/648,389, Final Office Action mailed Jul. 19, 2023", 12 pgs.

"U.S. Appl. No. 17/648,389, Non Final Office Action mailed Dec. 23, 2022", 22 pgs.

"U.S. Appl. No. 17/648,389, Notice of Allowance mailed Oct. 2, 2023", 6 pgs.

"U.S. Appl. No. 17/648,389, Response filed Mar. 23, 2023 to Non Final Office Action mailed Dec. 23, 2022", 8 pgs.

"U.S. Appl. No. 17/648,389, Response filed Sep. 19, 2023 to Final Office Action mailed Jul. 19, 2023", 7 pgs.

(56) References Cited

OTHER PUBLICATIONS

"U.S. Appl. No. 18/404,202, Preliminary Amendment filed Jun. 3, 2024", 8 pgs.
"Australian Application Serial No. 2018231071, First Examination Report mailed Mar. 2, 2022", 3 pgs.
"Australian Application Serial No. 2018231071, Response filed Jun. 13, 2022 to First Examination Report mailed Mar. 2, 2022", 21 pgs.
"Bentley WiNET Tag User Guide—FAS1503, DOC1036", UltraClenz, (Jan. 25, 2011), 12 pgs.
"Brazil Application Serial No. 112019018376.0, Office Action mailed Aug. 16, 2023", 6 pgs.
"Chinese Application Serial No. 201880015582.7, Notification to Grant Patent Right for Invention mailed Jun. 3, 2021", W/English Translation, 3 pgs.
"Chinese Application Serial No. 201880015582.7, Office Action mailed Dec. 16, 2020", W/English Translation, 17 pgs.
"Chinese Application Serial No. 201880015582.7, Response filed Apr. 26, 2021 to Office Action mailed Dec. 16, 2020", W/English Claims, 24 pgs.
"Dial-A-Wash Automatic Laundry Room Atlendant for Apartment and Complex Laundry Rooms", Persyst Inc., cited in an IDS in U.S. Appl. No. 10/436,454 on May 20, 2005, 2 pgs.
"Diversey VeriCiean System Implementation and Support Guide", Diversey, Inc (Applicant points out, in accordance with MPEP 609.04(a), that the year of publication, 2012, is sufficiently earlier than the effective US. filing date, 2017, so that the particular month of publication is not in issue.), (2012), 64 pp.
"DLE-Production Summary Reports", Diversey, Diverlog-L Enhanced, (Apr. 1990), 5 pgs.
"DLE-Single Cycle Reports", Diversey, Diverlog-L Enhanced, (Apr. 1990), 5 pg.
"Don't Get Caught Dirty Handed", ASM's Microbes Afterhours, (Sep. 6, 2009), 11 pgs.
"Dr. Semmelweiss Was Right: Washing Hands Prevents Infection", Water Quality and Health Council, [Online] Retrieved from the internet: www.waterandhealth.org/newsletter/new/4/12/2017/right.htm>, (Feb. 2017), 2 pgs.
"ECOLAB® Aramark Uniform Services Joining Forces for Service Excellence", PowerPoint Presentation:, Applicant points out, in accordance with MPEP 609.04(a), that the year of publication, 1998, is sufficiently earlier than the effective U.S. filing date, so that the particular month of publication is not in issue, (1998), 69 pgs.
"ECOLAB® Balancer. Com, MRE", (Jun. 4, 1997), 4 pg.
"European Application Serial No. 18713472.1, Communication Pursuant to Article 94(3) EPC mailed Sep. 21, 2020", 5 pgs.
"European Application Serial No. 18713472.1, Communication pursuant to Rules 161(1) and 162 EPC mailed Oct. 15, 2019", 3 pgs.
"European Application Serial No. 18713472.1, Intention to Grant mailed May 10, 2021", 60 pgs.
"European Application Serial No. 18713472.1, Response filed Jan. 20, 2021 to Communication Pursuant to Article 94(3) EPC mailed Sep. 21, 2020", 19 pgs.
"European Application Serial No. 18713472.1, Response filed Jan. 20, 2021 to Extended European Search Report mailed Sep. 21, 2020", 11 pgs.
"European Application Serial No. 18713472.1, Response to Communication pursuant to Rules 161(1) and 162 EPC filed Apr. 21, 2020", 7 pgs.
"European Application Serial No. 21203245.2, Communication Pursuant to Article 94(3) EPC mailed Feb. 1, 2023", 6 pgs.
"European Application Serial No. 21203245.2, Communication Pursuant to Article 94(3) EPC mailed Jul. 10, 2024", 6 pgs.
"European Application Serial No. 21203245.2, Communication Pursuant to Article 94(3) EPC mailed Sep. 18, 2023", 6 pgs.
"European Application Serial No. 21203245.2, Extended European Search Report mailed Feb. 7, 2022", 9 pgs.
"European Application Serial No. 21203245.2, Response filed Mar. 14, 2024 to Communication Pursuant to Article 94(3) EPC mailed Sep. 18, 2023", 10 pgs.
"European Application Serial No. 21203245.2, Response filed May 26, 2023 to Communication Pursuant to Article 94(3) EPC mailed Feb. 1, 2023", 9 pgs.
"Evaluating Municipal Services: Scorecard Cleanliness Program Prospectus", [Online]. Retrieved from the Internet: <URL: http://www.worldsweeper.com/Street/Profiles/NYCScorecard.pdf>, Archived Jan. 5, 2009, (Jan. 5, 2009), 16 pgs.
"Evidence of hand hygiene to reduce transmission and infections by multi-drug resistant organisms in health-care settings", World Health Organization, (Jan. 5, 2014), 7 pgs.
"Facility Auditing Data", Diversey Inc., (Oct. 18, 2011), 2 pgs.
"Guardian™ Automated infection Control Systems (GAICS)", SaferCorp, LLC, (Feb. 6, 2010), 4 pgs.
"Guideline for Hand Hygiene in Health-Care Settings", Morbidity and Mortality Weekly Report, Recommendations and Reports (MMWR) vol. 51, No. RR-16, CDC, HICPAC, (Oct. 25, 2002), 56 pg.
"Guidelines for Control of Antibiotic Resistant Organisms", Florida Department of Health,, (Dec. 20, 1999), 34 pgs.
"Hand Hygiene", Progressive Grocer, vol. 76, No. 8, (Aug. 1997), 111-112.
"Hand Washing, Cleaning, Disinfection and Sterilization in Health Care", Infection Control Guidelines, Canada Communicable Disease Report, vol. 24S8, (Dec. 1998), 66 pgs.
"Home Routines App for iPhone, iPad, & iPod touch", [Online] Retrieved from the internet: <http://www.homeroutines.com>, (2010), 7 pgs.
"Home Routines for iPhone, iPod touch, and iPad on the iTunes App Store", [Online] Retrieved from the internet: <https:/litunes.apple.com/us/app/homeroutines/id353117370?mt===8>, (Sep. 5, 2013), 3 pgs.
"Hygiene Services Assessment Scheme, Assessment Report", Mallow General Hospital, (Oct. 2007), 38 pgs.
"IMAP Internet Mobile Auditing Platform", Diversey Inc., (2012), 2 pg.
"IMAP TM/MC . . . Data Collection & Reporting Platform", Diversey Inc., (Sep. 5, 2013), 2 pg.
"International Application Serial No. PCT/US2018/021068, International Preliminary Report on Patentability mailed Sep. 19, 2019", 8 pgs.
"International Application Serial No. PCT/US2018/021068, International Search Report mailed Jun. 25, 2018", 4 pgs.
"International Application Serial No. PCT/US2018/021068, Written Opinion mailed Jun. 25, 2018", 6 pgs.
"InTouch Water Treatment Information Management Solution", Nexgen SI, Inc., (Mar. 29, 1999), 59 pgs.
"Laundry Information System: Overview Reports", NOVALINK™ brochure:, (Dec. 13, 1995), 6 pgs.
"LDAS-2000 Remote Information Control and Management System for the Commercial Laundry and Vending Industry", Persyst Inc., cited in an IDS in U.S. Appl. No. 10/436,454 on May 20, 2005, 4 pgs.
"Making the World a More Hygienic Place", Ophardt, Hygiene-Technik GmbH+ Co. KG, Hygiene Compliance Solutions, 2009, Applicant points out, in accordance with MPEP 609.04(a), that the year of publication, 2009, is sufficiently earlier than the effective U.S. filing date, 2017, so that the particular month of publication is not in issue, (2009), 1 pg.
"Measuring Hand Hygiene Adherence: Overcoming the Challenges", The Joint Commission, (2009), 234 pgs.
"Net/Tech to Unveil Patented Hygiene Guard Hand-Washing Monitoring System at the National Restaurant Show", BusinessWire, (Apr. 3, 1997), 3 pgs.
"NOVALINK™ Laundry Information System", ControlMaster Version 2.0 for Windows User's Guide, 2000, Applicant points out, in accordance with MPEP 609.04(a), that the year of publication, 2000, is sufficiently earlier than the effective U.S. filing date, so that the particular month of publication is not in issue, (2000), 39 pgs.
"NOVALINK™ OverViewTM Program Pricing", cited in an IDS in U.S. Appl. No. 10/436,454 on May 20, 2005, 1 pgs.
"ORION Liquid Laundry Supply Dispenser", Nova Controls, (Feb. 1989), 5 pgs.
"Patient Safeguard System Healthcare Worker Badge User's Guide", DOC1046 Revision 8, UltraClenz, (Mar. 14, 2012), 21 pgs.

(56) References Cited

OTHER PUBLICATIONS

"ProGiene System Description for UL and CE Mark Approval", UltraClenz, (Feb. 8, 2002), 5 pp.

"Prosecution History from U.S. Appl. No. 12/683,666, dated Aug. 21, 2012 through Apr. 17, 2013", 38 pgs.

"Prosecution History from U.S. Appl. No. 12/787,064, dated Dec. 6, 2012 through Apr. 8, 2013", 20 pgs.

"Prosecution History from U.S. Appl. No. 12/787,097, dated Jun. 4, 2012 through Nov. 7, 2012", 21 pgs.

"Prosecution History from U.S. Appl. No. 14/164,930, dated Mar. 24, 2015 through Oct. 5, 2016", 123 pgs.

"Prosecution History from U.S. Appl. No. 14/819,349, dated Apr. 5, 2019 through Nov. 1, 2021", 229 pgs.

"Prosecution History from U.S. Appl. No. 15/406,129, dated Jun. 1, 2017 through Jul. 6, 2017", 23 pgs.

"Prosecution History from U.S. Appl. No. 15/912,999, dated Nov. 27, 2019 through Oct. 29, 2021", 257 pgs.

"Prosecution History from U.S. Appl. No. 16/185,499, dated Mar. 28, 2019 through Jul. 8, 2019", 13 pgs.

"Prosecution History from U.S. Appl. No. 17/000,625, dated Apr. 12, 2021 through Nov. 15, 2021", 12 pgs.

"Recommendations for Preventing the Spread of Vancomycin Resistance", HICPAC, Morbidity and CDC Mortality Weekly Report, Recommendations and Reports, vol. 44, No. RR-12, 1-13, (Sep. 22, 1995), 16 pgs.

"Relax. We've Got Your Pool Concerns Under Control", ECOLAB® Inc., product brochure:, Applicant points out, in accordance with MPEP 609.04(a), that the year of publication, 1998, is sufficiently earlier than the effective U.S. filing date, so that the particular month of publication is not in issue, (1998), 4 pg.

"Reporting", Diversey.com, (Sep. 5, 2013), 1 pg.

"SaferCorp Life Advantage Solutions presents SaferHands™ Hospital Automated Hand Hygiene Monitoring System", SaferCorp, LLC, retrieved electronically from http://www.guardianics.com/ on Dec. 15, 2010, 14 pgs.

"Sample Reports, Nova Controls", (Oct. 1997), 8 pgs.

"Sample Reports, NOVALINK™ System", (Jan. 1996), 9 pgs.

"Saudi Arabia Application Serial No. 519410049, Response filed Jan. 6, 2021 to Substantive Examination Report mailed Sep. 29, 2021", 86 pgs.

"Saudi Arabia Application Serial No. 519410049, Substantive Examination Report mailed Sep. 29, 2021", W/English Translation, 10 pgs.

"Save Money and Gain Sales Features?", Nova Controls, Nova News, (Aug. 12, 1992), 1 pg.

"Sealed Air's Diversey Business Introduces Mobile Application to Capture Facility Auditing Data", Diversey Inc., (Oct. 18, 2011), 2 pg.

"United Arab Emirates Application Serial No. P6001266/2019, First Examination Report mailed Sep. 21, 2022", 6 pgs.

"United Arab Emirates Application Serial No. P6001266/2019, Response filed May 28, 2023 to First Examination Report mailed Sep. 21, 2022", 9 pgs.

"Unleash Your Data, the power of iMAP is now available on virtually any smart device. Get robust data collection and analysis anytime, anywhere, in any language", Diversey Inc., (Sep. 15, 2011), 2 pg.

"Wash-Aisle Productivity Manager Software Guide", T-JET™ 2000 PC, ECOLAB® Textile Care Division, cited in an IDS in U.S. Appl. No. 10/436,454 on May 20, 2005, 29 pgs.

"We'd like to make a couple of things perfectly Clear", ECOLAB@ Inc., product brochure, Applicant points out, in accordance with MPEP 609.04(a), that the year of publication, 1998, is sufficiently earlier than the effective U.S. filing date, so that the particular month of publication is not in issue, (1998), 4 pg.

"WHO Guidelines on Hand Hygiene in Health Care", World Health Organization, (2009), 270 pg.

"WHO Guidelines on Hand Hygiene in Health Care (Advanced Draft)", World Health Organization, (Apr. 2006), 216 pp.

Al-Hamad, et al., "How Clean is Clean? Proposed Methods for Hospital Cleaning Assessment", Journal of Hospital Infection, vol. 70, (Oct. 9, 2008), 328-334.

Bourn, "The Management and Delivery of Hospital Cleaning Services in Wales", National Audit Office Wale, (May 23, 2003), 39 pgs.

Dancer, "How do we Assess Hospital Cleaning? A Proposal for Microbiological Standards for Surface Hygiene in Hospitals", Journal of Hospital Infection, vol. 56, (Sep. 2003), 10-15.

David, L Snodgrass, "", U.S. Appl. No. 61/437,466, (Jan. 28, 2011).

David, L Snodgrass, "", U.S. Appl. No. 61/486,491, (May 16, 2011).

Diller, et al., "Estimation of hand hygiene opportunities on an adult medical ward using 24-hour camera surveillance: Validation of the HOW2 Benchmark Study", American Journal of Infection Control, vol. 42, (2014), 602-607.

Dix, et al., "Environmental Surface Cleaning: First Defense Against Infectious Agents", Infection Control Today Magazine, (Dec. 1, 2005), 6 pg.

Elliott, "Determining Three Metrics for Cleaning Satisfaction", [Online]. Retrieved from the Internet: <URL: http://www.facilitiesnet.com/fn/article.asp?id-7698,equipmentrentaltools/article/Determining-Three-Metrics-for-Cleaning-Satisfaction--7698#>, (Nov. 2007), 2 pg.

Exner, et al., "Household Cleaning and Surface Disinfection: New Insights and Strategies", Journal of Hospital Infection, vol. 56, (Apr. 2004), s70-s75.

Garner, et al., "Guideline for Handwashing and Hospital Environmental Control", CDC Prevention Guidelines, (Jan. 1, 1985), 10 pgs.

Garner, et al., "Guidelines for Isolation Precautions in Hospitals", Hospital Infection Control Advisory Committee, (Jan. 1, 1996), 39 pgs.

Green, "Hand hygiene in 2015: 7 Findings", http://www.beckershospitalreview.com/quality!hand-hygiene-i n-2015-7-findings.htm1?tmpl=coin ponent&print= 1 &layout=default&page=, [Online]. Retrieved from the Internet: <URL: http://www.beckershospitalreview.com/quality!hand-hygiene-i n-2015-7-findings.htm1?tm pl=coin ponent &print= 1 &layout=default&page=>, (Nov. 12, 2015), 1 pg.

Griffith, et al., "An Evaluation of Hospital Cleaning Regimes and Standards", J. Hosp. Infect., vol. 45, accepted Dec. 23, 1999, (2000), 19-28.

Griffith, "Nosocomial infection: Are there lessons from the food industry?", The Biomedical Scientist, (Aug. 2006), 697-699.

Griffith, et al., "The Effectiveness of Existing and Modified Cleaning Regimens in a Welsh Hospital", Journal of Hospital Infection, vol. 66, (Jul. 26, 2007), 352-359.

Hamilton, et al., "Hand Hygiene", Wild Iris Medical Education, Inc., 2014, Applicant points out, in accordance with MPEP 609.04(a), that the year of publication, 2014, is sufficiently earlier than the effective U.S. filing date, 2017, so that the particular month of publication is not in issue, 24 pgs.

Larson, et al., "A Multifaceted Approach to Changing Handwashing Behavior", American Journal of Infection Control, vol. 25, (Feb. 1997), 3-10.

Larson, "APIC Guideline for Hand Washing and Hand Antisepsis in Health-Care Settings*", APIC Guidelines Committee, 1995, Am J Infect Control, 23:251, Applicant points out, in accordance with MPEP 609.04(a), that the year of publication, 1995, is sufficiently earlier than the effective U.S. filing date, 2017, so that the particular month of publication is not in issue, (1995), 18 pgs.

Levchenico, et al., "Embedded System for Hygiene Compliance Monitoring", IEEE Transactions on Automation Science and Engineering, vol. 7, No. 3, (Jul. 2010), 4 pgs.

Lewis, et al., "A Modified ATP Benchmark for Evaluating the Cleaning of Some Hospital Environmental Surfaces", Journal of Hospital Infection, vol. 69, (May 12, 2008), 156-163.

Malik, et al., "Use of Audit Tools to Evaluate the Efficacy of Cleaning Systems in Hospitals", Am. J. Infect. Control, vol. 31, No. 3, (May 2003), 181-187.

Mangram, M D, et al., "Guideline for Prevention of Surgical Site Infection", 1999, Infection Control and Hospital Epidemiology 20(4), (Apr. 1999), 247-278.

(56) References Cited

OTHER PUBLICATIONS

Meengs, et al., "Hand Washing Frequency in an Emergency Department", Annals of Emergency Medicine, vol. 23, No. 6, (Jun. 1994), 1307-1312.

Mills, et al., "Guidelines for Working with Rodents Potentially Infected with Hantavirus", Journal of Mammalogy, vol. 76, No. 3, (Aug. 1995), 716-722.

Munro, et al., "Treating Exposure to Chemical Warfare Agents: Implications for Health Care Providers and Community Emergency Planning", Environmental Health Perspectives, vol. 89, 1990, Applicant points out, in accordance with MPEP 609.04(a), that the year of publication, 1990, is sufficiently earlier than the effective U.S. filing date, 2017, so that the particular month of publication is not in issue, (1990), 205-2015.

Nexgen, SI, "In Touch Water Treatment Information Management Solution", (Mar. 29, 1999), 59 pgs.

Pittet, et al., "Compliance with Handwashing in a Teaching Hospital", Annals of Internal Medicine, vol. 130, No. 2, (Jan. 19, 1999), 126-130.

Quattrin, MD, et al., "Application of Hazard Analysis Critical Control Points to Control Surgical Site Infections in Hip and Knee Arthroplasty", Orthopedics 31:132, 6 pp., SLACK Incorporated., (Feb. 2008), 6 pgs.

Sahud, et al., "An Electronic Hand Hygiene Surveillance Device: A Pilot Study Exploring Surrogate Makers for Hand Hygiene Compliance", Infection Control and Hospital Epidemiology, vol. 31, No. 6, (Jun. 2010), 6 pgs.

Sax, et al., "My five moments for hand hygiene: a user-centered design approach to understand, train, monitor and report hand hygiene", Journal of Hospital Infection, vol. 67, (Aug. 27, 2007), 9-21.

Semmelweis, "The Etiology, Concept, and Prophylaxis of Childbed Fever", The University of Wisconsin Press, Applicant points out, in accordance with MPEP 609.04(a), that the year of publication, 1983, is sufficiently earlier than the effective U.S. filing date, 2017, so that the particular month of publication is not in issue, (1983), 14 pgs.

Steed, et al., "Hospital Hand Hygiene Opportunities: Where and When (HOW2)? The HOW2 Benchmark Study", American Journal of Infection Control, vol. 39, (Feb. 2011), 8 pgs.

Sturman, et al., "Cornell University Hospitality Report: A New Method for Measuring Housekeeping Performance Consistency", CHR Reports, vol. 6, No. 11, (Sep. 2006), 15 pgs.

Swedberg, "RFID-based Hand-Hygiene System Prevents Health-Care Acquired Infections", RFD Journal, (Jun. 10, 2010), 2 pgs.

Swoboda, et al., "Electronic Monitoring and Voice Prompts Improve Hand Hygiene and Decrease Nosocomial Infections in an Intermediate Care Unit", Crit Care Med, vol. 32, No. 2, Applicant points out, in accordance with MPEP 609.04(a), that the year of publication, 2004, is sufficiently earlier than the effective U.S. filing date, Jan. 13, 2017, so that the particular month of publication is not in issue, (2004), 358-363.

Taylor, "An Evaluation of Handwashing Techniques-1", Nursing Times, vol. 74, (Jan. 12, 1978), 54-55.

Thompson, et al., "Handwashing and Glove Use in a Long-Term-Care Facility", Infection Control and Hospital Epidemiology, vol. 18, No. 2, (Feb. 1997), 97-103.

Tibballs, et al., "Teaching Hospital Medical Staff to Handwash", The Medical Journal of Australia, vol. 164, No. 7, (Apr. 1, 1996), 395-398.

Tokhtuev, et al., "U.S. Appl. No. 14/819,349, filed Aug. 5, 2015".

Tokhtuev, et al., "U.S. Appl. No. 17/383,689, filed Jul. 23, 2021".

Tsai, et al., "iMAT: Intelligent Medication Administration Tools", (Aug. 2010), 8 pgs.

Van Ryzin, et al., "Measuring Street Cleanliness: A Comparison of New York City's Scorecard and Results from a Citizen Survey", Public Administration Review 68(2), (Mar./Apr. 2008), 295-303.

Watanakunakorn, et al., "An Observational Study of Hand Washing and Infection Control Practices by Healthcare Workers", Infection Control and Hospital Epidemiolgy, vol. 19, No. 11, (Nov. 1998), 858-860.

Yoshikura, "Workflow from Clean to Dirty, HACCP and Inclusiveness Principles in Effective Implementation of Hospital Infection Control", Jpn. J. Infect. Dis. 53, (Jun. 6, 2000), 2 pgs.

Zuhlsdorf, et al., "Cleaning Efficacy of Nine Different Cleaners in a Washer-Disinfector Designed for Flexible Endoscopes", Journal of Hospital Infection, vol. 52, (Oct. 9, 2002), 206-211.

"New Zealand Application Serial No. 756874, Response filed Mar. 19, 2025 to First Examiner Report mailed Aug. 22, 2024", 99 pgs.

"New Zealand Application Serial No. 797807, Response filed Mar. 19, 2025 to First Examiner Report mailed Aug. 23, 2024", 9 pgs.

"New Zealand Application Serial No. 756874, First Examiner Report mailed Aug. 22, 2024", 3 pgs.

"New Zealand Application Serial No. 797807, First Examiner Report mailed Aug. 23, 2024", 4 pgs.

"New Zealand Application Serial No. 797807, Subsequent Examiners Report mailed Mar. 20, 2025", 5 pgs.

"New Zealand Application Serial No. 756874, Office Action mailed Mar. 20, 2025", 2 pgs.

"New Zealand Application Serial No. 756874, Subsequent Examiners Report mailed Mar. 21, 2025", 2 pgs.

"European Application Serial No. 21203245.2, Communication Pursuant to Article 94(3) EPC mailed Apr. 2, 2025", 6 pgs.

"New Zealand Application Serial No. 797807, Response filed Jun. 26, 2025 to Subsequent Examiners Report mailed Mar. 20, 2025", w English Claims, 47 pgs.

"New Zealand Application Serial No. 797807, Subsequent Examiners Report mailed Jul. 2, 2025", 2 pgs.

\* cited by examiner

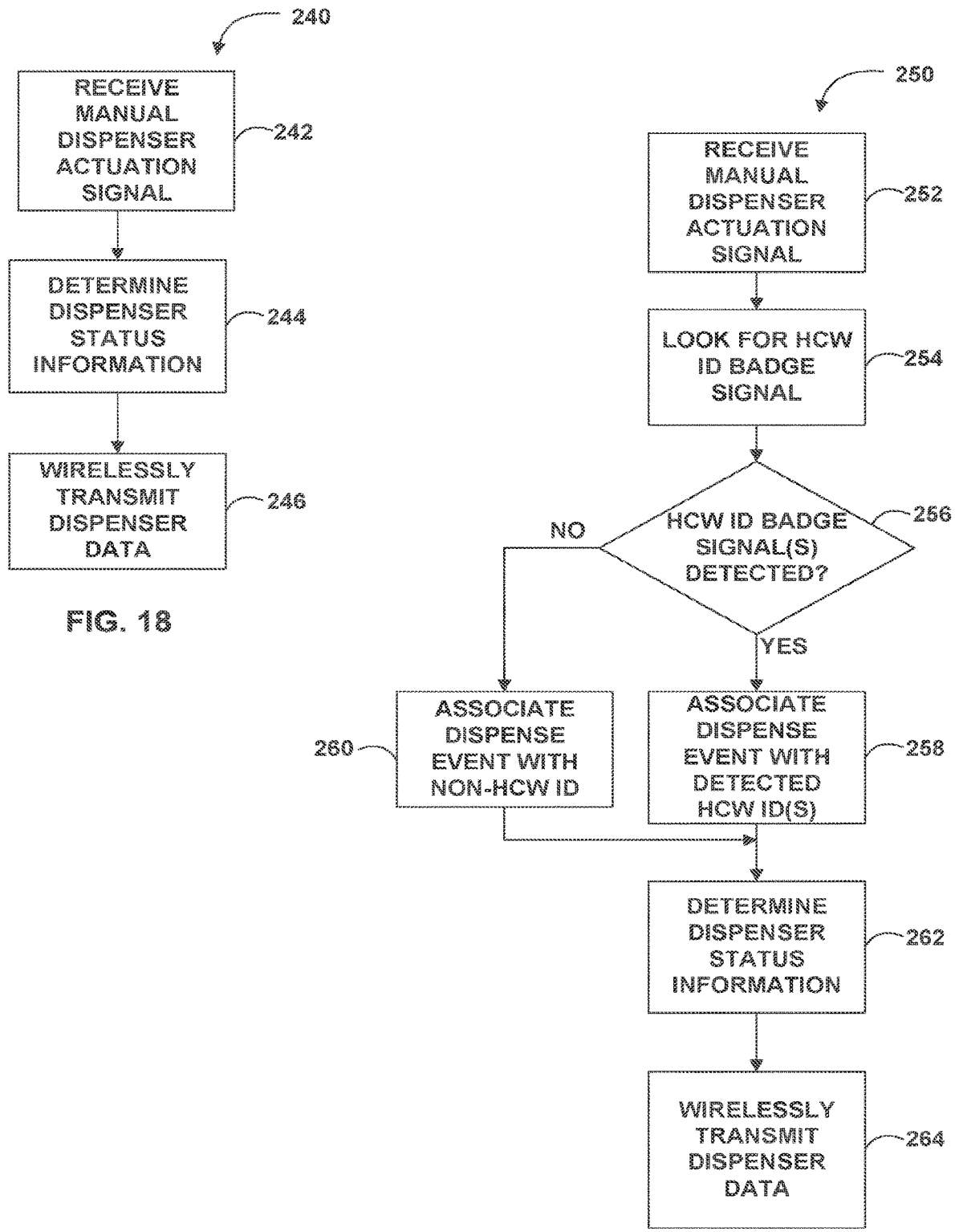

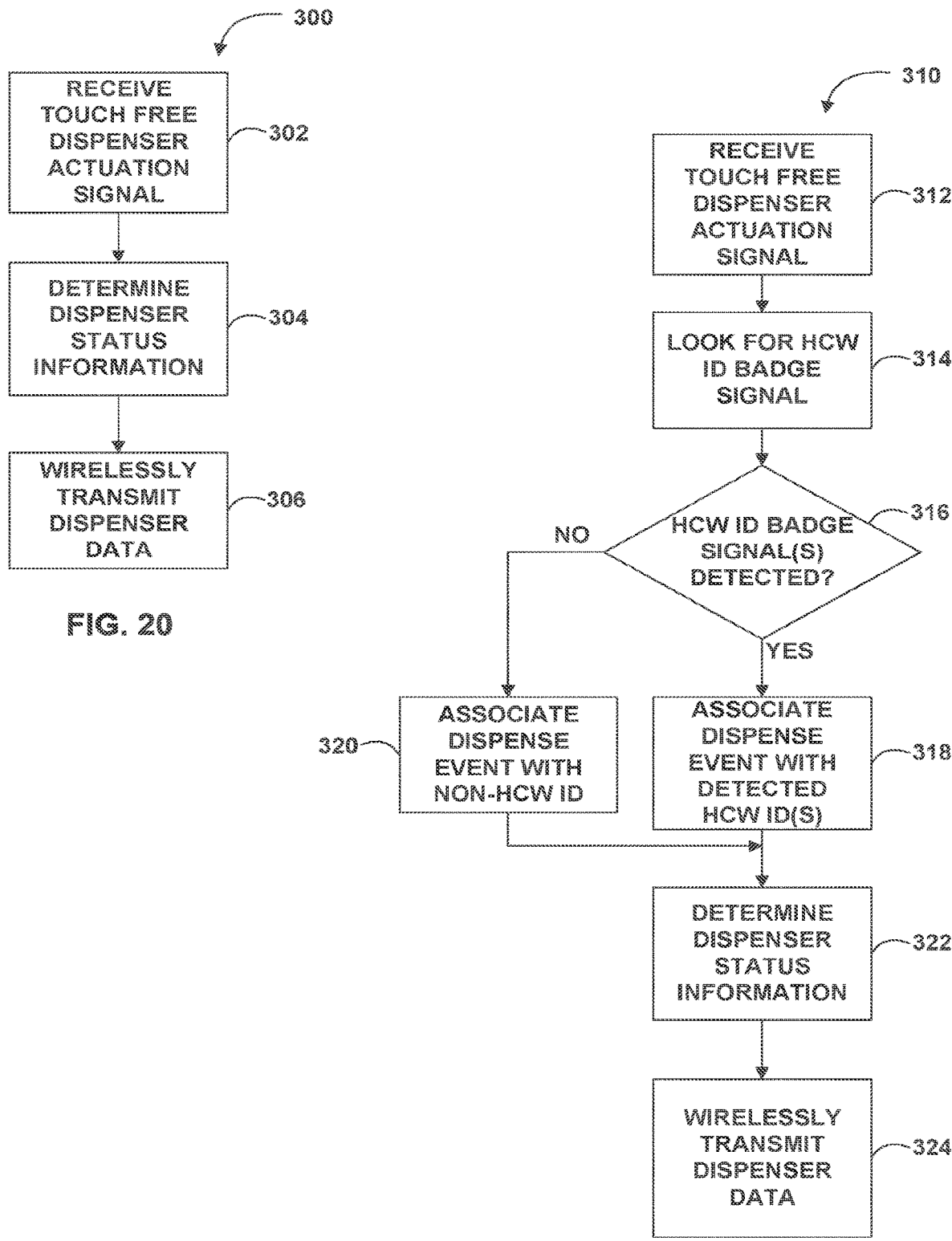

MONITORING MODULES FOR HAND HYGIENE DISPENSERS

This application is a continuation of U.S. patent application Ser. No. 17/648,389, filed Jan. 19, 2022, now issued as U.S. Pat. No. 11,903,537, which is a continuation of U.S. patent application Ser. No. 15/912,999, filed Mar. 6, 2018, now issued as U.S. Pat. No. 11,272,815, which claims the benefit of U.S. Provisional Application No. 62/468,214 filed Mar. 7, 2017, each of which are incorporated by reference herein in their entirety.

TECHNICAL FIELD

The disclosure relates to monitoring of product dispensers.

BACKGROUND

Despite improvements in hand hygiene, stricter compliance requirements, and efforts to optimize isolation practices, hospitals and other healthcare facilities are losing the war on nosocomial or Hospital Acquired Infections (HAIs). A hospital acquired infection is an infection acquired in a hospital or other healthcare facility by a patient admitted for some reason other than that specific infection. Hospital acquired infections may include infections appearing 48 hours or more after hospital admission or within 30 days after discharge. They may also include infections due to transmission from colonized healthcare workers, or occupational exposure to infection among staff of the facility. Although the majority of hospital acquired infections are preventable, sadly their incidence has only increased.

Hospital acquired infections have become more rampant as antibiotic resistance spreads. Many factors contribute to the increased incidence of hospital acquired infections among hospital patients. For example, hospitals house large numbers of people who are sick and therefore have weakened immune systems. Medical staff move from patient to patient and see many patients a day, providing a way for pathogens to spread. Research indicates that hand hygiene practices are followed only 40% of the time by healthcare workers, even after exhaustive process improvements and training efforts. Many medical procedures, such as surgery, injections and other invasive procedures bypass the body's natural protective barriers, providing entry points for pathogens. The wide-spread use of antibiotics has contributed to the emergence of resistant strains of microorganisms in healthcare facilities and well as in the community.

Compliance with hand hygiene guidelines is considered the most effective action health care workers can take to reduce pathogen transmission in health care settings. Despite this, hand hygiene compliance remains low, and improvement efforts tend to lack sustainability.

SUMMARY

In general, the disclosure relates to systems and associated processes that monitor product dispensers. For example, a hand hygiene compliance system may monitor, analyze and report on hand hygiene compliance at a hospital or other healthcare facility.

In one example, the disclosure is directed to a device that monitors dispense events at a hand hygiene product dispenser, comprising a bottle presence trigger configured to detect presence of a hand hygiene product bottle in the dispenser, a module controller configured to receive a dispenser actuation signal, the module controller further configured to generate dispenser data upon receipt of the dispenser actuation signal, the dispenser data including a dispense event indication and a bottle presence indication, and a wireless transceiver configured to wirelessly transmit the dispenser data upon receipt of the dispenser actuation signal.

In some examples, the module controller is configured to receive the dispenser actuation signal from a switch that detects actuation of a manual hand hygiene product dispenser. In some examples, the module controller is configured to receive the dispenser actuation signal from a switch that detects actuation of a touch free hand hygiene product dispenser. In some examples, the hand hygiene product dispenser is a manually actuated hand hygiene product dispenser. In some examples, the hand hygiene product dispenser is a touch free hand hygiene product dispenser.

In some examples, the module controller is further configured to store a dispense event count upon receipt of the dispenser actuation signal. In some examples, the bottle presence trigger comprises a switch that moves from an open position to a closed position when a product bottle is installed into the hand hygiene product dispenser; and wherein the module controller is further configured to reset a dispense event count when the switch moves from the open position to a closed position.

In some examples, the dispenser data includes the dispense event count. In some examples, the dispenser beacon module further includes an indicator that is illuminated by the module controller upon receipt of the dispenser actuation signal. In some examples, the bottle presence trigger includes one of a plunger switch, a pin switch, or a rocker switch. In some examples, the bottle presence trigger is moved to a closed position when the hand hygiene product bottle is present in the hand hygiene product dispenser.

In another example, the disclosure is directed to a dispenser beacon module that provides for wireless communication of dispenser data from a manually actuated hand hygiene product dispenser, comprising a housing having a module base and a module cover, a bottle presence trigger on an outer surface of the housing that when closed provides a bottle presence signal indicative of presence of a hand hygiene container in the hand hygiene product dispenser, a dispenser actuation switch that when closed provides a dispenser actuation signal, the module base including a slot configured to slidably receive a portion of an actuator of the manually actuated hand hygiene product dispenser, an actuation slider configured to slidably engage the portion of the actuator and close the dispenser actuation switch when the actuator is manually actuated by a user, a controller that receives the dispenser actuation signal, detects a corresponding dispense event, and stores corresponding dispense event data, wherein the controller further determines status information corresponding to the dispense event, including a battery level, a bottle presence indicator, a dispense event count, and a number of dispenses remaining, and wherein the controller wirelessly transmits the dispense event data to a remote computing device, the dispense event data including the time and date of the detected dispense event, the battery level, the bottle presence indicator, the dispense event count, and the number of dispenses remaining.

In some examples, the housing is sized to be received into a receptacle within the hand hygiene product dispenser.

In some examples, the module controller detects a change in the bottle presence trigger from closed to open to detect removal of the product container from the hand hygiene product dispenser, and detects a subsequent closure of the bottle presence trigger to detect installation of another product container into the hand hygiene product dispenser, and generates a product bottle replacement indication upon detection of the subsequent closure of the bottle presence trigger.

In some examples, the module controller compares a number of dispenses remaining associated with the product container to a predetermined alert level to determine whether the product container was replaced before the predetermined alert level was reached.

In some examples, the module controller is further configured to communicate with an identification badge associated with a user upon detection of a dispense event and to receive user identification information from the identification badge. In some examples, the dispenser data further includes the user identification information associated with the dispense event.

In another example, the disclosure is directed to a dispenser beacon module that provides for wireless communication of dispenser data from a touch free hand hygiene product dispenser, comprising a housing having a module base and a module cover, a bottle presence trigger on an outer surface of the housing that when closed provides a bottle presence signal indicative of presence of a hand hygiene product container in the touch free hand hygiene product dispenser, a controller that receives an indication of a touch free dispenser actuation from the touch free hand hygiene product dispenser, detects a corresponding dispense event, and stores corresponding dispense event data, wherein the controller further determines status information corresponding to the dispense event, including a battery level associated with the dispenser beacon module, a battery level associated with the touch free dispenser, a bottle presence indicator, a dispense event count, and a number of dispenses remaining, and wherein the controller wirelessly transmits the dispense event data to a remote computing device, the dispense event data including the time and date of the detected dispense event, the battery level associated with the dispenser beacon module, a battery level associated with the touch free dispenser, the bottle presence indicator, the dispense event count, and the number of dispenses remaining.

In some examples, the module controller detects a change in the bottle presence trigger from closed to open to detect removal of the product container from the hand hygiene product dispenser, and detects a subsequent closure of the bottle presence trigger to detect installation of another product container into the hand hygiene product dispenser, and generates a product bottle replacement indication upon detection of the subsequent closure of the bottle presence trigger.

In some examples, the module controller compares a number of dispenses remaining associated with the product container to a predetermined alert level to determine whether the product container was replaced before the predetermined alert level was reached.

In some examples, the dispenser beacon module further includes an indicator that is illuminated by the controller upon receipt of the dispenser actuation signal. In some examples, the bottle presence trigger includes one of a plunger switch, a pin switch, or a rocker switch.

In some examples, the module controller is further configured to communicate with an identification badge associated with a user upon detection of a dispense event and to receive user identification information from the identification badge. In some examples, the dispenser data further includes the user identification information associated with the dispense event.

The details of one or more examples are set forth in the accompanying drawings and the description below. Other features and advantages will be apparent from the description and drawings, and from the claims.

BRIEF DESCRIPTION OF DRAWINGS

FIG. 18 is a flowchart illustrating an example process by which a manual dispenser beacon module may detect manual actuations of a manual hand hygiene product dispenser and wirelessly transmit dispenser data associated with the dispense event.

FIG. 19 is a flowchart illustrating another example process by which a manual dispenser beacon module may detect manual actuations of a manual hand hygiene product dispenser and wirelessly transmit dispenser data associated with the dispense event.

FIG. 20 is a flowchart illustrating an example process by which a touch free dispenser beacon module may detect actuations of a touch free hand hygiene product dispenser and wirelessly transmit dispenser data associated with the dispense event.

FIG. 21 is a flowchart illustrating another example process by which a touch free dispenser beacon module may detect actuations of a touch free hand hygiene product dispenser and wirelessly transmit dispenser data associated with the dispense event.

DETAILED DESCRIPTION

In general, the disclosure relates to systems and associated processes that monitor hand hygiene compliance. For example, the hand hygiene compliance system may monitor, analyze and report on hand hygiene compliance at a hospital or other healthcare facility. The disclosure describes dispenser beacon modules that may be installed in existing hand hygiene product dispensers to provide wireless communication of hand hygiene data to or from a dispenser. In one example, a manual dispenser beacon module is configured to be used with a manually actuated hand hygiene product dispenser to monitor hand hygiene compliance events associated with the dispenser, and to wirelessly transmit hand hygiene data to or from the manual dispenser. In another example, a touch free dispenser beacon module is configured to be used with a touch free hand hygiene product dispenser to monitor hand hygiene compliance events associated with the dispenser, and to wirelessly transmit hand hygiene data to or from the touch free dispenser. Additional dispenser status information may be included in the dispenser data, such as dispenser identification information, healthcare worker identification information, current battery levels, product bottle presence/absence, number of dispenser actuations, out-of-product indications, etc.

The manual and touch free dispenser beacon modules described herein may be used with any of the systems or incorporate any of the features shown and described in U.S. Pat. No. 8,502,680 issued Aug. 6, 2013; U.S. Pat. No. 8,395,515 issued Mar. 12, 2013; U.S. Pat. No. 8,264,343 issued Sep. 11, 2012; U.S. Pat. No. 8,564,431 issued Oct. 22, 2013; U.S. Pat. No. 8,674,840 issued Mar. 18, 2014; U.S. Pat. No. 8,482,406 issued Jul. 9, 2013; U.S. Pat. No. 8,872,665 issued Oct. 28, 2014; U.S. Pat. No. 8,783,511 issued Jul. 22, 2014; and U.S. Pat. No. 8,633,816 issued Jan. 21, 2014; each of which is incorporated herein by reference in its entirety.

Figure 2:
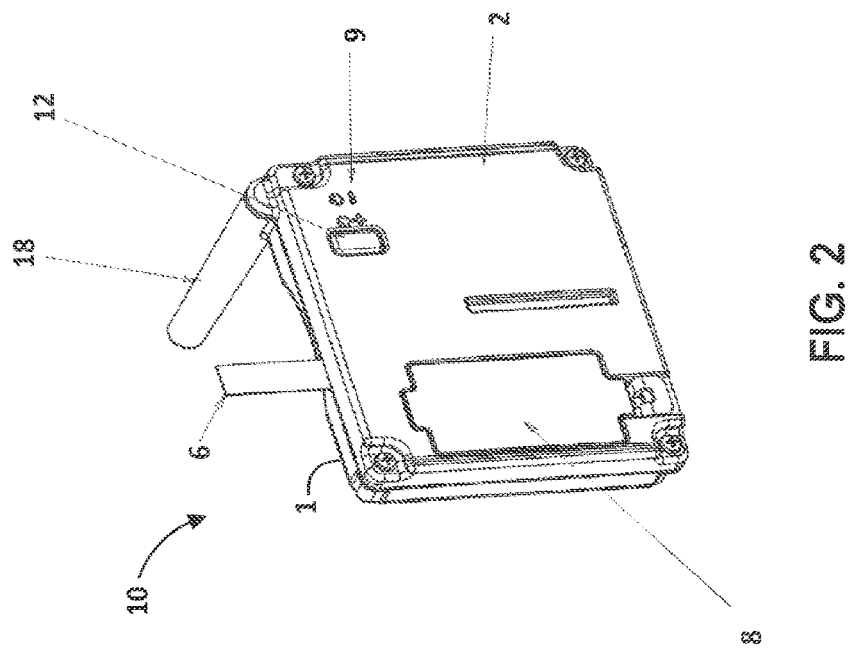
FIGS. 1 and 2 show a front perspective view and a back perspective view, respectively, of an example manual dispenser beacon module.
Figure 1:
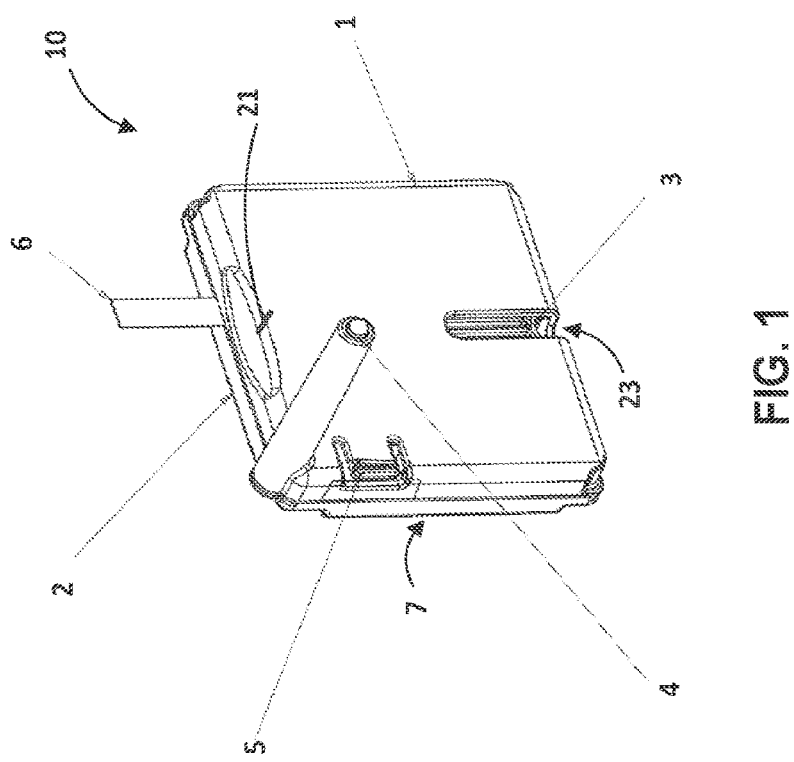

FIGS. 1 and 2 show a front perspective view and a back perspective view, respectively, of an example manual dispenser beacon module 10. Manual dispenser beacon module may be used with a manually actuated hand hygiene product dispenser to monitor hand hygiene events associated with the manual dispenser, and to wirelessly transmit hand hygiene data (including data concerning the monitored hand hygiene events) to or from the manual dispenser. Dispenser beacon module 10 includes a housing 7 having a module base 1 and a module cover 2, an actuation slider 3, an LED indicator 4, a locking mechanism 5, a release strap 6, a battery compartment door 8, and a firmware access port 12. Module base 1 is configured to form a slot 23 through which a manual dispenser actuator may engage with an actuation slider 3 (see FIG. 5A).

In some examples, the manual dispenser beacon module 10 is further configured to wirelessly transmit and/or receive communication from one or more computing device(s). For example, the beacon module 10 may receive remote software updates, remote configuration settings (e.g., range settings, product empty settings, settings for a number of dispense events before a product bottle should be refilled or replaced, etc.) from one or more computing devices. The beacon module 10 may further communicate with one or more other beacon modules in healthcare setting, such as those associated with other dispensers, with motion detectors in a patient room or other defined area, with patient zone beacons in a patient room or other defined area, or other such devices in a healthcare setting that may be useful for monitoring of hand hygiene compliance. The beacon module 10 may be further configured to wirelessly communicate (both transmit and receive) with one or more uniquely assigned healthcare worker identification badges. For example, the beacon module 10 may be configured to communicate with a badge, obtain healthcare worker identification information from the badge, and associate a detected dispense event with the healthcare worker identification information.

Figure 4:
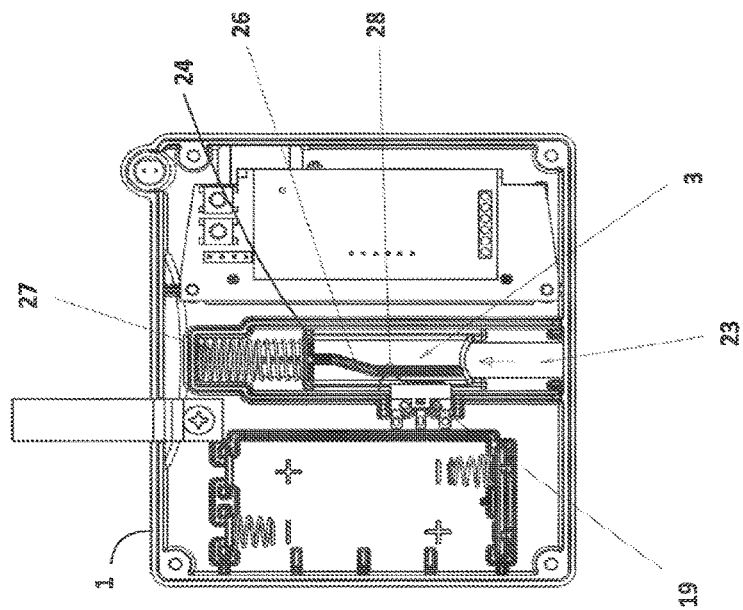
FIGS. 3 and 4 show the internal components of an example manual dispenser beacon module with the module cover removed.
Figure 3:
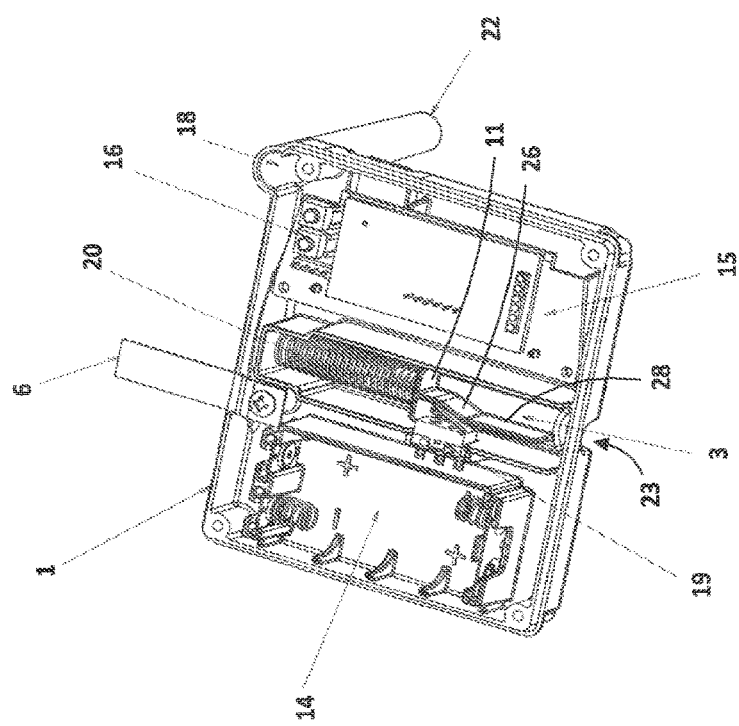

FIGS. 3 and 4 show the internal components of example manual dispenser beacon module 10 with module cover 2 removed. In FIG. 3, actuation slider 3 is in an open (at rest or non-actuated) position. In FIG. 4, actuation slider 3 is in a closed (actuated) position. The internal components of the manual dispenser beacon module 10 include a PCB assembly 15, actuation slider 3 and a return spring 20, a micro switch 19, and a battery compartment 14. In this example, battery compartment 14 is configured to receive 2 AA batteries that provide power to PCB assembly 15. In other examples, manual dispenser beacon module may be powered using different batteries or may be hard-wired to the electrical system of the building.

Figure 5A:
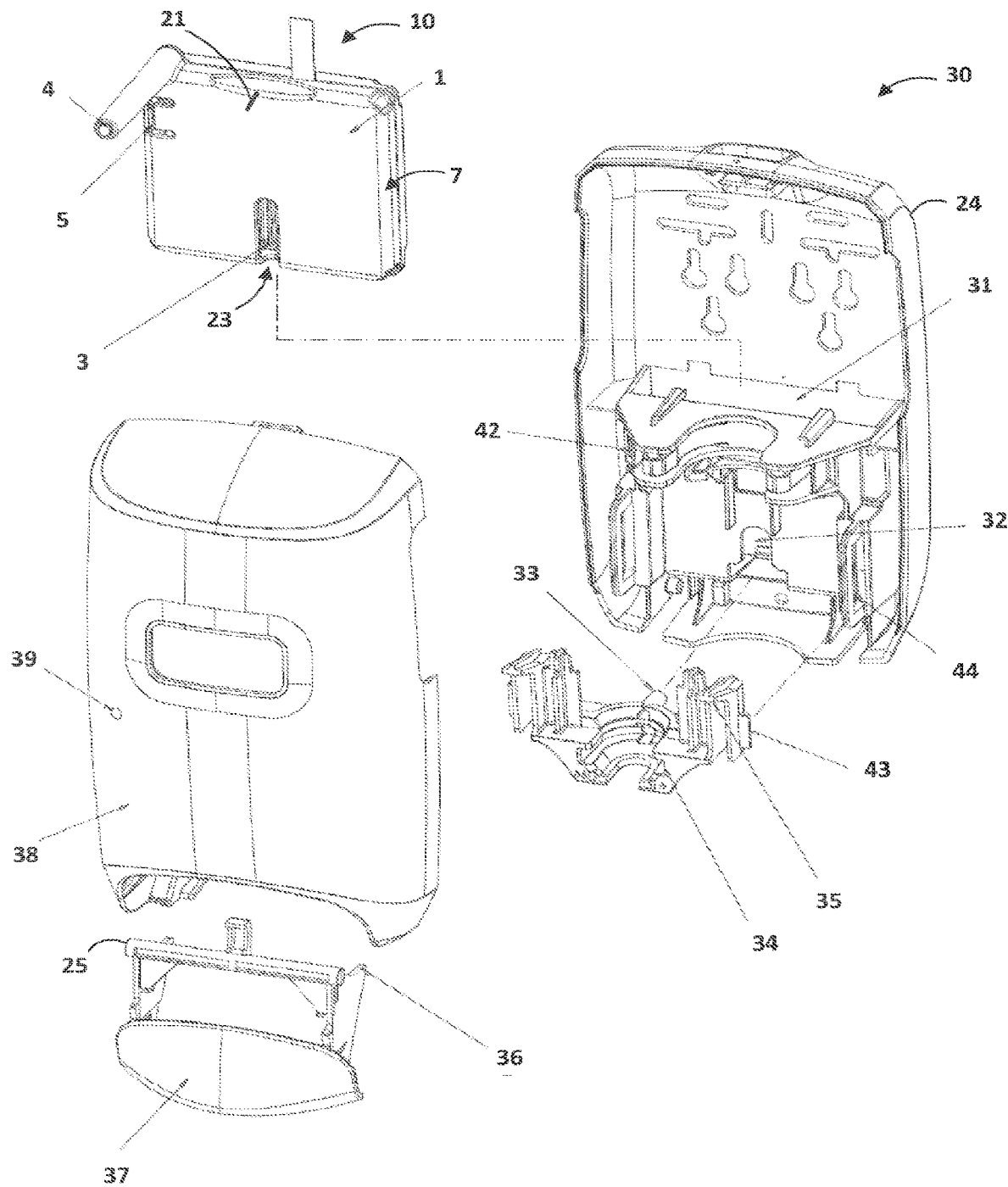
FIGS. 5A and 5B show exploded views of an example manual dispenser and example manual dispenser beacon modules.
Figure 5B:
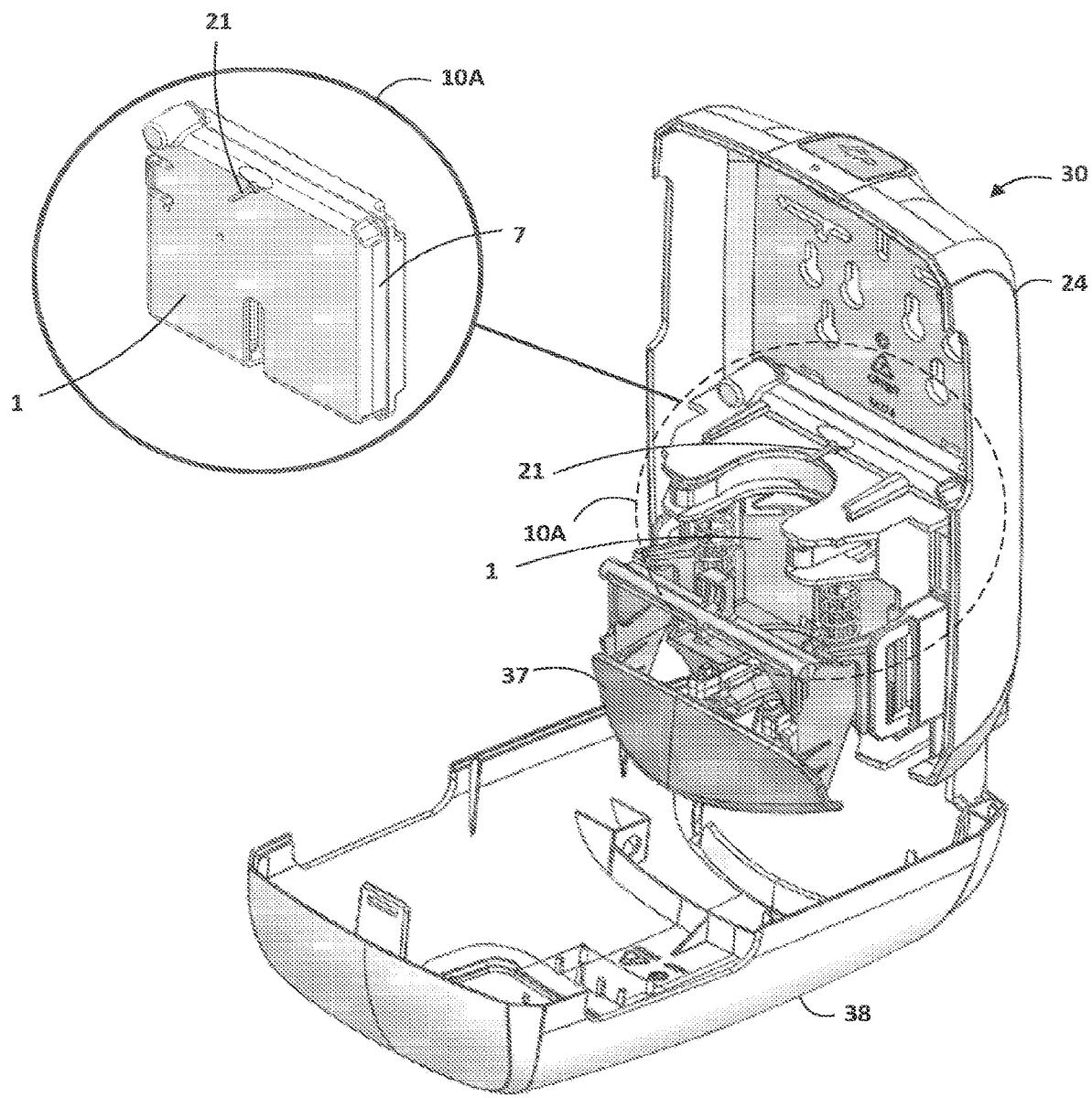

Pull strap 6 is fastened to module base 1 and provides for removal of module 10 from a manual dispenser (see FIG. 5A). PCB assembly 15 includes range adjustment buttons 16 that may be accessed through holes 9 in the module cover 2 (see FIG. 2). LED indicator 4 is connected to PCB 15 through LED tube 18 and is seated at a distal end 22 of LED tube 18. This permits LED indicator 4 to be exposed through the front cover of a manual dispenser 30 as shown in FIG. 5A. In another example, a manual dispenser beacon module 10A as shown in FIG. 5B does not include an LED light tube or LED indicator.

When the pushbar (see ref. num. 37, FIGS. 5A and 5B) is pressed by a user to dispense product, the mechanical movement of the pushbar is converted to an electrical signal by actuation slider 3 and micro switch 19, which initiates a communication sequence between the electronic components of PCB assembly 15 and other components of the beacon module. Actuation slider 3 includes a flat portion 28, a spring engagement portion 11, and a ramp portion 26 connected between the flat portion 28 and spring engagement portion 11. Switch 19 is connected and communicates with PCB assembly 15. When actuation slider 3 is at rest (FIG. 3), switch 19 is positioned with respect to a higher end of ramp portion 26 such that switch 9 is in the open position. When actuation slider 3 is moved toward the closed position (FIG. 4), ramp portion 26 of actuation slider 3 moves over switch 19 until flat portion 28 is positioned over switch 19, thus closing switch 19. This closure of switch 19 communicates to PCB assembly 15 that the dispenser has been actuated. Return spring 27 compresses as actuation slider 3 moves toward the closed position. When the dispenser bottle actuator 34 is released, return spring 27 returns actuation slider 3 to its resting position (FIG. 3).

FIG. 5A shows an exploded view of an example manual dispenser 30 and example manual dispenser beacon module 10. FIG. 5B shows a perspective view of example manual dispenser beacon module 10 installed in manual dispenser 30. Example manual dispenser 30 includes a base 24, a front cover 38 having a LED window 39, and a push bar 37. Push bar 37 snaps into dispenser cover 38. Push bar 37 freely rotates on hinge 25 once manual dispenser 30 is assembled. Manual dispenser 30 further includes a receptacle 31 configured to receive housing 7 of manual dispenser beacon module 10.

Figure 6:
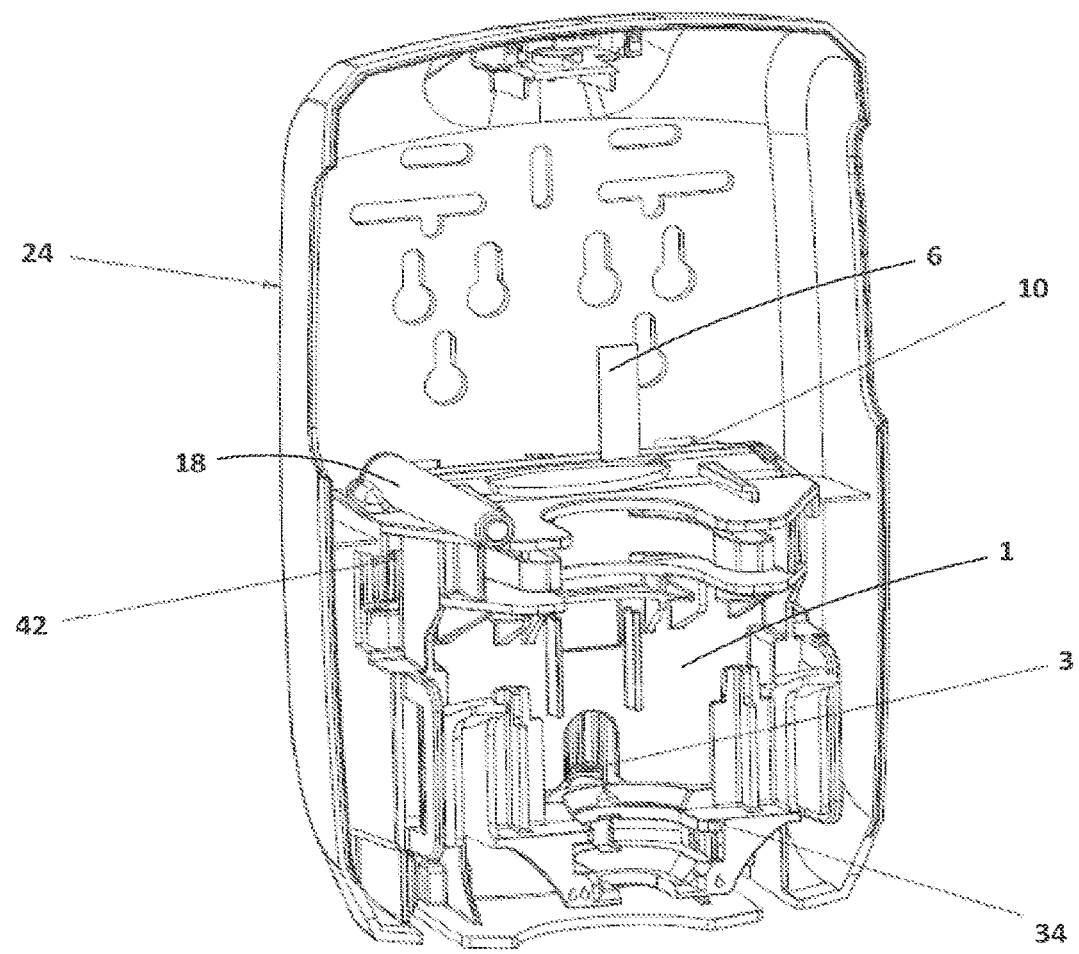
FIG. 6 shows a perspective view of an example manual dispenser beacon module installed in a manual dispenser.

Manual dispenser beacon module 10 is configured to detect actuation of push bar 37 by a user to dispense a quantity of hand hygiene product. Manual dispenser 30 includes a bottle actuator 34 that includes slider ribs 43 that snap into mating slots 44. These features are symmetrical on both sides of dispenser base 24. Bottle actuator 34 includes a slot 32 configured to align with slot 23 of module 10) and thus allow engagement of activation slider 3 with module interface post 33 (FIG. 6). Bottle actuator 34 includes its own return springs (not shown) to return actuator 34 to its resting position.

When manual dispenser beacon module 10 is installed within manual dispenser 30, that is, when housing 7 is received within receptacle 31 of manual dispenser 30, actuation slider 3 is actuated by a module interface post 33 on bottle actuator 34. Push bar lifting ribs 36 rest against lift journals 35 on bottle actuator 34. When push bar 37 is activated by a user, lifting ribs 36 press up against lift journals 35, raising the bottle actuator 34 in slots 44, and raising module interface post 33. Interface post 33 engages the activation slider 3, lifting it to activate switch 19 and send an actuation signal to a processor on PCB assembly 15 indicating that the dispenser has been actuated.

When module 10 is installed in dispenser 30 (in this example, when housing 7 is received within receptacle 31), module-side locking mechanism 5 locks module 10 to dispenser base 24 at a dispenser-side locking mechanism 42. In addition, LED indicator 4 lines up with light pipe 39 on dispenser cover 38. Indicator 4 is the visual interface with the user. A processor (see FIG. 15) on PCB assembly 15 receives the actuation signal from switch 19 and causes indicator 4 to be illuminated each time actuation of push bar 37 is detected. Once assembled, to remove module 10, locking mechanism 5 is pressed at the same time the user pulls on the release strap 6. This allows access to the batteries by removing battery door 8.

Manual dispenser beacon module 10 further includes a bottle detection switch (or bottle presence trigger) 21. Bottle presence trigger 21 is configured to be depressed or moved to the closed position when a product bottle is installed or received in the hand hygiene product dispenser. In this example, bottle presence trigger 21 is implemented using a plunger or pin switch; however, it shall be understood that any other type of switch configured to detect bottle presence could be used. When no bottle is installed in dispenser 30, bottle presence trigger 21 is not depressed (open). When a bottle of hand hygiene product is installed into manual dispenser 30, the neck of the product bottle will depress bottle presence trigger 21. When the bottle presence trigger is thus closed, switch 21 communicates a bottle present signal to the PCB assembly 15 and thus communicates to the processor on PCB assembly 15 that a bottle is installed in the dispenser. When the bottle is removed, bottle presence trigger 21 returns to its open position, communicating to PCB assembly 61 (and thus the processor thereon) that the bottle 80 has been removed. Bottle presence or absence information may be communicated as part of the dispenser data from the module 50 along with each dispense event and a count of the total number of dispense since bottle replacement.

Inclusion of a product bottle detection feature such as bottle presence trigger 21 allows tracking of the replacement of hand hygiene product in the dispenser, so the system can determine when product needs to be replaced and also that the product is replaced at the appropriate time. For example, a time/date stamped event may be recorded when a product bottle has been taken out of a dispenser (e.g., when the switch is opened) and another event may be recorded when a product bottle has been replaced into the dispenser (e.g., when the switch is closed). The module 50 or a remote computing system may count the number of dispenses since bottle replacement (e.g., a switch opening event followed by a subsequent switch closing event), and may count down the number of events to a predetermined "alert" level for replacement. The module 50 or a remote computing system may compare the number of dispense events that occurred at the time of bottle replacement to the predetermined alert level to determine whether the product bottle was replaced too early, thus possibly wasting hand hygiene product by incomplete emptying of the product bottle. Bottle presence trigger 21 also allows for the module 50 (or a remote computing system) and hand hygiene compliance personnel to identify when a dispenser is being used without any hand hygiene product (e.g., when actuation of the hand hygiene product dispenser is detected but the bottle presence switch is not closed). The module 50 or the remote computing system may generate an alert to communicate to hand hygiene compliance personnel that the hand hygiene product dispenser is being used without any hand hygiene product and to inform them that product needs to be installed in that particular dispenser.

Figure 8:
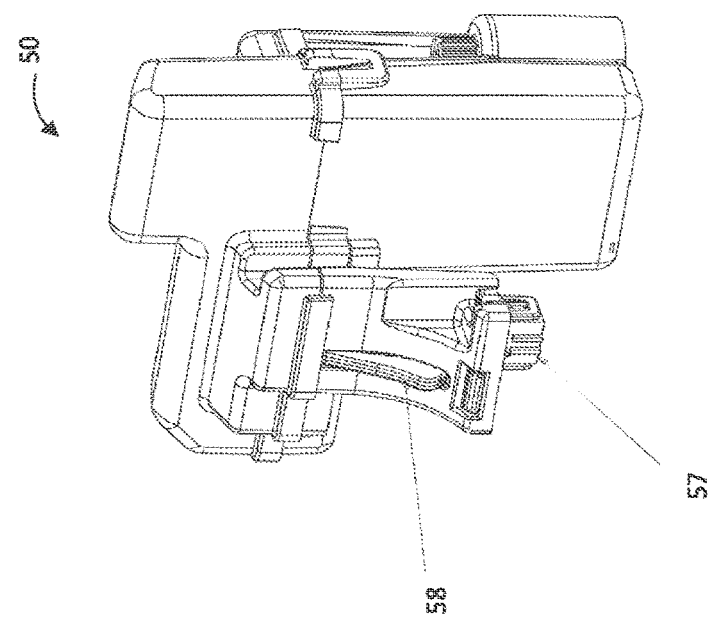
FIGS. 7 and 8 show a front perspective view and a back perspective view, respectively, of an example touch free dispenser beacon module.
Figure 7:
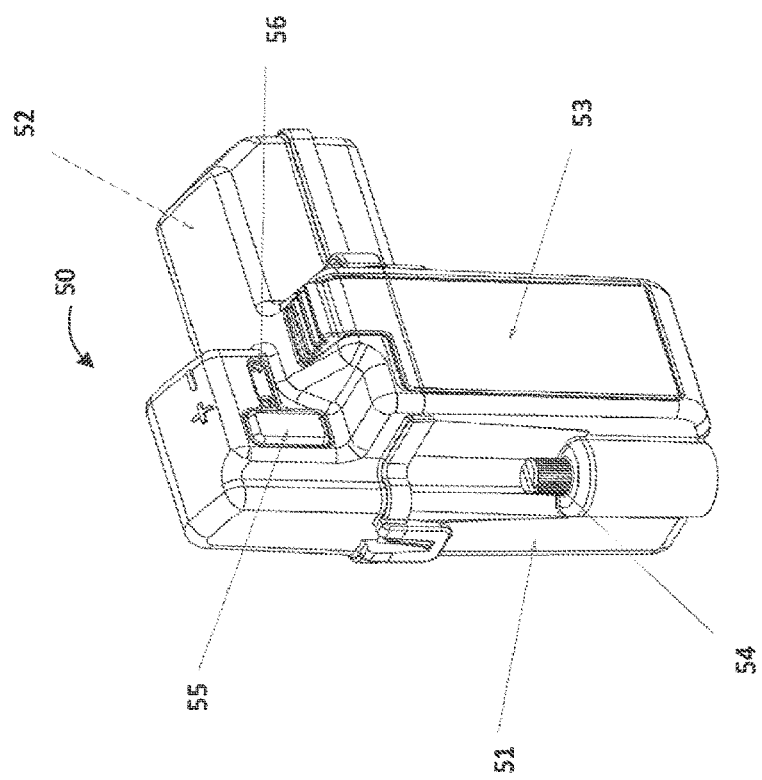

FIGS. 7 and 8 show a front perspective view and a back perspective view, respectively, of an example touch free dispenser beacon module 50. Touch free dispenser beacon module 50 is configured to be used with a touch free hand hygiene product dispenser to monitor hand hygiene events associated with the dispenser, and to wirelessly transmit hand hygiene data (including data concerning the monitored hand hygiene events) to or from the touch free dispenser 50. Touch free dispenser beacon module 50 includes a module base 51, a module cover 52, a battery door 53, a captive mounting screw 54, a firmware access port 55, a connector 57, and a bottle presence trigger 58 (implemented using a rocker arm assembly in this example).

In some examples, the touch free dispenser beacon module 50 is further configured to wirelessly transmit and/or receive communication from one or more computing device (s). For example, the beacon module 50 may receive remote software updates, remote configuration settings (e.g., range settings, product empty settings, settings for a number of dispense events before a product bottle should be refilled or replaced, etc.) from one or more computing devices. The beacon module 50 may further communicate with one or more other beacon modules in a healthcare setting, such as those associated with other dispensers, with motion detectors in a patient room or other defined area, with patient zone beacons in a patient room or other defined area, or other such devices in a healthcare setting that may be useful for monitoring of hand hygiene compliance. The beacon module 50 may be further configured to wirelessly communicate (both transmit and receive) with one or more uniquely assigned healthcare worker identification badges. For example, the beacon module 50 may be configured to communicate with a badge, obtain healthcare worker identification information from the badge, and associate a detected dispense event with the healthcare worker identification information.

Figure 10:
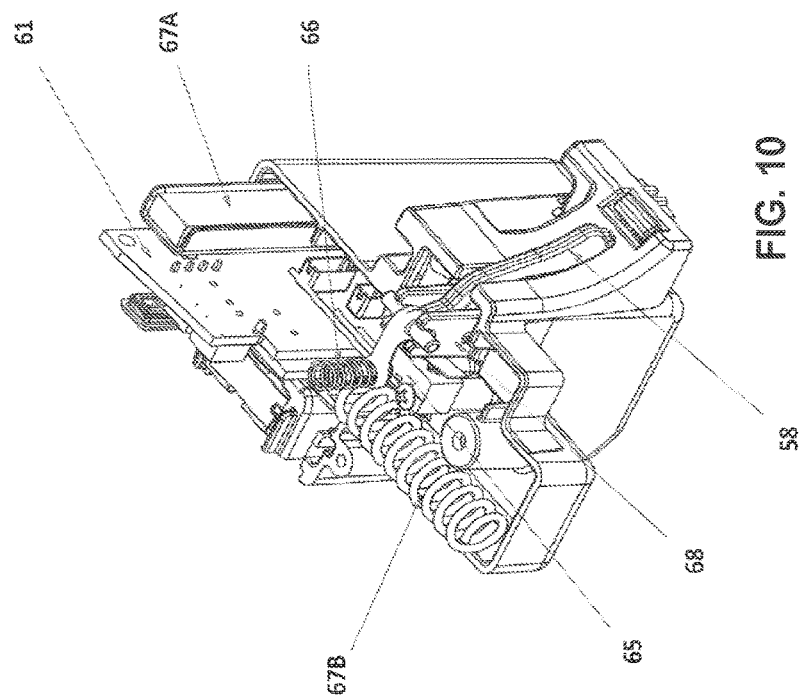
FIGS. 9 and 10 show a front perspective view and a back perspective view, respectively, of the internal components of example touch free dispenser beacon module with the module cover removed.
Figure 9:
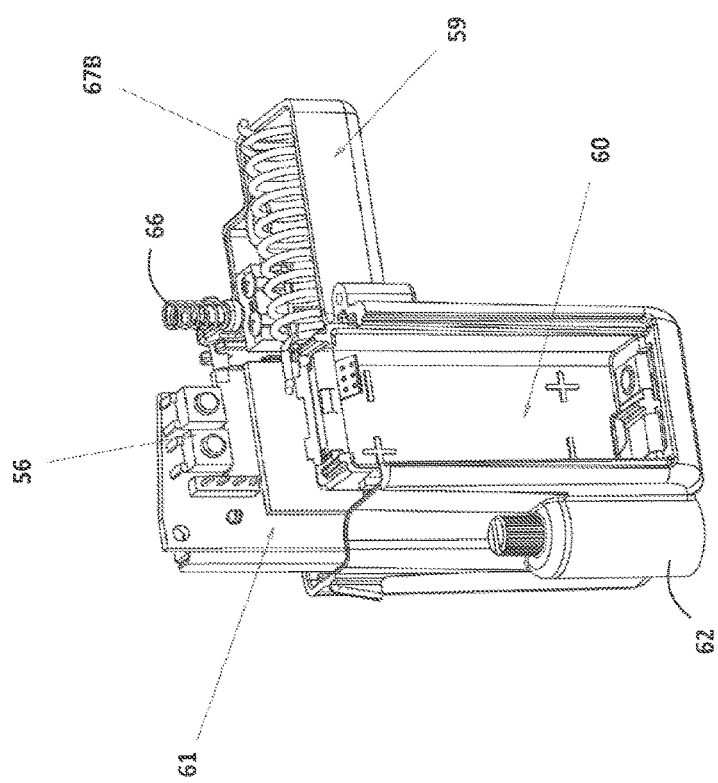

FIGS. 9 and 10 show a front perspective view and a back perspective view, respectively, of the internal components of example touch free dispenser beacon module 50 with module cover 52 removed. Touch free dispenser beacon module 50 includes a battery enclosure 60, a PCB assembly 61 including a controller (see FIG. 16), bottle presence trigger 58, bottle detection micro switch 65, rocker return spring 66, and connector/rocker retainer 68. PCT assembly 61 includes two antennas, a high frequency antenna 67A and a low frequency coil antenna 67B. Range buttons 56 are accessed through holes in module cover 52. In this example, range buttons 56 adjust the range of low frequency antenna 67A.

Battery enclosure 60 is connected to, and provides power to PCB assembly 61. In this example, touch free dispenser beacon module 50 is powered using 2 AA batteries. However, it shall be understood that other means of powering module 50 may be used, and that the disclosure is not limited in this respect. In other examples, manual dispenser beacon module may be powered using different types of batteries, may be hard-wired to the electrical system of the building, may receive power from the batteries or the controller of the touch free dispenser.

Dispenser/module communication connector 57 communicatively couples PCB assembly 61 (and thus the touch free dispenser beacon module controller) with the controller of a touch free dispenser.

Inclusion of a bottle detection feature such as bottle presence trigger 58 allows tracking of the replacement of hand hygiene product in the dispenser, so the beacon module 150 or a remote computing device or system can determine when hand hygiene product needs to be replaced. For example, a time/date stamped event may be recorded when a product bottle has been taken out and another time/date stamped event may be recorded when the product bottle has been replaced. The module or the system may count the number of dispenses since product bottle replacement, and may count down the number of events to a predetermined "alert" level for replacement. Bottle presence trigger 58 also allows for hand hygiene compliance personnel to identify when a dispenser is being used without any hand hygiene product, so that the likelihood of dispensers being used without any hand hygiene product is reduced. In general, some or all of the functionality described above with respect to the bottle detection feature of the manual hand hygiene product dispenser may also be implemented by the bottle detection feature of the touch free hand hygiene product dispenser.

Figure 16:
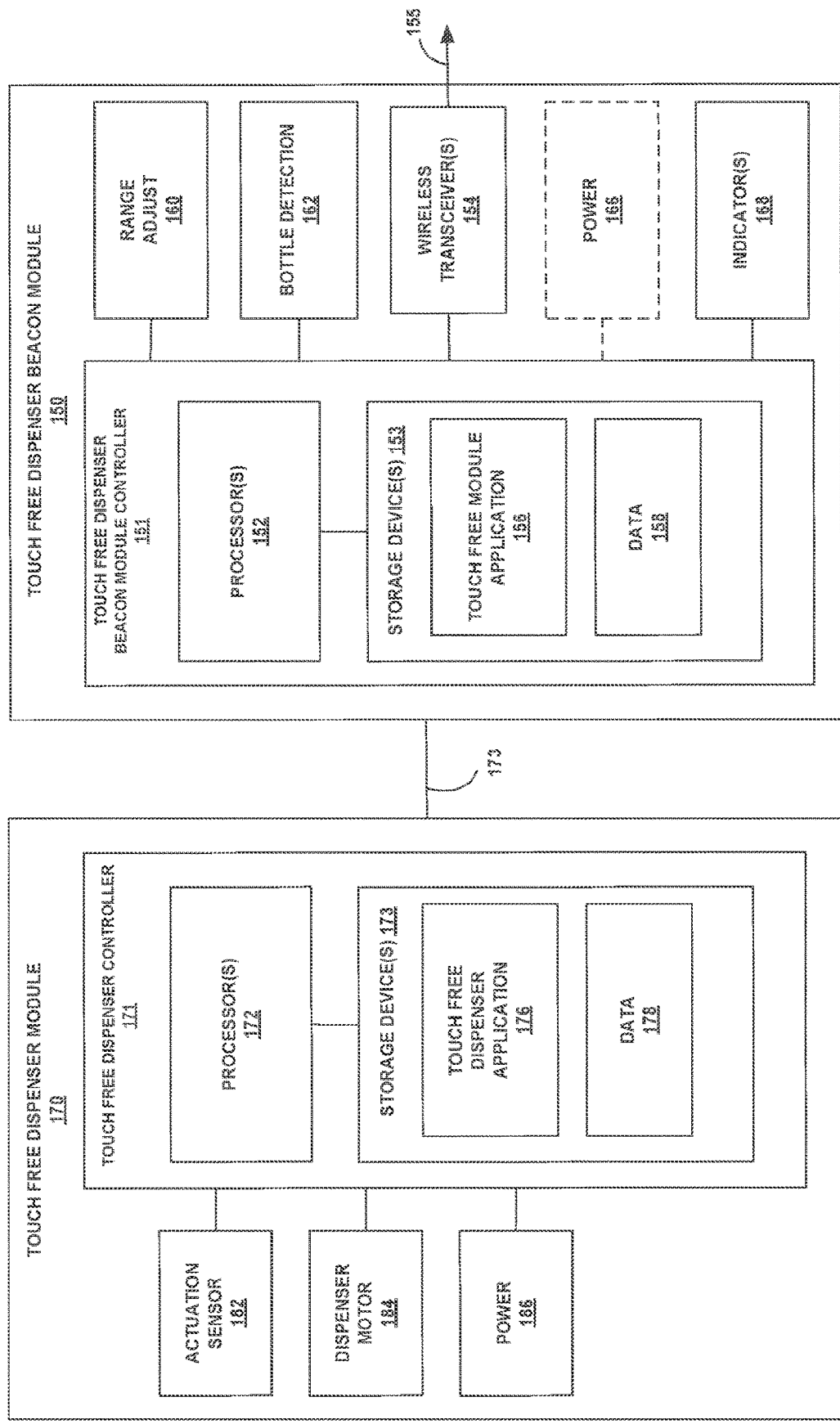
FIG. 16 is a block diagram illustrating an example implementation of a touch free dispenser beacon module.

FIGS. 11A, 11B and 12-14 show various views of portions of an example touch free dispenser 70 and a touch free dispenser beacon module 50. Touch free dispenser 70 includes a base 71, a cover 73, and an electromechanical gearbox 73 that includes a communications connector 77. Communications connector 77 communicatively couples touch free dispenser controller (see FIG. 16) with the touch free dispenser beacon module controller (see FIG. 16). The touch free dispenser controller manages operation of touch free dispenser 70, and includes a signal output indicative of actuation of the touch free dispenser, which is communicated to the touch free dispenser beacon module controller via the interface of connectors 57/77 as shown in FIG. 16. Base 71 of touch free dispenser 70 includes a mounting boss 72 that mates with a mounting receiver 62 on touch free module 50.

Figure 11A:
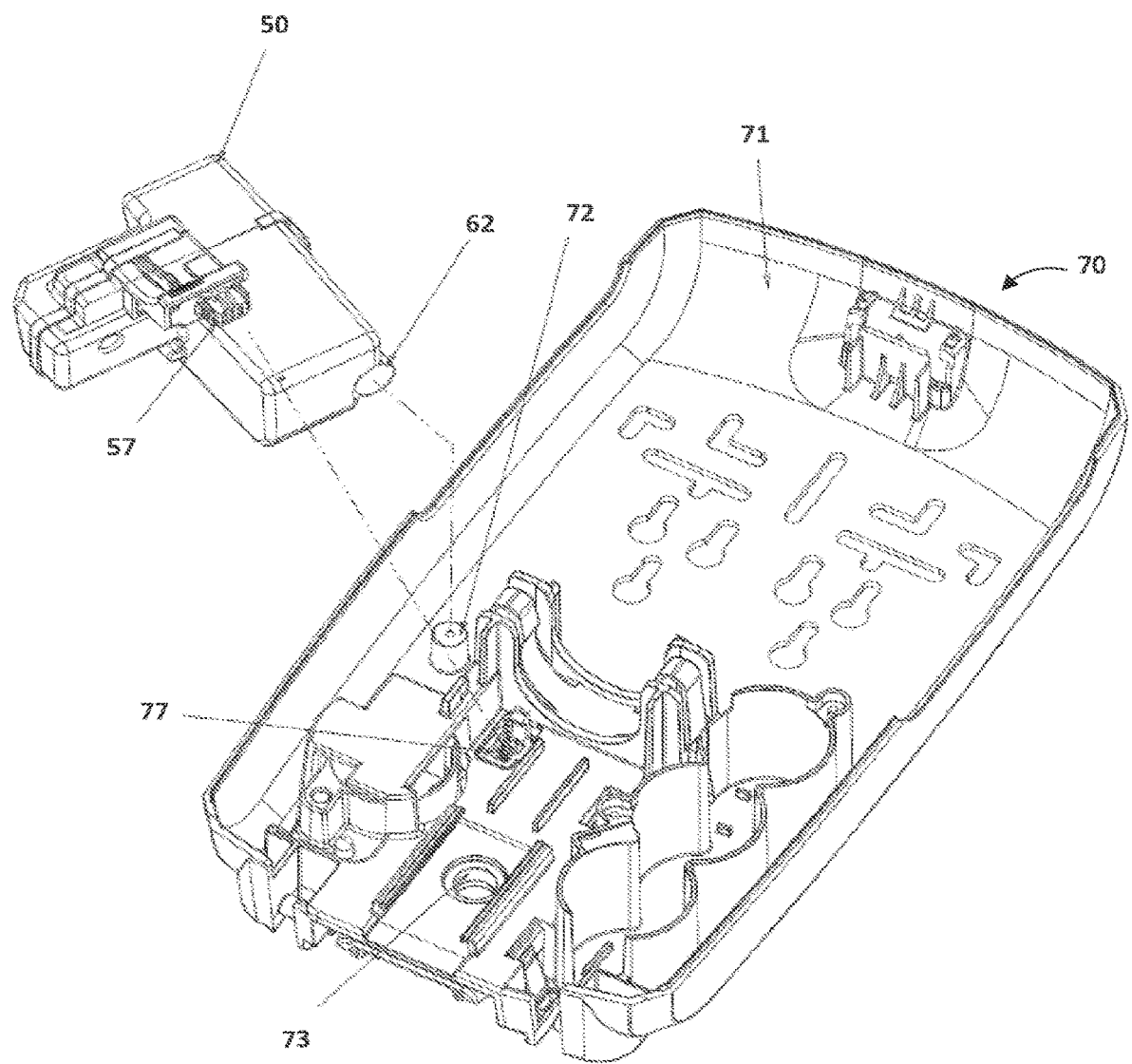
FIGS. 11A, 11B and 12-14 show various views of portions of an example touch free dispenser with its cover removed and a touch free dispenser beacon module.
Figure 11B:
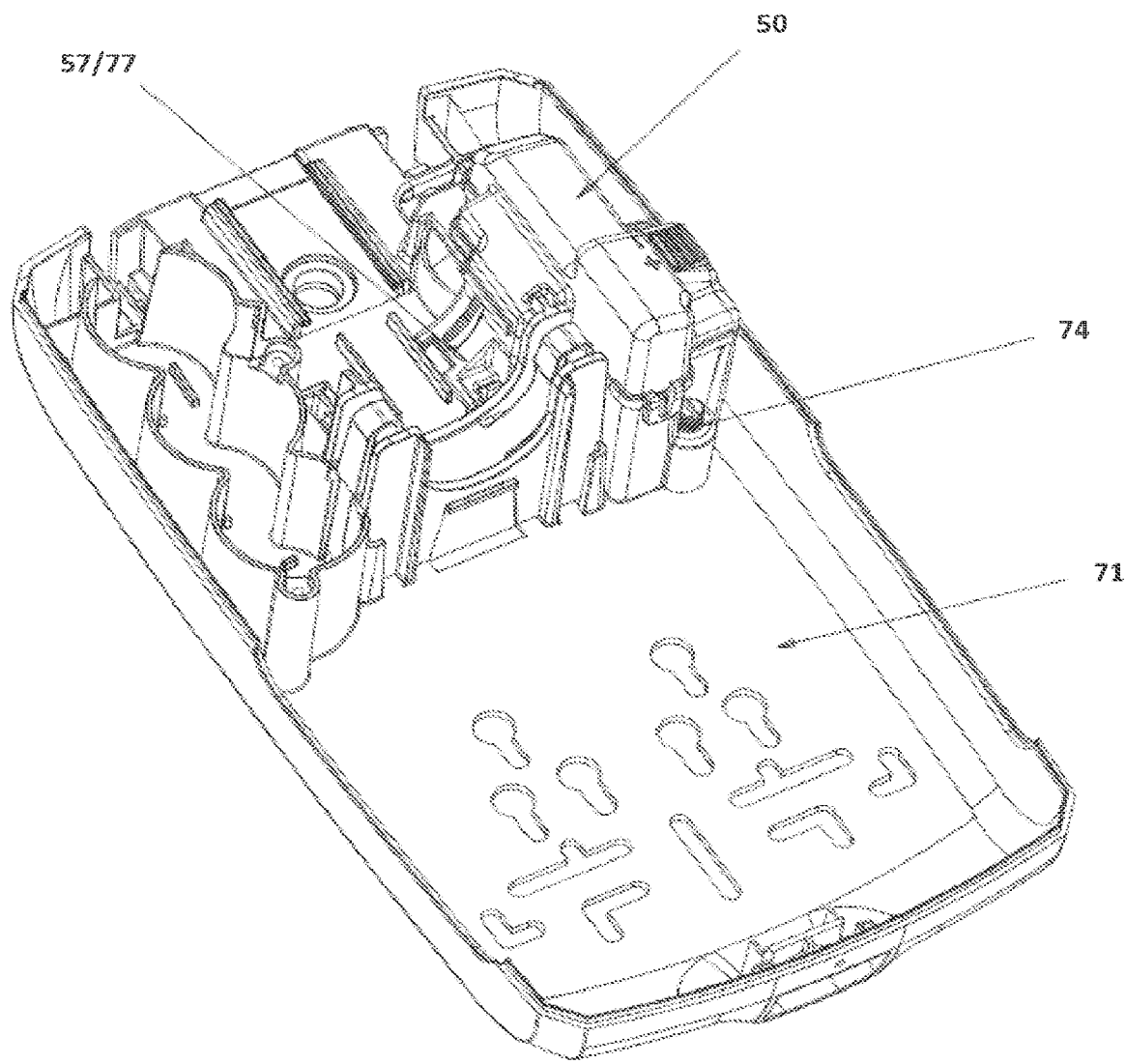
Figure 12:
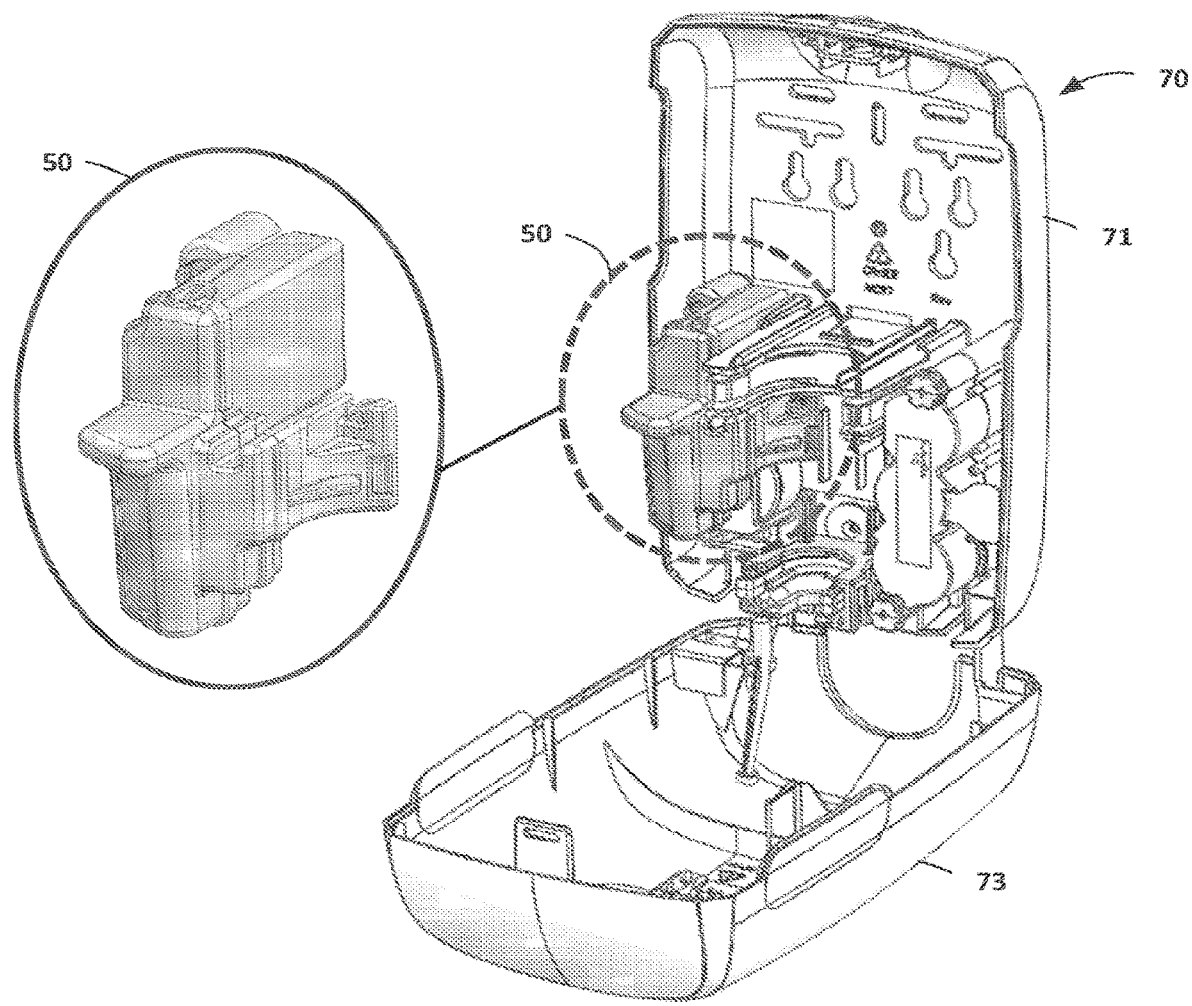
Figure 13:
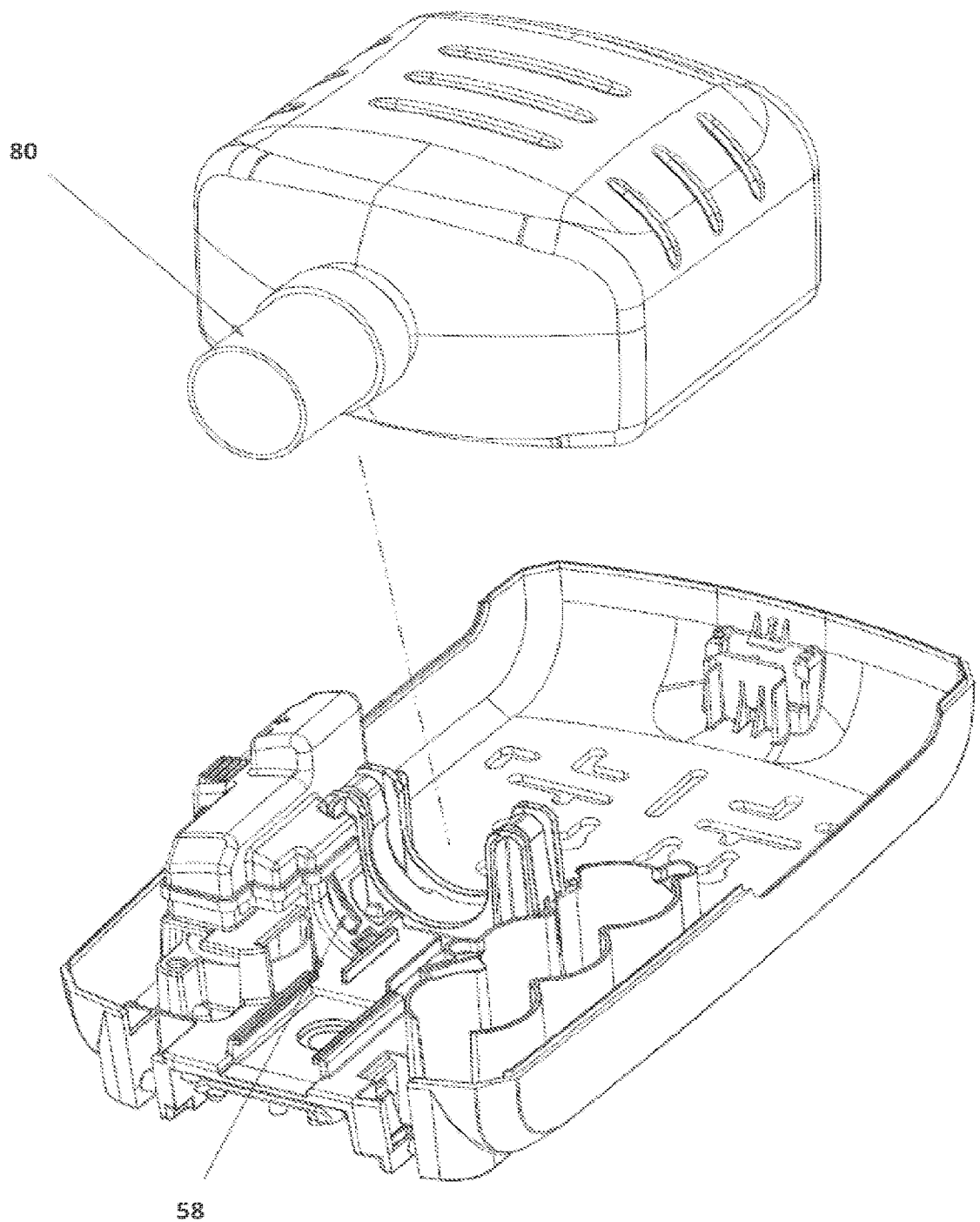
Figure 14:
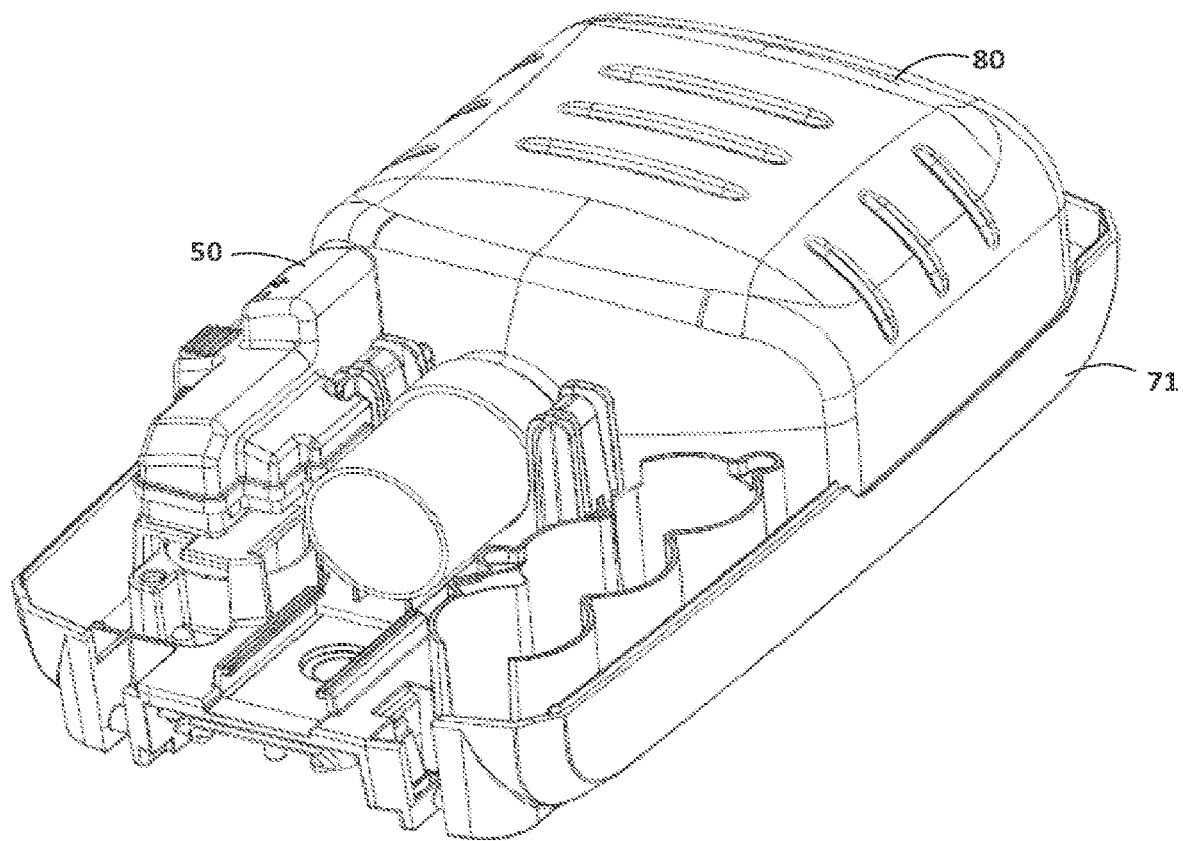

When touch free module 50 is installed into base 71 of touch free dispenser 70, as shown in FIGS. 11B and 12, connector 57 on touch free beacon module 50 is connected with connector 77 of the touch free dispenser controller, allowing dispenser controller and dispenser beacon module 50 to communicate. A mounting screw 74 may fit over the mating mounting boss 72 and fastens touch free module 50 to touch free dispenser 70.

When there is no bottle installed in touch free dispenser 70, bottle detection rocker arm 58 is spring loaded by rocker return spring 66, compressing on the inside of module cover 52. When the system is at rest (i.e., no bottle installed in the dispenser), bottle detection micro switch 65 is not pressed. When a bottle 30 is installed (FIGS. 13 and 14) the neck of the product bottle 80 presses and rotates rocker arm 58, depressing micro switch 65. Switch 65 communicates to the PCB assembly 61 that a bottle is installed. When the bottle 80 is removed, rocker arm 58 returns to its spring-loaded position releasing bottle detection micro switch 65, communicating to PCB assembly 61 that the bottle 80 has been removed.

Figure 15:
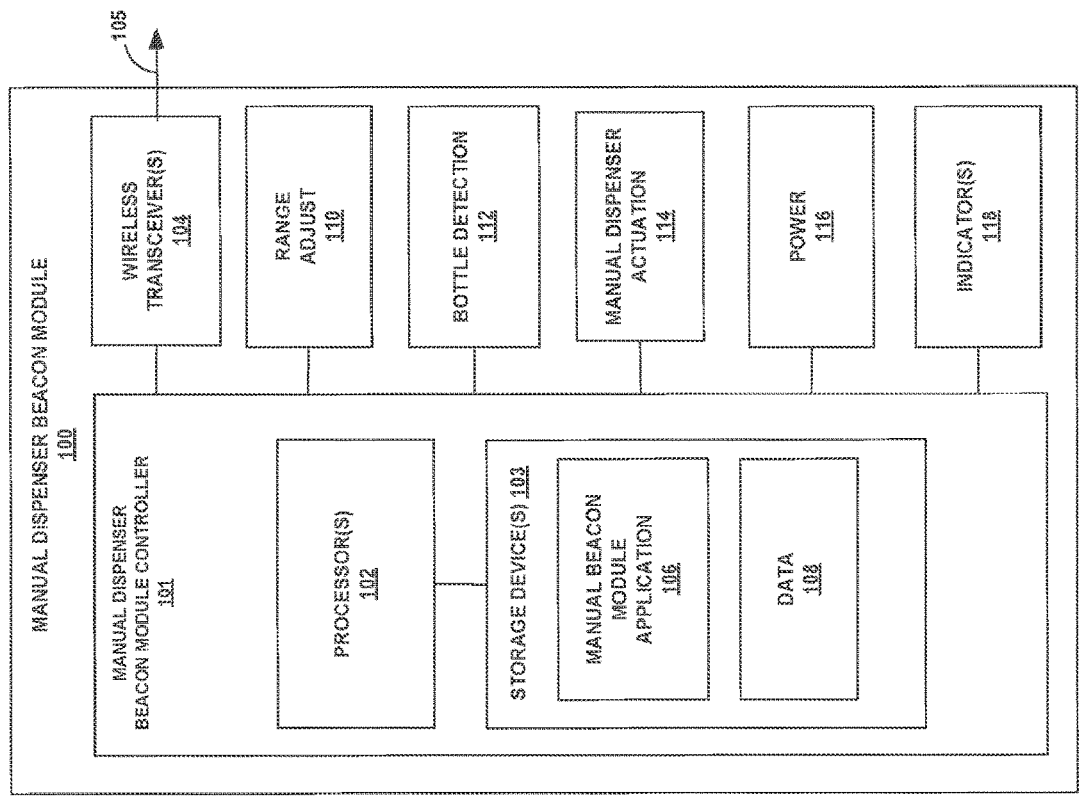
FIG. 15 is a block diagram illustrating an example implementation of the electronic components of a manual dispenser beacon module.

FIG. 15 is a block diagram illustrating an example implementation of the electronic components of a manual dispenser beacon module 100. In this example, manual dispenser beacon module 100 includes a controller 101 that includes one or more processors 102 and storage device(s)/media 103. Processors 102, in one example, are configured to implement functionality and/or process instructions for execution within manual dispenser beacon module 100. For example, processors 102 may execute instructions stored in storage devices 103. Examples of processors 102 may include, any one or more of a microprocessor, a controller, a digital signal processor (DSP), an application specific integrated circuit (ASIC), a field-programmable gate array (FPGA), or equivalent discrete or integrated logic circuitry, including other hardware processors.

Example manual dispenser beacon module 100 further includes one or more wireless transceiver(s) 104, range adjustment buttons 110, a bottle detection switch 112, a manual dispenser actuation switch 114, a power supply 116, and one or more audible of visual indicators 118.

In some examples, the wireless transceiver(s) 104 of manual dispenser beacon module 100 is further configured to wirelessly transmit and/or receive communication from one or more computing device(s). For example, the beacon module 100 may receive remote software updates, remote configuration settings (e.g., range settings, product empty settings, settings for a number of dispense events before a product bottle should be refilled or replaced, etc.) from one or more computing devices. The beacon module 100 may further communicate with one or more other beacon modules in healthcare setting, such as those associated with other dispensers, with motion detectors in a patient room or other defined area, with patient zone beacons in a patient room or other defined area, or other such devices in a healthcare setting that may be useful for monitoring of hand hygiene compliance. The beacon module 100 may be further configured to wirelessly communicate (both transmit and receive) with one or more uniquely assigned healthcare worker identification badges. For example, the beacon module 100 may be configured to communicate with a badge, obtain healthcare worker identification information from the badge, and associate a detected dispense event with the healthcare worker identification information.

One or more storage devices 103 may be configured to store information within manual dispenser beacon module controller. Storage devices 103, in some examples, can be described as a computer-readable storage medium. In some examples, storage devices 103 are a temporary memory, meaning that a primary purpose of storage devices 103 is not long-term storage. Storage devices 103, in some examples, may be described as a volatile memory, meaning that storage devices 103 do not maintain stored contents when the computer is turned off. Examples of volatile memories include random access memories (RAM), dynamic random access memories (DRAM), static random access memories (SRAM), and other forms of volatile memories known in the art. In some examples, storage devices 103 are used to store program instructions for execution by processors 102, such as manual module application 106. Storage devices 103, in one example, are used by software or application 156 running on controller 101 to temporarily store information during program execution.

Storage devices 103, in some examples, also include one or more computer-readable storage media. Storage devices 103 may be configured to store larger amounts of information than volatile memory. Storage devices 103 may further be configured for long-term storage of information. In some examples, storage devices 103 may include non-volatile storage elements. Examples of such non-volatile storage elements include magnetic flash memories, or forms of electrically programmable memories (EPROM) or electrically erasable and programmable memories (EEPROM).

Storage device(s) 103 may store program instructions, such as touch free module application 156, for execution by processors 102. Manual module application 106 includes instructions that, when executed by processors 102, allow controller 101 to implement the manual dispenser beacon module functionality, such as monitor dispense events occurring at the manual free dispenser, store dispenser data concerning the dispense events, and wirelessly transmit (as indicated by reference numeral 105) the dispenser data via wireless transceiver 104. The dispenser data may include, for example, one or more of a dispenser id, a beacon module id, and a time and date stamp for each dispense event. The dispenser data may further include, for example, a current battery status, a total number of dispense events occurring during a predetermined time interval or since the last time the dispenser was refilled, a number of dispenses remaining before the dispenser runs out of hand hygiene product, an out-of-product or low product status, and/or other dispenser status information, etc.

Storage device(s) 103 may store various data (108) generated or used by processor(s) 102 during execution of the manual module application instructions 106. For example, storage device(s) may generate and store dispense event data, beacon module identification information, battery levels, bottle detection/presence information, range information, or other data associated with the manual dispenser beacon module 100.

Example manual dispenser beacon module 100 receives, for example, an indication of actuation of the manual dispenser from manual dispenser actuation switch 114. One example implementation for switch 114 is switch 19 of FIGS. 3 and 4. However, it shall be understood that other implementations and mechanisms for detecting actuation of a manual dispenser may be used, and that the disclosure is not limited in this respect. Controller 101 may store information concerning the received indication as a dispense event in data storage 108. In some examples, controller 101 may attach a time and date stamp, dispenser identification information and/or beacon module identification information to the dispense event data. Controller 101 may wirelessly transmit (as indicated by reference numeral 105) via wireless transceiver(s) 104 the dispense event data upon receipt of each indication of a manual actuation, or may wirelessly transmit (as indicated by reference numeral 105) multiple dispense events on a periodic basis or on demand. In other examples, controller 101 wirelessly transmits (as indicated by reference numeral 105) via wireless transceiver(s) 104 dispenser data indicative of a dispense event upon receipt of each indication of dispenser actuation from manual dispenser actuation without appending a time and date stamp. A computing device configured to receive dispenser data from multiple manual and/or touch free dispenser beacon modules within a healthcare or other facility may associate each dispense event with a time and date stamp, and may analyze the dispense event data to monitor hand hygiene within the facility.

When beacon module 100 in installed in a manual hand hygiene product dispenser and a bottle is installed into the dispenser, bottle detection switch 112 (such as switch 21 in FIGS. 1 and 5) is depressed (closed) and switch 112 generates a bottle present signal, which is in turn received by the beacon module controller 101. As long as a product bottle remains installed in the dispenser, the switch 112 remains closed and beacon module controller 101 may store the bottle present information in data store 108. If the bottle is removed, the switch 112 will return to the resting (open) state and the bottle present signal will no longer be present. Beacon module controller 101 may store information that no bottle is present in data store 108. Manual beacon module application 106 may cause processor(s) 103 to determine whether a bottle is present in the dispenser each time a dispense event occurs, and may wirelessly transmit the bottle present information as part of the dispenser data each time a dispense event occurs. In this way, users may be informed as to whether a hand hygiene product is actually installed in the dispenser, and may take remedial measures (refill the dispenser with a product bottle) if the dispenser data indicates that no bottle is present.

FIG. 16 is a block diagram illustrating an example implementation of a touch free dispenser beacon module 150. In this example, touch free dispenser beacon module 150 further includes a controller 151 that includes one or more processors 152 and storage device(s)/media 153. Processors 152, in one example, are configured to implement functionality and/or process instructions for execution within touch free dispenser beacon module 150. For example, processors 152 may be capable of processing instructions stored in storage devices 153. Examples of processors 152 may include, any one or more of a microprocessor, a controller, a digital signal processor (DSP), an application specific integrated circuit (ASIC), a field-programmable gate array (FPGA), or equivalent discrete or integrated logic circuitry, including other hardware processors.

Example touch free dispenser beacon module 150 further includes one or more wireless transceiver(s) 154, range adjustment buttons 160, a bottle detection switch 162, a power supply 166, and one or more audible of visual indicators 168.

In some examples, the wireless transceiver(s) 154 of touch free dispenser beacon module 150 is further configured to wirelessly transmit and/or receive communication from one or more computing device(s). For example, the beacon module 150 may receive remote software updates, remote configuration settings (e.g., range settings, product empty settings, settings for a number of dispense events before a product bottle should be refilled or replaced, etc.) from one or more computing devices. The beacon module 150 may further communicate with one or more other beacon modules in healthcare setting, such as those associated with other dispensers, with motion detectors in a patient room or other defined area, with patient zone beacons in a patient room or other defined area, or other such devices in a healthcare setting that may be useful for monitoring of hand hygiene compliance. The beacon module 150 may be further configured to wirelessly communicate (both transmit and receive) with one or more uniquely assigned healthcare worker identification badges. For example, the beacon module 150 may be configured to communicate with a badge, obtain healthcare worker identification information from the badge, and associate a detected dispense event with the healthcare worker identification information.

One or more storage devices 153 may be configured to store information within touch free dispenser beacon module controller. Storage devices 153, in some examples, can be described as a computer-readable storage medium. In some examples, storage devices 153 are a temporary memory, meaning that a primary purpose of storage devices 153 is not long-term storage. Storage devices 153, in some examples, may be described as a volatile memory, meaning that storage devices 153 do not maintain stored contents when the computer is turned off. Examples of volatile memories include random access memories (RAM), dynamic random access memories (DRAM), static random access memories (SRAM), and other forms of volatile memories known in the art. In some examples, storage devices 153 are used to store program instructions for execution by processors 152, such as touch free module application 156. Storage devices 153, in one example, are used by software or application 156 running on controller 151 to temporarily store information during program execution.

Storage devices 153, in some examples, also include one or more computer-readable storage media. Storage devices 153 may be configured to store larger amounts of information than volatile memory. Storage devices 153 may further be configured for long-term storage of information. In some examples, storage devices 153 may include non-volatile storage elements. Examples of such non-volatile storage elements include magnetic flash memories, or forms of electrically programmable memories (EPROM) or electrically erasable and programmable memories (EEPROM).

Storage device(s) 153 may store program instructions, touch free module application 156, for execution by processors 152. Touch free module application 156 includes instructions that, when executed by processors 152, allow controller 151 to implement the touch free dispenser beacon module functionality, such as monitor dispense events occurring at the touch free dispenser, store dispenser data concerning the dispense events, and wirelessly transmit the dispenser data via wireless transceiver 154. The dispenser data may include, for example, one or more of a dispenser id, a beacon module id, and a time and date stamp for each dispense event. The dispenser data may further include, for example, a current battery status, a total number of dispense events occurring since a predetermined time interval or since the last time the dispenser was refilled, a number of dispenses remaining before the dispenser runs out of hand hygiene product, an out-of-product or low product status, and/or other dispenser status information, etc.

Storage device(s) 153 may store various data (158) generated or used by processor(s) 152 during execution of the touch free module application instructions 156. For example, storage device(s) may generate and store dispense event data, beacon module identification information, battery levels, bottle detection data, range information, or other data associated with the touch free dispenser beacon module 150.

Example touch free dispenser beacon module 150 electronically communicates with a touch free dispenser module 170 via communication link(s) 171. Touch free dispenser module 170 includes a touch free dispenser controller 171 that executes instructions stored on storage device(s) 173 to manage and control operation of a touch free dispenser, such as touch free dispenser 70. Dispenser controller 171 includes one or more processor(s) 172 and storage device(s) 173. A touch free dispenser application 176 stored in storage media 173 includes instructions that when executed by processors 172, implement control of the functionality for the touch free dispenser. Storage devices 173 may further include data 178 that is used or generated during execution of touch free dispenser application 176.

Touch free dispenser module 170 further includes an actuation sensor 182 that senses actuation of the touch free dispenser and generates a corresponding actuation signal that is in turn received by controller 171. Actuation sensor 182 may include, for example, one or more of a photo interrupter, an infrared sensor, an optical sensor, a motion sensor, or other touchless or touch free mechanism for detecting presence of a user's hands. Touch free dispenser 170 further includes a dispenser motor 184 that is activated by controller 171 upon receipt for the actuation signal, thus causing a standardized dose of hand hygiene product to be dispensed from the touch free dispenser.

Communication link(s) 173 may be implemented in the example of FIGS. 11 and 12 via connectors 57/77. In this way, controller 151 of beacon module 150 receives, for example, an indication of touch free dispenser actuation from touch free dispenser controller 171 via communication link(s) 173. Controller 151 may store information concerning the received indication as a dispense event. In some examples, controller 151 may attach a time and date stamp, dispenser identification information and/or beacon module identification information to the dispense event data. Controller 151 may wirelessly transmit (as indicated by reference numeral 155) via wireless transceivers 154 the dispense event data upon receipt of each indication of a manual actuation, or may wirelessly transmit (as indicated by reference numeral 155) multiple dispense events on a periodic basis or on demand. In other examples, controller 151 wirelessly transmits (as indicated by reference numeral 155) via wireless transceivers 154 dispenser data indicative of a dispense event upon receipt of each indication of dispenser actuation from touch free dispenser controller without appending a time and date stamp. A computing device configured to receive dispenser data from multiple manual and/or touch free dispenser beacon modules within a healthcare or other facility may associate each dispense event with a time and date stamp, and may analyze the dispense event data to monitor hand hygiene within the facility.

Power source 166 is indicated in dashed lines to indicate that beacon module 150 power may alternatively by powered from touch free dispenser module 170. In such an example, instead of having dedicated batteries/power source 166, touch free dispenser beacon module 150 may be configured to receive power from the touch free dispenser 70. For example, controller 151 may receive power from touch free dispenser controller 170 via communication link(s) 173. This may reduce the overall physical size of the touch free dispenser beacon module 150, as it would not need to be sized to accommodate one or more batteries within the housing. The physical size and configuration of the housings for dispenser beacon module 50 shown in FIGS. 7-11, for example, may therefore be designed without a battery compartment 60 or battery cover 53, thus reducing the overall external dimensions of beacon module 50 and potentially making it easier to fit within the housing of a touch free dispenser.

In some examples, there may be advantages to the touch free dispenser beacon module to have its own internal batteries. Each time the dispenser activates, a load is placed on the batteries. As the batteries approach the end of their life, their internal resistance increases and the load will cause the battery voltage to "droop" significantly. If the touch free dispenser beacon module is powered by the dispenser's batteries and if the battery voltage droops below the reset voltage threshold of the touch free beacon module controller, the touch free beacon module controller will be held in reset until the battery voltage recovers to a point above the reset threshold. Battery voltage recovery could take long enough to delay badge communication until the end of the dispense cycle. It could also take so long that the user which activated the dispenser has already left the area of the dispenser before the touch free beacon module controller has come out of reset and can communicate with that user's badge. The result may be that the user's badge has not been set to a clean hygienic state and the event is not reported. However, if the touch free beacon module has its own batteries, it is not affected by the voltage droop of the dispenser's batteries during activation and badge communication is more likely to ensue at the beginning of the dispense cycle.

Another benefit may be that a touch free beacon module, with its own batteries, will not reduce the life of the dispenser's batteries thus allowing the dispenser to meet specified battery life expectations. Also, the touch free beacon module may include the ability to monitor the level of the dispenser's batteries as well as its own batteries. It may be able to report the level of the dispenser's batteries even after their voltage has dropped below a level that would not allow the touch free beacon module to function had it been using the dispenser's batteries.

In some examples, a plurality of manual dispenser beacon module(s) 100 and/or touch free dispenser beacon module(s) 150 may be used to monitor hand hygiene compliance in a healthcare setting or other setting in which hand hygiene compliance monitoring is desired. For example, the modular hand hygiene compliance system may be adapted for use in applications such as hotel room cleaning, education facilities, long term care, restaurants, food service, food and beverage facilities, food packing, eating areas, rest rooms, food preparation areas, cooking areas, etc.

In such a system, each healthcare worker (HCW) is assigned a compliance badge that is uniquely associated with the HCW. Each time a HCW dispenses hand hygiene product from one of the manual or touch free dispensers having a manual beacon module 100 or touch free beacon module 150, the corresponding beacon module 100/150 may communicate with the HCW badge, receive HCW identification information from the badge, and associate the HCW identification information with the dispense event. Example dispenser data stored and/or wirelessly transmitted upon each dispenser actuation is shown in Table 1:

TABLE 1

Example Dispenser Data with HCW Badge ID

| | |
|---|---|
| Dispenser ID | 12345678 |
| Dispense event | Yes |
| Time and Date | 12:36:15, 6 MAR. 2015 |
| Badge ID | 9876543AB |
| Bottle presence | Yes |
| Battery level | 92% |
| Range setting | 2 |
| Dispense event count since last product refill | 78 |
| Dispenses remaining until out of product/refill | 547 |

In other examples, (such as those in which the beacon modules do not communicate with an id badge), the dispenser data may include only an indication of the dispense event and an indication of bottle presence (yes or no). In other examples, the dispenser data may include an indication of a valid battery voltage instead of or in addition to the current battery level. In other examples, the dispenser data may include any one or all of the example dispenser data listed in Table 1, and/or other dispenser data. The dispense event count since last product refill may be reset each time a product bottle removal/replacement is detected by bottle presence triggers of the manual or touch free beacon modules.

Figure 17:
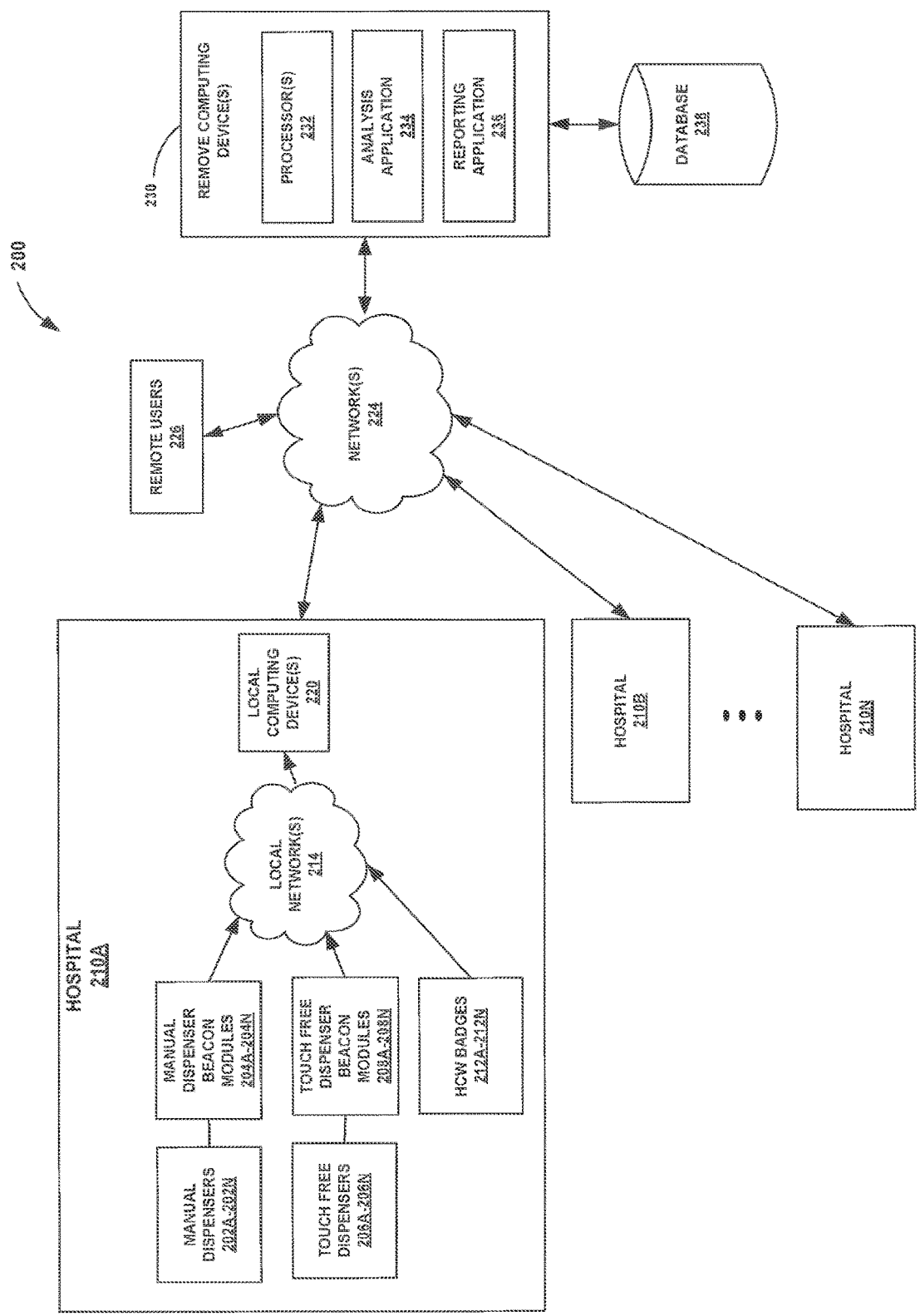
FIG. 17 is a block diagram of an example hand hygiene compliance monitoring system.

FIG. 17 is a block diagram of an example hand hygiene compliance monitoring system 200. A plurality of healthcare facilities, such as hospitals 210A-210N, each include a plurality of manual hand hygiene product dispensers 202A-202N and/or a plurality of touch free hand hygiene product dispensers 206A-206N. For simplicity of illustration, these are shown with respect to hospital 210A. Each of the plurality of manual dispensers 202A-202N is associated with a different one of a plurality of manual dispenser beacon modules 204A-204N that provide for wireless transmission of dispenser data. Similarly, each of the plurality of touch free dispensers 206A-206N is associated with a different one of a plurality of touch free dispenser beacon modules 208A-208N that provide for wireless transmission of dispenser data.

Dispenser beacon modules 203A-204N and 208A-208N wirelessly transmit their respective dispenser data to one or more local computing device(s) 220 via local network(s) 214. In the example where beacon modules transmit dispenser data upon the occurrence of each dispense event and does not include a time and date stamp in the dispenser data, local computing device will associate a time and date stamp with the dispense event.

In some examples, such as that shown in FIG. 17, hand hygiene compliance monitoring system 200 includes HCW badges 212A-212N. In this example, therefore, the dispenser data transmitted by beacon modules 204A-204N and/or 208A-208N may include HCW identification information received from badges 212A-212N.

To monitor hand hygiene compliance, dispenser data from the plurality of dispenser beacon modules 100/150 are wirelessly transmitted to one or more local computing device(s) 220 located within the healthcare facility and/or to remote computing device(s) 230 for data analysis and reporting. As shown in FIG. 17, for example, computing devices 230 may include one or more processor(s) 232, an analysis application 234, a reporting application 236, and a data base 238 that stores the requisite data used or generated by system 200. Analysis application 234, when executed by processors 232, analyzes the hand hygiene data in accordance with one or more compliance rules so as to monitor hand hygiene compliance with the healthcare facility. Reporting application 236, when executed by processors 232, generates reports regarding hand hygiene compliance. For example, computing devices 230 may analyze the hand hygiene data to monitor hand hygiene compliance by individual HCW, type of HCW (e.g., nurses, doctors, environmental services (EVS), etc.), department, type of department, individual hospital, type of hospital, across multiple hospitals, or by various other selected parameters. Computing devices 230 may generate a variety of reports to provide users local to each hospital 210A-210N or remote users 226 with both qualitative and quantitative data regarding hand hygiene compliance at their hospital, to compare data over time to determine whether improvement has occurred, and/or to benchmark hand hygiene compliance at one hospitals, at multiple hospitals, or to view and compare hand hygiene compliance over time. Analysis and reporting application may also be stored locally on hospital computing devices 220 so that analysis and reporting of hand hygiene data may be done locally if desired.

FIG. 18 is a flowchart illustrating an example process (240) by which a manual dispenser beacon module, such as beacon module 100, may detect manual actuations of a manual hand hygiene product dispenser and wirelessly transmit dispenser data associated with the dispense event. Beacon module 100 receives a dispenser actuation signal (242) indicative of actuation of the manual hand hygiene product dispenser. The actuation signal may be received from, for example, a switch configured to detect manual actuation of a manual hand hygiene product dispenser, such as switch 19 of FIGS. 3 and 4 and/or switch 114 of FIG. 15.

Beacon module 100 may further determine additional dispenser status information (244). For example, beacon module 100 may determine the current battery level, whether a bottle is present in the manual dispenser, may increment a count of the number of dispenses, may determine a number of dispenses remaining before the product bottle needs to be replaced or refilled, etc. Beacon module 100 then wirelessly transmits the dispense event data (246).

FIG. 19 is a flowchart illustrating another example process (250) by which a manual dispenser beacon module, such as beacon module 100, may detect manual actuations of a manual hand hygiene product dispenser and wirelessly transmit dispenser data associated with the dispense event. Beacon module 100 receives a dispenser actuation signal (252) indicative of actuation of the manual hand hygiene product dispenser. The actuation signal may be received from, for example, a switch configured to detect manual actuation of a manual hand hygiene product dispenser, such as switch 19 of FIGS. 3 and 4 and/or switch 114 of FIG. 15. In this example, beacon module controller 100 may then look for any HCW ID badge signals within range of the dispenser (254). For example, a wireless transceiver on beacon module controller may have an initial range of 0-1 meter or some other appropriate distance that helps to ensure that only the HCW ID badge associated with the HCW who initiated the dispense event is detected and not another nearby HCW id tag.

If a HCW ID badge signal is detected within a predefined period of time (256) (such as 0.5 seconds, 1 second, 2 seconds, 5 seconds or other appropriate time interval, for example), beacon module 100 associates the dispense event with the detected HCW identification information (258). If no HCW ID badge signal is detected within a predefined period of time, beacon module 100 associates the dispense event with non-HCW identification information (260).

Beacon module 100 may further determine additional dispenser status information (262). For example, beacon module 100 may determine the current battery level, whether a bottle is present in the manual dispenser, may increment a count of the number of dispenses, may determine a number of dispenses remaining before the product bottle needs to be replaced or refilled, etc. Beacon module 100 then wirelessly transmits the dispense event data (264).

FIG. 20 is a flowchart illustrating an example process (300) by which a touch free dispenser beacon module, such as beacon module 150, may detect actuations of a touch free hand hygiene product dispenser and wirelessly transmit dispenser data associated with the dispense event. Beacon module 150 receives a dispenser actuation signal (302) indicative of actuation of the touch free hand hygiene product dispenser. The actuation signal may be received from, for example, a touch free dispenser module (such as touch free dispenser module 170 of FIG. 16) that controls operation of, and thus detects actuation of, the touch free hand hygiene product dispenser.

Beacon module 150 may further determine additional dispenser status information (304). For example, beacon module 150 may determine the current battery level, whether a bottle is present in the touch free dispenser, may increment a count of the number of dispenses, may determine a number of dispenses remaining before the product bottle needs to be replaced or refilled, etc. Beacon module 150 then wirelessly transmits the dispense event data (306).

FIG. 21 is a flowchart illustrating another example process (310) by which a touch free dispenser beacon module, such as beacon module 150, may detect actuations of a touch free hand hygiene product dispenser and wirelessly transmit dispenser data associated with the dispense event. Beacon module 150 receives a dispenser actuation signal (312) indicative of actuation of the touch free hand hygiene product dispenser. The actuation signal may be received from, for example, a touch free dispenser module (such as touch free dispenser module 170 of FIG. 16) that controls operation of, and thus detects actuation of, the touch free hand hygiene product dispenser.

In this example, beacon module controller 150 may then look for any HCW ID badge signals within range of the dispenser (316). For example, a wireless transceiver on beacon module controller may have an initial range of 0-1 meter or some other appropriate distance that helps to ensure that only the HCW ID badge associated with the HCW who initiated the dispense event is detected and not another nearby HCW id tag.

If a HCW ID badge signal is detected within a predefined period of time (316) (such as 0.5 seconds, 1 second, 2 seconds, 5 seconds or other appropriate time interval, for example), beacon module 100 associates the dispense event with the detected HCW identification information (318). If no HCW ID badge signal is detected within a predefined period of time, beacon module 150 associates the dispense event with non-HCW identification information (320).

Beacon module 150 may further determine additional dispenser status information (322). For example, beacon module 150 may determine the current battery level, whether a bottle is present in the manual dispenser, may increment a count of the number of dispenses, may determine a number of dispenses remaining before the product bottle needs to be replaced or refilled, etc. Beacon module 150 then wirelessly transmits the dispense event data (324).

In accordance with one or more aspects of this disclosure, the term "or" may be interrupted as "and/or" where context does not dictate otherwise. Additionally, while phrases such as "one or more" or "at least one" or the like may have been used in some instances but not others, those instances where such language was not used may be interpreted to have such a meaning implied where context does not dictate otherwise.

In one or more examples, the functions described may be implemented in hardware, software, firmware, or any combination thereof. If implemented in software, the functions may be stored on or transmitted over, as one or more instructions or code, a computer-readable device or medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to non-transitory tangible computer-readable storage media. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used may refer to any of the foregoing structure or any other structure suitable for implementation of the techniques described. In addition, in some aspects, the functionality described may be provided within dedicated hardware and/or software modules. Also, the techniques could be fully implemented in one or more circuits or logic elements.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperating hardware units, including one or more processors as described above, in conjunction with suitable software and/or firmware.

Various examples have been described. These and other examples are within the scope of the following claims.

The invention claimed is:

1. A dispenser system comprising:
a dispenser beacon module configured to monitor actuations of a product dispenser, the dispenser beacon module including:
a module controller configured to generate dispenser data for each of a plurality of detected actuations of the product dispenser; and
one or more wireless transceivers configured to wirelessly transmit and/or receive data, wherein at least one of the one or more wireless transceivers is configured to wirelessly transmit and/or receive at least a portion of the dispenser data,
wherein the dispenser beacon module further includes a module housing sized to fit within a housing of the product dispenser, the module housing including a module base, and a bottle presence trigger configured on or about an outer surface of the module housing such that presence of a product bottle in the housing of the product dispenser provides a bottle presence signal indicative of presence of the product bottle in the housing of the product dispenser.

2. The system of claim 1, wherein the module controller is configured to receive identification information from one of a plurality of badges associated with one or more of the plurality of detected actuations of the product dispenser.

3. The system of claim 2, wherein the dispenser data for each of the plurality of detected actuations of the product dispenser includes the identification information.

4. The system of claim 2, wherein the product dispenser is one of a manually actuated hand hygiene product dispenser or a touch free hand hygiene product dispenser.

5. The system of claim 1, wherein the module controller is configured to receive a dispenser actuation signal from a switch that detects actuation of the product dispenser.

6. The system of claim 1, wherein the product dispenser is one of a manual product dispenser or a touch free product dispenser.

7. The system of claim 1, wherein the module controller is further configured to store a dispense event count upon receipt of a dispenser actuation signal.

8. The system of claim 1, further comprising a bottle presence trigger including a switch that changes from a first state to a second state when a product bottle is installed into the product dispenser; and wherein the module controller is further configured to reset a dispense event count when the product bottle is installed.

9. The system of claim 8, wherein the dispenser data includes the dispense event count.

10. The system of claim 8, wherein the bottle presence trigger includes one of a plunger switch, a pin switch, or a rocker switch.

11. The system of claim 1, further including an indicator that is illuminated by the module controller upon receipt of a dispenser actuation signal.

12. The system of claim 1, wherein the module housing further includes a module cover.

13. The system of claim 1, wherein the module housing is sized to be received into a receptacle within the housing of the product dispenser.

14. The system of claim 1, wherein the module controller is internal to the module housing.

15. The system of claim 1, wherein the module controller further determines status information corresponding to each of the detected actuations of the product dispenser, the status information including at least one of a battery level associated with the dispenser beacon module or a battery level associated with the product dispenser.

16. The system of claim 1, wherein the dispenser data for each of the plurality of the detected actuations of the product dispenser further includes at least one of a battery level associated with the dispenser beacon module, a battery level associated with the product dispenser, and a dispense event count.

17. The system of claim 1, wherein the dispenser beacon module further includes a power source that provides power to the module controller.

18. The system of claim 1, wherein the module controller receives power from the product dispenser.

19. The system of claim 1, wherein the module controller receives power from one or more batteries that also provide power to the product dispenser.

20. The system of claim 1, further comprising a computing system including:
- one or more processors; and
- one or more non-transitory storage devices comprising instructions that when executed by the one or more processors cause the one or more processors to:
- for each of a plurality of product dispensers, analyze dispenser data received for each of a plurality of detected actuations of the product dispenser and identify one or more of the detected actuations of the product dispenser for which the dispenser data includes a product bottle absence indication.

21. The system of claim 20, further comprising instructions that when executed by the one or more processors cause the one or more processors to generate an alert including the detected product bottle absence indication.

22. The system of claim 20, further comprising instructions that when executed by the one or more processors cause the one or more processors to, for each of the plurality of product dispensers, detect installation of a product bottle in the product dispenser.

23. The system of claim 20, wherein the computing device is configured to generate a product bottle replacement indication upon detection of installation of the product bottle in the product dispenser.

24. The system of claim 20, wherein the computing device is configured to generate a product bottle removal indication upon detection of removal of the product bottle from the product dispenser.

* * * * *